(12) United States Patent
Bodie et al.

(10) Patent No.: US 10,907,187 B2
(45) Date of Patent: Feb. 2, 2021

(54) FUNGAL STRAINS AND METHODS OF USE

(71) Applicant: DANISCO US INC., Palo Alto, CA (US)

(72) Inventors: Elizabeth A. Bodie, San Carlos, CA (US); Roman Rabinovich, Foster City, CA (US); Aleksandra Virag, Cupertino, CA (US); Michael Ward, San Francisco, CA (US); Rochelle Nguyen, Sunnyvale, CA (US); James A. Sweigard, Elkton, MD (US)

(73) Assignee: DANISCO US INC, Palo Alto, CA (US)

( * ) Notice: Subject to any disclaimer, the term of this patent is extended or adjusted under 35 U.S.C. 154(b) by 0 days.

(21) Appl. No.: 15/549,376

(22) PCT Filed: Feb. 9, 2016

(86) PCT No.: PCT/US2016/017113
§ 371 (c)(1),
(2) Date: Aug. 7, 2017

(87) PCT Pub. No.: WO2016/130523
PCT Pub. Date: Aug. 18, 2016

(65) Prior Publication Data
US 2018/0037919 A1 Feb. 8, 2018

Related U.S. Application Data

(60) Provisional application No. 62/173,511, filed on Jun. 10, 2015, provisional application No. 62/113,905, filed on Feb. 9, 2015.

(51) Int. Cl.
*C12P 21/02* (2006.01)
*C12N 15/01* (2006.01)
*C12N 9/12* (2006.01)

(52) U.S. Cl.
CPC .............. *C12P 21/02* (2013.01); *C12N 9/12* (2013.01); *C12N 15/01* (2013.01); *C12Y 207/13003* (2013.01)

(58) Field of Classification Search
CPC .. C12Y 207/13003; C12N 15/01; C12N 9/12; C12P 21/02
See application file for complete search history.

(56) References Cited

U.S. PATENT DOCUMENTS

| | | | |
|---|---|---|---|
| 6,022,725 A | 2/2000 | Fowler et al. | |
| 6,268,328 B1 | 7/2001 | Mitchinson et al. | |
| 6,361,966 B1 | 3/2002 | Walker et al. | |
| 2004/0171154 A1 | 9/2004 | Storici et al. | |

FOREIGN PATENT DOCUMENTS

| | | |
|---|---|---|
| EP | 0244234 B2 | 11/2001 |
| EP | 0215594 B2 | 10/2003 |
| EP | 1415996 A2 | 5/2004 |
| WO | 98/44148 A1 | 10/1998 |

OTHER PUBLICATIONS

Fillinger et al.; Functional and Structural Comparison of Pyrrolnitrin and Iprodione-Induced Modifications in the Class III Histidine-Kinase Bos1 of Botrytis cinerea; PLOS One; vol. 7, No. 8, pp. 1-14, e42520, Aug. 2012 (Year: 2012).*
Yoshimi et al., "Cloning and characterization of the histidine kinase gene Dic1 from Cochliobolus heterostrophus that confers dicarboximide resistance and osmotic adaptation," Mol. Genet. Gennomics, 2004, vol. 271, pp. 228-236.
Wolanin et al., "Histidine protein kinases: key signal transducers outside the animal kingdom," Genome Biol., 2002, vol. 3, No. 10, pp. 3013.1-3103.8.
Weiss et al., "Phosphorylation of nitrogen regulator I of *Escherichia coli* induces strong cooperative binding to DNA essential for activation of transcription," Proc. Natl. Acad. Sci. USA, 1992, vol. 89, pp. 5088-5092.
Webber et al., "Involvement of the amino-terminal phosphorylation module of UhpA in activation of uhpT transcription in *Escherichia coli*," Mol. Microbiol., 1997, vol. 24, pp. 1039-1048.
Ward, "Production of recombinant proteins by filamentous fungi," Biotechnology Advances, 2012, vol. 30, No. 5, pp. 1119-1139.
Vogel, "Distribution of Lysine Pathways Among Fungi: Evolutionary Implications," Am. Nat., 1964, vol. 98, pp. 435-446.
Vogel, "A convenient growth medium for Neurospora (Medium N)," Microbial Genet. Bull., 1956, vol. 13, pp. 42-43, Cold Spring Harbor, Long Island, New York.
Viaud et al., "Effects of Temperature on Xylanase Secretion by Trichoderma reesei," Mol. Plant Microbe Interact., 2006, vol. 19, pp. 1042-1050.
Suh et al., "Effects of Temperature on Xylanase Secretion by Trichoderma reesei," Biotechnology and Bioengineering, 1988, vol. 32, pp. 821-825.
Sugui et al., "Agrobacterium tumefaciens-Mediated Transformation of *Aspergillus fumigatus*: an Efficient Tool for Insertional Mutagenesis and Targeted Gene Disruption," Appl. Environ. Microbiol., 2005, vol. 71, pp. 1798-1780.
Storici et al., "In vivo site-directed mutagenesis using oligonucleotides," Nature Biotechnol., 2001, vol. 19, pp. 773-776.
Stock et al., "Two-Component Signal Transduction," Ann. Rev. Biochem., 2000, vol. 69, pp. 183-215.
Sheir-Neiss et al., "Characterization of the secreted cellulases of Trichoderma reesei wild type and mutants during controlled fermentations," Appl. Microbiol. Biotechnol., 1984, vol. 20, pp. 46-53.
Selifonova et al., "Rapid Evolution of Novel Traits in Microorganisms," Appl Environ. Microbio., 2001, vol. 67, pp. 3645-3649.
Schumacher et al., "The Osmotic-1 Locus of Neurospora crassa Encodes a Putative Histidine Kinase Similar to Osmosensors of Bacteria and Yeast," Curr. Microbiol., 1997, vol. 34, pp. 340-347.
Scherer et al., "Replacement of chromosome segments with altered DNA sequences constructed in vitro," Proc. Natl. Acad. Sci. USA, 1979, vol. 76, pp. 4949-4955.

(Continued)

*Primary Examiner* — Antonio Galisteo Gonzalez

(57) ABSTRACT

Provided are improved fungal strains and use thereof, wherein the fungal strains are capable of producing an altered level of proteins, enzymes, variants and other substances of interest.

3 Claims, 22 Drawing Sheets
Specification includes a Sequence Listing.

(56) References Cited

OTHER PUBLICATIONS

Posas et al., "Yeast HOG1 MAP Kinase Cascade Is Regulated by a Multistep Phosphorelay Mechanism in the SLN1-YPD1-SSK1 "Two-Component" Osmosensor," Cell, 1996, vol. 86, pp. 865-875.
Penttila et al., "A versatile transformation system for the cellulolytic filamentous fungus Trichoderma reesei," Gene, 1987, vol. 61, pp. 155-164.
Peberdy, "Protein secretion in filamentous fungi—trying to understand a highly productive black box," Trends in BioTechnology, 1994, vol. 12, pp. 50-57.
PCT International Search Report and the Written Opinion of the International Searching Authority for International Application No. PCT/US2016/017113, ISA/EPO; dated May 23, 2016.
Patnaik, "Engineering Complex Phenotypes in Industrial Strains," Biotechnol. Prog., 2008, vol. 24, pp. 38-47.
Ota et al., "A Yeast Protein Similar to Bacterial Two-Component Regulators," Science, 1993, vol. 262, pp. 566-569.
Oshima et al., "Survey of mutations of a histidine kinase gene BcOSI in dicarboximide-resistant field isolates of Botrytis cinerea," Journal of General Plant Pathology, 2006, vol. 72, pp. 65-73.
Oshima et al., "A Point Mutation in the Two-Component Histidine Kinase BcOS-1 Gene Confers Dicarboximide Resistance in Field Isolates of Botrytis cinerea," Phytopathology, 2002, vol. 92, No. 1, pp. 75-80.
Ochiai et al., "Characterization of mutations in the two-component histidine kinase gene that confer fludioxonil resistance and osmotic sensitivity in the os-1 mutants of Neurospora crassa," Pest. Manag. Sci., 2001, vol. 57, pp. 437-442.
Newton, "Protein Kinase C: Structural and Spatial Regulation by Phosphorylation, Cofactors, and Macromolecular Interactions," Chem. Rev., 2001, vol. 101, pp. 2353-2364.
Nemecek et al., "Global Control of Dimorphism and Virulence in Fungi," Science, 2006, vol. 312, pp. 583-588.
Nalankilli, "Application of enzymes in eco-friendly wet processing of cotton," Colourage, 1998, vol. 45, No. 10, pp. 17-19.
Motoyama et al., "An Os-1 family histidine kinase from a filamentous fungus confers fungicide-sensitivity to yeast," Curr. Genet., 2005, vol. 47, pp. 298-306.
Miller, "Mutators in *E coli*," In a Short Course in Bacterial Genetics: A Laboratory Manual and Handbook for *Escherichia coli* and Related Bacteria, 1992, Unit 4: Mutagenesis, pp. 110-113, Cold Spring Harbor Laboratory Press, Plainview, N.Y.
Miller et al., "Molecular Dissection of Alleles of the osmotic-1 Locus of Neurospora crassa," Fungal Genet. Biol., 2002, vol. 35, pp. 147-155.
Mackenzie et al., "Regulation of secreted protein production by filamentous fungi: recent developments and perspectives," J. Gen. Microbiol., 1993, vol. 139, pp. 2295-2307.
Ma et al., "Sequence variation in the two-component histidine kinase gene of Botrytis cinerea associated with resistance to dicarboximide fungicides," Pesticide Biochemistry and Physiology, 2007, vol. 88, No. 3, pp. 300-306.
Li et al., "The yeast histidine protein kinase, Sln1p, mediates phosphotransfer to two response regulators, Ssk1p and Skn7p," EMBO J., 1998, vol. 17, pp. 6952-6962.
Kren et al., "In vivo site-directed mutagenesis of the factor IX gene by chimeric RNA/DNA oligonucleotides," Nat. Med., 1998, vol. 4, pp. 285-290.
Kleckner et al., "Uses of Transposons with Emphasis on Tn10," In Methods Enzymol., 1991, vol. 204, pp. 139-180.
Islas-Flores et al., "The Amazing Role of the Group III of Histidine Kinases in Plant Pathogenic Fungi, an Insight to Fungicide Resistance," Asian J. Biochem., 2011, vol. 6, pp. 1-14.
Hohmann, "Osmotic Stress Signaling and Osmoadaptation in Yeasts," Mol. Biol. Rev., 2002, vol. 66, pp. 300-372.
Harlocker et al., "Tandem Binding of Six OmpR Proteins to the ompF Upstream Regulatory Sequence of *Escherichia coli*," J. Biol. Chem., 1995, vol. 270, pp. 26849-26856.
Harkki et al., "Genetic engineering of Trichoderma to produce strains with novel cellulase profiles," Enzyme Microb. Technol., 1991, vol. 13, pp. 227-233.
Harkki et al., "A Novel Fungal Expression System: Secretion of Active Calf Chymosin From the Filamentous Fungus Trichoderma Riesei," Bio/Technol., 1989, vol. 7, pp. 596-603.
Hagiwara et al., "NikA/TcsC Histidine Kinase Is Involved in Conidiation, Hyphal Morphology, and Responses to Osmotic Stress and Antifungal Chemicals in Aspergillus fumigatus," PLOS ONE, 2013, vol. 8, No. 12, pp. 1-14.
Hagiwara et al., "Characterization of NikA Histidine Kinase and Two Response Regulators with Special Reference to Osmotic Adaptation and Asexual Development in Aspergillus nidulans," Biosci. Biotechnol. Biochem., 2009, vol. 73, No. 7, pp. 1566-1571.
Grebe et al., "The Histidine Protein Kinase Superfamily," Adv. Microb. Physiol., 1999, vol. 41, pp. 139-227.
Goodman et al., "Direct interaction between sensor kinase proteins mediates acute and chronic disease phenotypes in a bacterial pathogen," Genes Dev., 2009, vol. 23, pp. 249-259.
Furukawa et al., "Isolation and Functional Analysis of a Gene, tcsB, Encoding a Transmembrane Hybrid-Type Histidine Kinase from Aspergillus nidulans," Appl. Environ. Microbiol., 2002, vol. 6, pp. 5304-5310.
Foster, "In Vivo Mutagenesis," In Methods Enzymol., 1991, vol. 204, pp. 114-125.
Fillinger et al, "Functional and Structural Comparison of Pyrrolnitrin- and Iprodione-Induced Modifications in the Class III Histidine-Kinase Bos1 of Botrytis cinerea", Plos One, 2012, vol. 7(8), pp. 1-14.
Dongo et al., "The Group III Two-Component Histidine Kinase of Filamentous Fungi is Involved in the Fungicidal Activity of the Bacterial Polyketide Ambruticin," Appl. Environ. Microbiol., 2009, vol. 75, pp. 127-134.
Davis et al., "Genetic and Microbiological Research Techniques for Neurospora crassa," In Methods in Enzymology, 1970, vol. 17A, Tabor et al., Eds., pp. 79-143.
Cui et al., "An osmosensing histidine kinase mediates dicarboximide fungicide resistance in Botryotinia fuckeliana (Botrytis cinerea)," Fungal Genet. Biol., 2002, vol. 36, pp. 187-198.
Cobb et al., "Dimerization in MAP-kinase signaling," Trends Biochem. Sci., 2000, vol. 25, pp. 7-9.
Chelikani et al., "Diversity of structures and properties among catalases," Cell Mol. Life Sci., 2004, vol. 61, pp. 192-208.
Catlett et al., "Whole-Genome Analysis of Two-Component Signal Transduction in Fungal Pathogens," Eukaryot. Cell, 2003, vol. 2, 1151-1161.
Cao et al., "Penicillopepsin-JT2, a recombinant enzyme from Penicillium janthinellum and the contribution of a hydrogen bond in subsite S3 to kcat," Protein Science, 2000, vol. 9, pp. 991-1001.
Campbell et al., "Improved transformation efficiency of Aspergillus niger using the homologous niaD gene for nitrate reductase," Curr. Genet., 1989, vol. 16, pp. 53-56.
Calissano et al., "In vivo site-directed mutagenesis of Neurospora crassa beta-tubulin gene by spheroplasts transformation with oligonucleotides," Fungal Genet. Newslett., 1996, vol. 43, pp. 15-16.
Blat et al., "Oligomerization of the Phosphatase CheZ Upon Interaction with the Phosphorylated Form of CheY," Biochemistry, 1994, vol. 33, pp. 902-906.
Barton et al., "Site-directed, recombination-mediated mutagenesis of a complex gene locus, " Nucleic Acids Res., 1990, vol. 18, pp. 7349-4966.
Ausubel et al., (Eds.), "Introduction of DNA into Mammalian Cells," In Short Protocols in Molecular Biology, Third Edition, 1987, John Wiley Sons, Inc., Chapter 9, pp. 9-1 through 9-57.
Aravind et al., "The cytoplasmic helical linker domain of receptor histidine kinase and methyl-accepting proteins is common to many prokaryotic signalling proteins," FEMS Microbiol. Lett., 1999, vol. 176, pp. 111-116.
Alex et al., "Hyphal development in Neurospora crassa: Involvement of a two-component histidine kinase," Proc. Natl. Acad. Sci. USA, 1996, vol. 93,, pp. 3416-3421.

(56) References Cited

OTHER PUBLICATIONS

Aiba et al., "Phosphorylation of a Bacterial Activator Protein, OmpR, by a Protein Kinase, EnvZ, Results in Stimulation of Its DNA-Binding Ability," J. Biochem., 1989, vol. 106, pp. 5-7.

* cited by examiner

FUNGAL STRAINS AND METHODS OF USE

CROSS-REFERENCE TO RELATED APPLICATIONS

The present application is the National Stage of International Application PCT Patent Application No PCT/US2016/017113, filed on Feb. 9, 2016, which claims priority to U.S. Provisional Patent Application Ser. No. 62/113,905, filed Feb. 9, 2015 and U.S. Provisional Patent Application Ser. No. 62/173,511, filed Jun. 10, 2015 which are hereby incorporated by reference in their entirety.

FIELD OF THE INVENTION

The present disclosure relates to an engineered, transformed or derivative fungal strain capable of producing an altered level of a protein of interest, and the methods of genetically modifying a fungal strain such that it has an ability to produce an altered level of protein of interest. Moreover, the present disclosure pertains to a protein of interest produced by fermenting this engineered, transformed or derivative fungal strain and a composition comprising this protein of interest. Furthermore, the present disclosure pertains to a method of producing a protein of interest employing an engineered, transformed or derivative fungal strain, as well as a method of producing and using a composition comprising this protein of interest. The proteins of interest herein may be endogenous proteins or heterologous proteins. The present disclosure also relates to a method for identifying or selecting for an engineered fungal strain capable of producing an altered level of a protein of interest as compared to a parental strain.

REFERENCE TO THE SEQUENCE LISTING

The contents of the electronic submission of the text file Sequence Listing, named "NB40733-US-PCT-SEQ_Listing.txt," was created on Nov. 2, 2017, and is 31 KB in size, is hereby incorporated by reference in its entirety.

REFERENCE TO A DEPOSIT OF BIOLOGICAL MATERIAL

This application contains a reference to a deposit of biological material, which deposit incorporated herein by reference. Specifically CBS140022, a *Trichoderma reesei* strain RLP37 Nik1 (M743T) was deposited under the terms of the Budapest Treaty on the International Recognition of the Deposit of Microorganisms for the Purposes of Patent Procedure at Centraalbureau voor Schimmelcultures, Fungal Biodiversity Centre, Institute of the Royal Netherlands Academy of Arts and Sciences (KNAW), Uppsalalaan 8, 3584 CT Utrecht, the Netherlands.

BACKGROUND OF THE INVENTION

Fungi are known for their commercial applications both as industrial products for their endogenous proteins, and as expression hosts for producing industrially useful proteins. In an example of the direct industrial use of fungi, filamentous fungal strains such as *Trichoderma reesei, Humicola insolens, Fusarium oxysporum*, and the like, have been applied directly on cellulosic biomass to help break down cellulose and hemicellulose components of such materials into small polymeric and/or monomeric sugars that can be further processed into industrially useful substances. However such direct uses have thus far proven not economically viable largely because of the inherent limitations of the amount of total proteins/enzymes that might be produced by these organisms, especially when counterbalanced by the high levels of enzymatic activities that would be required to break down recalcitrant substrates such as cellulosic biomass.

On the other hand, the use of fungal strains as production hosts for proteins of interest have long been deemed economically viable and widely used in commercial settings for some time. Filamentous fungi's capacity to secret complex proteins, accurately folded into their 3-dimensional structures and disulfide bonds, precisely proteolytically clipped following translation, and relatively predictably glycosylated with n-linked and o-linked glycosylation reactions, renders these organisms highly attractive hosts for producing secreted proteins (MacKenzie, D. A. et al., J Gen Microbiol (1993) 139:2295-2307; Peberdy, J. F., Trends in BioTechnology (1994) 12:50-57). Fungi are known to be efficient enzyme producers for biomass hydrolysis, food and feed additives, textile application, grain processing, cleaning and other industrial usages.

The use of fungal expressed proteins for industrial processes is widespread and steadily increasing, especially given the present interest in employing industrial processes involving enzymes to generate fuels and chemicals from non-petroleum renewable materials or sources. Various techniques of improving the expression of proteins have been developed in the field. Those include, for example, classical strain improvement methods such as subjecting strains to multiple rounds of mutagenesis and selection for high producers, building or genetically engineering a production strain with high copy number of gene of interest inserted into the genome. While many of these methods are effective at improving productivity of the strain, they have limitations including, for example, the labor intensity of strain construction exercise typically required for making each individual product. Therefore, there remains a need for the obtaining of improved fungal strains capable of increased protein production for single proteins of interest, or for panels of proteins of interest, or even for endogenous proteins.

SUMMARY OF THE INVENTION

The present disclosure relates to an engineered, transformed or derivative fungal strain capable of producing an altered level of a protein of interest, and the methods of genetically modifying a fungal strain such that it has an ability to produce an altered level of protein of interest. Moreover, the present disclosure pertains to a protein of interest produced by fermenting this engineered, transformed or derivative fungal strain and a composition comprising this protein of interest. Furthermore, the present disclosure pertains to a method of producing a protein of interest employing an engineered, transformed or derivative fungal strain, as well as a method of producing and using a composition comprising the protein of interest. The present disclosure also relates to a method for identifying or selecting for an engineered fungal strain capable of producing an altered level of a protein of interest as compared to a parental strain.

In a first aspect, the present disclosure provides an engineered fungal strain, capable of producing an altered level of a protein of interest as compared to a parental strain, wherein the fungal strain comprises a variant histidine kinase gene and/or expresses a variant histidine kinase.

In some embodiments, the variant histidine kinase gene is a variant of a wild type histidine kinase gene which encodes a hybrid-type histidine kinase. In some embodiments, the variant histidine kinase gene is a variant of a wild type gene encoding a group III histidine kinase. In certain embodiments, the variant histidine kinase gene encodes a polypeptide that functions as part of a signaling pathway that responds to external osmotic pressure. Strains with mutations in the histidine kinase can be identified by screening for resistance or sensitivity to certain antifungal compounds, such as, for example, in the presence of high levels of a dicarboximide fungicide such as iprodione or fludioxonil in the medium. It is to be expected that mutations in other components of this signaling pathway would also be beneficial. These components include, without limitation, MAP kinase proteins and transcription factors that regulate expression of other genes in response to osmotic pressure. Strains with mutations in this pathway can be identified by screening for resistance or sensitivity to osmotic stress, such as, for example, in the presence of high levels of sorbitol or salt in the medium. Therefore, relatedly, the present disclosure also provides a method of identifying fungal strains having resistance or sensitivity to osmotic stress, which are advantaged as host organisms useful for producing industrially useful molecules.

In certain embodiments, a variant histidine kinase gene encodes a polypeptide comprising an amino acid sequence that is at least about 60% (e.g., at least about 60%, at least about 65%, at least about 70%, at least about 75%, at least about 80%, at least about 85%, at least about 90%, at least about 95%, at least about 96%, at least about 97%, at least about 98%, at least about 99%, or even higher %) identical to SEQ ID NO: 1 or SEQ ID NO: 43, but is not 100% identical to SEQ ID NO:1 or SEQ ID NO: 43.

In certain embodiments, the variant histidine kinase gene of the engineered fungal strain of this aspect encodes an amino acid sequence that is at least about 60% (e.g., at least about 60%, at least about 65%, at least about 70%, at least about 75%, at least about 80%, at least about 85%, at least about 90%, at least about 95%, at least about 96%, at least about 97%, at least about 98%, at least about 99%, or even higher %) identical to SEQ ID NO: 1 and a mutation at position 743 of SEQ ID NO:1. In particular embodiments, the mutation at position 743 of SEQ ID NO:1 is one replacing the methionine residue at that position with a threonine residue, namely, M743T.

In other embodiments, the variant histidine kinase gene of the engineered fungal strain of this aspect encodes an amino acid sequence that is at least about 60% (e.g., at least about 60%, at least about 65%, at least about 70%, at least about 75%, at least about 80%, at least about 85%, at least about 90%, at least about 95%, at least about 96%, at least about 97%, at least about 98%, at least about 99%, or even higher %) identical to SEQ ID NO: 43 and a mutation at position 786 of SEQ ID NO: 43. In particular embodiments, the mutation at position 786 of SEQ ID NO:1 is one replacing the methionine residue at that position with a threonine residue, namely, M786T.

In some embodiments, the parental strain of the engineered fungal strain of this aspect is an Ascomycete fungal strain. In particular embodiments, the parental strain is a filamentous fungal strain. Relatedly, the engineered fungal strain comprises a variant histidine kinase encoded by a variant histidine kinase gene, wherein the variant histidine kinase comprises an amino acid sequence that is at least about 60% (e.g., at least about 60%, at least about 65%, at least about 70%, at least about 75%, at least about 80%, at least about 85%, at least about 90%, at least about 95%, at least about 96%, at least about 97%, at least about 98%, at least about 99%, or even higher %) identical to: SEQ ID NO:1 and a mutation at position 743 of SEQ ID NO:1 or SEQ ID NO: 43 and a mutation at position 786 of SEQ ID NO: 43.

In some embodiments, the engineered fungal strain of this aspect is capable of producing a much greater amount of a protein of interest as compared to its parental strain. For example, the engineered fungal strain is capable of producing at least about 5%, at least about 10%, at least about 20%, at least about 50%, at least about 75%, at least about 100%, or even at least about 150% greater amounts of a protein of interest as compared to its parental strain.

In a second aspect, the present disclosure provides a transformed fungal strain or a derivative fungal strain thereof, capable of producing an altered level of a protein of interest as compared to a parental strain, wherein the transformed fungal strain or the derivative fungal strain comprises a variant histidine kinase gene.

In some embodiments, the variant histidine kinase gene of the transformed fungal strain or the derivative fungal strain thereof is a variant of a wild type histidine kinase gene encoding a hybrid-type histidine kinase. In some embodiments, the variant histidine kinase gene of the transformed fungal strain or the derivative fungal strain thereof is a variant of a wild type histidine kinase gene encoding a group III histidine kinase. In certain embodiments, the variant histidine kinase gene encodes a polypeptide that functions as part of a signaling pathway that responds to external osmotic pressure. Strains with mutations in this histidine kinase can be identified by selecting or screening for resistance or sensitivity to certain antifungal compounds, such as, for example, in the presence of high levels of a dicarboximide or phenylpyrrole fungicides such as iprodione or fludioxonil in the medium. It is to be expected that mutations in other components of this signaling pathway would also be beneficial. These components include, without limitation, MAP kinase proteins and transcription factors that regulate expression of other genes in response to osmotic pressure. Strains with mutations in this pathway can be identified by screening for resistance or sensitivity to osmotic stress, such as, for example, in the presence of high levels of sorbitol or salt in the medium.

In certain embodiments, the variant histidine kinase gene of the transformed fungal strain or the derivative fungal strain of this aspect encodes a polypeptide comprising an amino acid sequence that is at least about 60% (e.g., at least about 60%, at least about 65%, at least about 70%, at least about 75%, at least about 80%, at least about 85%, at least about 90%, at least about 95%, at least about 96%, at least about 97%, at least about 98%, at least about 99%, or even higher %) identical to SEQ ID NO:1 or SEQ ID NO: 43, but is not 100% identical to SEQ ID NO:1 or SEQ ID NO: 43. For instance, in certain embodiments, the variant histidine kinase gene of the engineered fungal strain of this aspect encodes an amino acid sequence that is at least about 60% (e.g., at least about 60%, at least about 65%, at least about 70%, at least about 75%, at least about 80%, at least about 85%, at least about 90%, at least about 95%, at least about 96%, at least about 97%, at least about 98%, at least about 99%, or even higher %) identical to SEQ ID NO:1 and a mutation at position 743 of SEQ ID NO:1. In particular embodiments, the mutation at position 743 of SEQ ID NO:1 is one replacing the methionine residue at that position with a threonine residue, namely, M743T. In other embodiments, the variant histidine kinase gene of the engineered fungal strain of this aspect encodes an amino acid sequence that is at least about 60% (e.g., at least about 60%, at least about 65%, at least about 70%, at least about 75%, at least about 80%, at least about 85%, at least about 90%, at least about 95%, at least about 96%, at least about 97%, at least about 98%, at least about 99%, or even higher %) identical to SEQ ID NO: 43 and a mutation at position 786 of SEQ ID NO: 43. In particular embodiments, the mutation at position 786 of SEQ ID NO: 43 is one replacing the methionine residue at that position with a threonine residue, namely, M786T In some embodiments, the parental strain of the engineered fungal strain of this aspect is an Ascomycete fungal strain. In particular embodiments, the parental strain is a filamentous fungal strain. Relatedly, the engineered fungal strain comprises a variant histidine kinase encoded by a variant histidine kinase gene, wherein the variant histidine kinase comprises an amino acid sequence that is at least about 60% (e.g., at least about 60%, at least about 65%, at least about 70%, at least about 75%, at least about 80%, at least about 85%, at least about 90%, at least about 95%, at least about 96%, at least about 97%, at least about 98%, at least about 99%, or even higher %) identical to: SEQ ID NO:1 and a mutation at position 743 of SEQ ID NO:1 or SEQ ID NO: 43 and a mutation at position 786 of SEQ ID NO: 43.

In some embodiments, the transformed fungal strain or the derivative fungal strain of this aspect is capable of producing a much greater amount of a protein of interest as compared to its parental strain. For example, the transformed fungal strain or the derivative fungal strain of this aspect is capable of producing at least about 5%, at least about 10%, at least about 20%, at least about 50%, at least about 75%, at least about 100%, or even at least about 150% greater amounts of a protein of interest as compared to its parental strain.

In a third aspect, the present disclosure provides a method for improving protein production by an engineered, transformed, or derivative fungal strain, as compared to its parental strain, comprising employing an engineered, transformed or derivative fungal strain, wherein the engineered, transformed or derivative fungal strain comprises a variant histidine kinase gene.

In some embodiments, the variant histidine kinase gene employed in the method of this aspect is a variant of a wild type histidine kinase gene encoding a hybrid-type histidine kinase. In some embodiments, the variant histidine kinase gene is a variant of a wild type histidine kinase gene encoding a group III histidine kinase. In certain embodiments, the variant histidine kinase gene encodes a polypeptide that functions as part of a signaling pathway that responds to external osmotic pressure. Strains with mutations in this histidine kinase can be identified by selecting or screening for resistance or sensitivity to certain antifungal compounds, such as, for example, in the presence of high levels of a dicarboximide or phenylpyrrole fungicide such as iprodione or fludioxonil in the medium. It is to be expected that mutations in other components of this signaling pathway would also be beneficial. These components include, without limitation, MAP kinase proteins and transcription factors that regulate expression of other genes in response to osmotic pressure. Strains with mutations in this pathway can be identified by screening for resistance or sensitivity to osmotic stress, such as, for example, in the presence of high levels of sorbitol or salt in the medium.

In certain embodiments, the variant histidine kinase gene employed in the method of this aspect encodes a polypeptide comprising an amino acid sequence that is at least about 60% (e.g., at least about 60%, at least about 65%, at least about 70%, at least about 75%, at least about 80%, at least about 85%, at least about 90%, at least about 95%, at least about 96%, at least about 97%, at least about 98%, at least about 99%, or even higher %) identical to SEQ ID NO:1 or SEQ ID NO: 43, but is not 100% identical to SEQ ID NO:1 or SEQ ID NO: 43. For instance, the variant histidine kinase gene employed in the method of this aspect encodes an amino acid sequence that is at least about 60% (e.g., at least about 60%, at least about 65%, at least about 70%, at least about 75%, at least about 80%, at least about 85%, at least about 90%, at least about 95%, at least about 96%, at least about 97%, at least about 98%, at least about 99%, or even higher %) identical to: SEQ ID NO:1, and a mutation at position 743 of SEQ ID NO: 1 or SEQ ID NO: 43 and a mutation at position 786 of SEQ ID NO: 43. In certain particular embodiments, the mutation at position 743 of SEQ ID NO:1 is one replacing the methionine residue at that position with a threonine residue, namely, M743T. In other embodiments, the mutation at position 786 of SEQ ID NO: 43 is one replacing the methionine residue at that position with a threonine residue, namely, M786T In some embodiments, the parental strain of the engineered fungal strain as employed in the method of this aspect is an Ascomycete fungal strain. In particular embodiments, the parental strain is a filamentous fungal strain. Relatedly, the engineered fungal strain comprises a variant histidine kinase encoded by a variant histidine kinase gene, wherein the variant histidine kinase comprises an amino acid sequence that is at least about 60% (e.g., at least about 60%, at least about 65%, at least about 70%, at least about 75%, at least about 80%, at least about 85%, at least about 90%, at least about 95%, at least about 96%, at least about 97%, at least about 98%, at least about 99%, or even higher %) identical to SEQ ID NO: 1, and a mutation at position 743 of SEQ ID NO: 1 or SEQ ID NO: 43 and a mutation at position 786 of SEQ ID NO: 43.

In some embodiments, the engineered, transformed or derivative fungal strain employed in the method of this aspect is capable of producing a much greater amount of a protein of interest, as compared to its parental strain. For example, the engineered, transformed or derivative fungal strain is capable of producing at least about 5%, at least about 10%, at least about 20%, at least about 50%, at least about 75%, at least about 100%, or even at least about 150% greater amounts of a protein of interest as compared to its parental strain.

In another aspect, the present disclosure provides a method of producing a protein of interest comprising fermenting an engineered, transformed or derivative fungal strain as described herein, wherein the engineered, transformed or derivative fungal strain comprises a variant histidine kinase gene and/or expresses a histidine kinase encoded by the variant histidine kinase gene, secretes the protein of interest.

In yet another aspect, the present disclosure provides a protein of interest produced by fermenting an engineered, transformed or derivative fungal strain, such as one described herein, wherein the engineered, transformed or derivative fungal strain comprises a variant histidine kinase gene and/or expresses a histidine kinase encoded by the variant histidine kinase gene.

In embodiments of any of the aspects of invention herein, the protein of interest may be a hemicellulase, a peroxidase, a protease, a cellulase, a xylanase, a lipase, a phospholipase, an esterase, a cutinase, a pectinase, a keratinase, a reductase, an oxidase, a phenol oxidase, a lipoxygenase, a ligninase, a pullulanase, a tannase, a pentosanase, a mannanase, a beta-glucanase, an arabinosidase, a hyaluronidase, a chondroitinase, a laccase, an amylase, a glucoamylase, a mixture thereof, a functional fragment thereof, or a mixture of one or more of the enzymes or functional fragments thereof. Non-limiting examples of proteins may further include proteins or enzymes involved in starch metabolism, proteins or enzymes involved in glycogen metabolism, acetyl esterases, aminopeptidases, amylases, arabinases, arabinofuranosidases, carboxypeptidases, catalases, cellulases, chitinases, chymosin, cutinase, deoxyribonucleases, epimerases, esterases, α-galactosidases, β-galactosidases, α-glucanases, glucan lysases, endo-β-glucanases, glucoamylases, glucose oxidases, α-glucosidases, β-glucosidases, glucuronidases, hemicellulases, hexose oxidases, hydrolases, invertases, isomerases, laccases, lipases, lyases, mannosidases, oxidases, oxidoreductases, pectate lyases, pectin acetyl esterases, pectin depolymerases, pectin methyl esterases, pectinolytic enzymes, peroxidases, phenoloxidases, phytases, polygalacturonases, proteases, rhamno-galacturonases, ribonucleases, thaumatin, transferases, transport proteins, transglutaminases, xylanases, hexose oxidase (D-hexose: 02-oxidoreductase, EC 1.1.3.5), variants thereof, functional fragments thereof, or combinations thereof. The protein of interest may also be a peptide hormone, a growth factor, a clotting factor, a chemokine, a cytokine, a lymphokine, an antibody, a receptor, an adhesion molecule, a microbial antigen (e.g., HBV surface antigen, HPV E7, etc.), or a variant, functional fragment, or a mixture of two of more of the above substances.

In certain related aspect, the disclosure provides a composition comprising the protein of interest of any of the aspects described herein. The disclosure also provides a method of using such a composition in biomass hydrolysis, cleaning applications, grain processing, animal nutrition, food composition, textile treatment, or the like.

In a further aspect, the disclosure provides a method for identifying or screening for an engineered fungal strain capable of producing an altered level of a protein of interest, as compared (relative) to a parental strain, comprising the steps of:
(a) inoculating the strain onto the surface of agar plate with osmotic agents or/and dicarboximide fungicide; and
(b) screening or selecting the strains that grow faster or slower than the parental strain.

For example, in certain embodiments, osmotic agents include, but are not limited to, sugars, sugar alcohols and salts. In certain embodiments, an osmotic agent is a sugar, including, but not limited to, glucose, sucrose, fructose, oligofructose, fructo-oligosaccharide, inverted sugar and the like. In certain other embodiments, an osmotic agent is a sugar alcohol, including, but not limited to, sorbitol, xylitol, galactosylosorbitol and the like. In yet other embodiments, an osmotic agent is a salt, including, but not limited to, sodium chloride and potassium chloride. In another embodiment, a fungicide is a dicarboximide or phenylpyrole. In particular embodiments, a fungicide is iprodione or fludioxnil.

In some embodiments of this aspect, the engineered fungal strain capable of producing an altered level of a protein of interest as compared to a parental strain, comprises a mutation that causes altered sensitivity or resistance to external osmotic pressure as compared to the parental strain. Not wishing to be bound by theory, however, it can be expected that mutations in other components of this signaling pathway are also individually or collectively beneficial to productivity of such fungal strains. Suitable other components of this signaling pathway include, without limitation, MAP kinase proteins and transcription factors that regulate expression of other genes in response to osmotic pressure.

Strains with mutations in this pathway can be identified by screening for resistance or sensitivity to osmotic stress, such as, for example, in the presence of high levels of sorbitol or salt in the medium.

In some embodiments, the parental strain of the engineered fungal strain of this aspect is an Ascomycete fungal strain. In particular embodiments, the parental strain is a filamentous fungal strain.

Suitable osmotic agents may include one or a combination of sugars, sugar alcohols or salts. For example, the osmotic agent may be one or more of glucose, sucrose, fructose, oligofructose, fructo-oligosaccharide, inverted sugar, sorbitol, xylitol, galactosylosorbitol, sodium chloride or potassium chloride.

BRIEF DESCRIPTION OF THE DRAWINGS

FIG. 3A depicts the colony phenotype of RLP37 Nik1$^{M743T}$ on Vogel's minimal medium. FIG. 3B depicts the colony phenotype of RLP37 on Vogel's minimal medium. FIG. 3C depicts the colony phenotype of RLP37 Nik1$^{M743T}$ on Vogel's minimal medium with sorbitol. 3D depicts the colony phenotype of RLP37 on Vogel's minimal medium with sorbitol. FIG. 3E depicts the colony phenotype of RLP37 ΔNik1 on Vogel's minimal medium. FIG. 3F depicts the colony phenotype of RLP37 ΔNik1 on Vogel's minimal medium with sorbitol.

FIG. 4A depicts the specific total protein production rate of RLP37 and RLP37 Nik1$^{M743T}$. FIG. 4B depicts the specific yield on fed sugars of RLP37 and RLP37 Nik1$^{M743T}$, during fermentation under the same conditions.

FIG. 5A depicts the specific total protein production rate of RLP37 and RLP37 Nik1$^{M743T}$. FIG. 5B depicts the specific yield on fed sugars of RLP37 and RLP37 Nik1$^{M743T}$, during fermentation under the same conditions.

FIG. 7A depicts the specific total protein production rate of RLP37 and RLP37 ΔNik1. FIG. 7B depicts the specific yield on fed sugars of RLP37 and RLP37 ΔNik1, during fermentation under the same conditions.

FIG. 8A depicts the colony phenotype of NoCbh1 Nik1$^{M743T}$ on Vogel's minimal medium with uridine. FIG. 8B depicts the colony phenotype of NoCbh1 on Vogel's minimal medium with uridine. FIG. 8C depicts the colony phenotype of NoCbh1 Nik1$^{M743T}$ on Vogel's minimal medium with uridine and sorbitol. FIG. 8D depicts the colony phenotype of NoCbh1 on Vogel's minimal medium with uridine and sorbitol. FIG. 8E depicts the colony phenotype of Cbh1 Nik1$^{M743T}$ on Vogel's minimal medium with uridine. FIG. 8F depicts the colony phenotype of Cbh1 on Vogel's minimal medium with uridine. FIG. 8G depicts the colony phenotype of Cbh1 Nik1$^{M743T}$ on Vogel's minimal medium with uridine and sorbitol. FIG. 8H depicts the colony phenotype of Cbh1 on Vogel's minimal medium with uridine and sorbitol. FIG. 8I depicts the colony phenotype of TR Nik1$^{WT}$ on Vogel's minimal medium. FIG. 8J depicts the colony phenotype of TR Nik1$^{M743T}$ on Vogel's minimal medium. FIG. 8K depicts the colony phenotype of TR Nik1$^{WT}$ on Vogel's minimal medium with sorbitol. FIG. 8L depicts the colony phenotype of TR Nik1$^{M743T}$ on Vogel's minimal medium with sorbitol.

FIG. 9A depicts the specific total protein production rate of Cbh1 and Cbh1 Nik1$^{M743T}$ FIG. B depicts the specific yield on fed sugars of Cbh1 and Cbh1 Nik1$^{M743T}$ during fermentation under the same conditions.

FIG. 10A depicts the specific total protein production rate of Cbh1 and Cbh1 Nik1$^{M743T}$ FIG. 10B depicts the specific yield on fed sugars of Cbh1 and Cbh1 Nik1$^{M743T}$ during fermentation under the same conditions.

FIG. 12A depicts the specific total protein production rate of RLP37, TR Nik1$^{M743T}$ and TR Nik1$^{WT}$. FIG. 12B depicts the specific yield on fed sugars of RLP37, TR Nik1$^{M743T}$ and TR Nik1$^{WT}$, during fermentation under the same conditions.

FIG. 13A RLP37 on Vogel's minimal medium, FIG. 13B RLP37 Nik1$^{M743T}$ on Vogel's minimal medium, FIG. 13C RLP37 on Vogel's minimal medium with 0.15% DMSO, FIG. 13D RLP37 Nik1$^{M743T}$ on Vogel's minimal medium with 0.15% DMSO, FIG. 13E RLP37 on Vogel's minimal medium with 45 µM iprodione, FIG. 13F RLP37 Nik1$^{M743T}$ on Vogel's minimal medium with 45 µM iprodione.

DETAILED DESCRIPTION OF THE INVENTION

I. Overview

Figure 1:
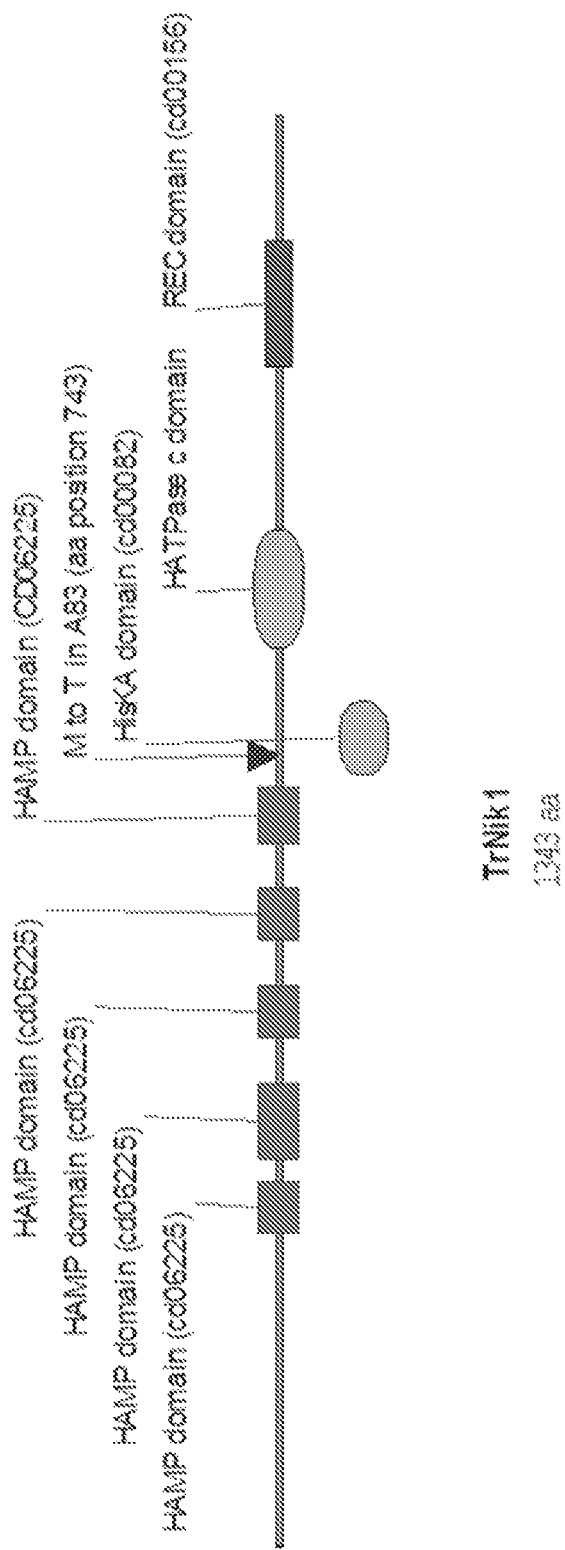
FIG. 1. Depicts a schematic diagram of domain architecture of TrNik-1.

The present strains and methods relate to a variant or mutant filamentous fungus cell having been genetically modified from its wild type parental filamentous fungal cell to comprise a variant histidine kinase gene and/or express a variant histidine kinase encoded by the variant histidine kinase gene, wherein the cell's histidine kinase mediated signal transduction mechanism is substantially altered or eliminated. Such strains are well suited for large scale production of proteins of interest at improved productivity levels.

II. Definitions

Prior to describing the present strains, compositions and methods, the following terms and phrases are defined. Terms not defined should be accorded their ordinary meaning as used in the art.

Where a range of values is provided, it is understood that each intervening value, to the tenth of the unit of the lower limit unless the context clearly dictates otherwise, between the upper and lower limit of that range and any other stated or intervening value in that stated range, is encompassed within the present compositions and methods. The upper and lower limits of these smaller ranges may independently be included in the smaller ranges and are also encompassed within the present compositions and methods, subject to any specifically excluded limit in the stated range. Where the stated range includes one or both of the limits, ranges excluding either or both of those included limits are also included in the present compositions and methods.

Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number. For example, in connection with a numerical value, the term "about" refers to a range of −10% to +10% of the numerical value, unless the term is otherwise specifically defined in context. In another example, the phrase a "pH value of about 6" refers to pH values of from 5.4 to 6.6, unless the pH value is specifically defined otherwise.

The headings provided herein are not limitations of the various aspects or embodiments of the present compositions and methods which can be had by reference to the specification as a whole. Accordingly, the terms defined immediately below are more fully defined by reference to the specification as a whole.

The present document is organized into a number of sections for ease of reading; however, the reader will appreciate that statements made in one section may apply to other sections. In this manner, the headings used for different sections of the disclosure should not be construed as limiting.

Unless defined otherwise, all technical and scientific terms used herein have the same meaning as commonly understood by one of ordinary skill in the art to which the present compositions and methods belongs. Although any methods and materials similar or equivalent to those described herein can also be used in the practice or testing of the present compositions and methods, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present compositions and methods are not entitled to antedate such publication by virtue of prior invention. Further, the dates of publication provided may be different from the actual publication dates which may need to be independently confirmed.

In accordance with this detailed description, the following abbreviations and definitions apply. Note that the singular forms "a," "an," and "the" include plural referents unless the context clearly dictates otherwise. Thus, for example, reference to "an enzyme" includes a plurality of such enzymes, and reference to "the dosage" includes reference to one or more dosages and equivalents thereof known to those skilled in the art, and so forth.

It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

It is further noted that the term "consisting essentially of," as used herein refers to a composition wherein the component(s) after the term is in the presence of other known component(s) in a total amount that is less than 30% by weight of the total composition and do not contribute to or interferes with the actions or activities of the component(s).

It is further noted that the term "comprising," as used herein, means including, but not limited to, the component(s) after the term "comprising." The component(s) after the term "comprising" are required or mandatory, but the composition comprising the component(s) may further include other non-mandatory or optional component(s).

It is also noted that the term "consisting of," as used herein, means including, and limited to, the component(s) after the term "consisting of." The component(s) after the term "consisting of" are therefore required or mandatory, and no other component(s) are present in the composition.

As will be apparent to those of skill in the art upon reading this disclosure, each of the individual embodiments described and illustrated herein has discrete components and features which may be readily separated from or combined with the features of any of the other several embodiments without departing from the scope or spirit of the present compositions and methods described herein. Any recited method can be carried out in the order of events recited or in any other order which is logically possible.

As used herein, the term "protein of interest" refers to a polypeptide that is desired to be expressed in a filamentous fungus, optionally at high levels and for the purpose of commercialization. Such a protein may be an enzyme, a substrate-binding protein, a surface-active protein, a structural protein, or the like.

As used herein, the terms "polypeptide" and "protein" are used interchangeably to refer to polymers of any length comprising amino acid residues linked by peptide bonds. The conventional one-letter or three-letter codes for amino acid residues are used herein. The polymer may be linear or branched, it may comprise modified amino acids, and it may be interrupted by non-amino acids. The terms also encompass an amino acid polymer that has been modified naturally or by intervention; for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, unnatural amino acids, etc.), as well as other modifications known in the art.

As used herein, "variant," when used in conjunction with a polypeptide, refers to a polypeptide that is derived from a parent (or reference) polypeptide by the substitution, addition, or deletion, of one or more amino acids, typically by applying recombinant DNA techniques. Variant polypeptides may differ from a parent polypeptide by one or more, or a few (e.g., 1, 2, 3, 4, 5, 6, 7, 8, 9, 10, or more) amino acid residues. Variant polypeptides may be defined by their level of primary amino acid sequence homology/identity with a parent polypeptide. Preferably, variant polypeptides have at least about 50%, at least about 55%, at least about 60%, at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, or even at least about 99% amino acid sequence identity with a parent or reference polypeptide. A variant polypeptide typically does not comprise an amino acid sequence that is 100% identical to that of a parent/reference polypeptide.

The term "variant," when used in conjunction with a polynucleotide or a gene, refers to a polynucleotide having a specified degree of homology/identity to a parent or reference polynucleotide or gene, or is capable of hybridizing under stringent conditions to a parent or reference polynucleotide or gene sequence, or the complement thereof. For instance, a variant polynucleotide can suitably have at least about 50%, at least about 55%, at least about 60%, at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, or even at least about 99% nucleotide sequence identity with a parent polynucleotide. A variant polynucleotide or gene typically does not comprise a nucleotide sequence that is 100% identical to that of a parent/reference polynucleotide or gene.

As used herein, the term "histidine kinase" refers to a signaling factor that exists in bacteria, yeasts, filamentous fungi and plants, which mediates histidine phosphorylation. Histidine kinases are mostly transmembrane receptors, a substantial minority of these are soluble cytoplasmic proteins. In either form, these kinases are modular with highly conserved catalytic transmitter regions linked to diverse sensory domains. A receptor histidine kinase links its sensory domain to its cytoplasmic transmitter region through a transmembrane domain. The transmitter region consists of two domains: an N-terminal DHp (dimerization and histidine phosphotransfer) domain and a C-terminal CA (catalytic and ATP-binding) domain (Stock, A. M., et al. Ann. Rev. Biochem. (2000) 69:183-215). Histidine kinases function as homodimers, with a few exceptions, and their dimerization is mediated by the DHp domain, which forms a four-helix bundle (Goodman et al., Genes Dev. (2009) 23:249-59).

As used herein, the term "hybrid-type histidine kinase" is a type of histidine kinase, in which the histidine kinase domain and the response regulator domain are present in the same proteins. In a yeast *Saccharomyces cerevisiae*, only one hybrid-type histidine kinase gene (SLN1) exists in the genome (Ota, I. M., et al., Science (1993) 262, 566-569.). In yeast, Sln1 is involved in a high-osmolarity response. This response involves accumulation of glycerol as the primary compatible solute in the cells (Posas, F., et al., Cell (1996) 86, 865-875). In a plant *Arabidopsis thaliana*, nine hybrid type and three conventional histidine kinase genes exist in the genome, and 2 of the 12 histidine kinase genes can complement yeast sln1 mutants (Reiser, V., et al. J. Cell Biol. (2003) 161, 1035-1040). *Aspergillus nidulans* also has an SLN1-homolog that can complement a yeast sln1 mutant (Furukawa, K., et al., Appl. Environ. Microbiol. (2002) 68, 5304-5310). In the filamentous fungus *Neurospora crassa*, a hybrid-type histidine kinase Os-1/Nik-1 that is different from Sln1-homolog is involved in the os (osmosensitive) signal transduction pathway and is needed for adaptation to high osmolarity conditions (Alex, L. A., et al., Proc. Natl. Acad. Sci. USA (1996) 93, 3416-3421).

As used herein, the term "group III histidine kinases" refers to a histidine kinase having a unique N-terminal region consisting of HAMP domain repeats, which are found in signaling-related proteins, including histidine kinases, adenylyl cyclases, methyl-accepting chemotaxis proteins, and phosphatases (Aravind L, Ponting C P. FEMS Microbiol Lett (1999)176: 111-116). For example, *N. crassa* Os-1p (also known as Nik1p), *B. fuckeliana* Daf1p (also known as BcOs1p), and *C. heterostrophus* Dic1p (also known as ChNik1p), are characterized by a unique N-terminal region consisting of a HAMP domain repeat (Catlett, N. L., et al. Cell (2003) 2, 1151-1161). The phylogenetic analysis revealed 11 major groups of euascomycete (*C. heterostrophus, G. moniliformis, N. crassa*, and *B. fuckeliana*) histidine kinases. Many of these groups contain histidine kinases that are highly conserved in filamentous ascomycetes. Other groups are more divergent, containing gene families that have expanded within species and few clear orthologs between species. These groupings suggest that some histidine kinase genes are necessary for basic functions shared by most or all ascomycetes (e.g., osmosensing), while others may have evolved to adapt to specific aspects of the lifestyle of a pathogen. The precise function of these domains is unknown; however, mutations in the NIK1 HAMP repeat region are responsible for the most severe osmosensitivity and dicarboximide resistance phenotypes (Miller, T. K., et al., Fungal Genet. Biol. (2002) 35:147-155.)

As used herein, the term "fungus" refers to any member of a large group of eukaryotic organisms that includes microorganisms such as yeasts and molds, as well as the mushrooms. These organisms are classified as a kingdom, Fungi, which are separate and distinct from plants, animals, protists, and bacteria. One primary difference is that fungal cells have cell walls that contain chitin, unlike the cell walls of plants and some protists, which contain cellulose, and unlike the cell walls of bacteria.

As used herein, the term "Ascomycete fungal strain" refers to any organism in the Division Ascomycota in the Kingdom Fungi. Examples of Ascomycetes fungal cells include but are not limited to filamentous fungi in the subphylum Pezizomycotina, such as *Trichoderma* spp, *Aspergillus* spp, *Myceliophthora* spp, and *Penicillium* spp.

As used herein, the term "filamentous fungus" refers to all filamentous forms of the subdivision Eumycota and Oomycota. For example, filamentous fungi include, without limitation, *Acremonium, Aspergillus, Emericella, Fusarium, Humicola, Mucor, Myceliophthora, Neurospora, Scytalidium, Thielavia, Tolypocladium*, or *Trichoderma* species. In some embodiments, the filamentous fungus may be an *Aspergillus aculeatus, Aspergillus awamori, Aspergillus foetidus, Aspergillus japonicus, Aspergillus nidulans, Aspergillus niger*, or *Aspergillus oryzae*. In some embodiments, the filamentous fungus is a *Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides*, or *Fusarium venenatum*. In some embodiments, the filamentous fungus is a *Humicola insolens, Humicola lanuginosa, Mucor miehei, Myceliophthora thermophila, Neurospora crassa, Scytalidium thermophilum*, or *Thielavia terrestris*. In some embodiments, filamentous fungus is a *Trichoderma harzianum, Trichoderma koningii, Trichoderma longibrachiatum, Trichoderma reesei*, e.g., RL-P37 (Sheir-Neiss et al., Appl. Microbiol. Biotechnology, 20 (1984) pp. 46-53; Montenecourt B. S., Can., 1-20, 1987), QM9414 (ATCC No. 26921), NRRL 15709, ATCC 13631, 56764, 56466, 56767, or *Trichoderma viride*, e.g., ATCC 32098 and 32086. In some embodiments, the filamentous fungus is a *Trichoderma reesei* RutC30, which is available from the American Type Culture Collection as *Trichoderma reesei* ATCC 56765. Related to this, in some embodiments, the disclosure provides a whole cell broth preparation of any one of the filamentous fungi described herein.

A "heterologous" nucleic acid construct or sequence has a portion of the sequence which is not native or existing in a native form to the cell in which it is expressed. Heterologous, with respect to a control sequence refers to a control sequence (i.e. promoter or enhancer) that does not function in nature to regulate the same gene the expression of which it is currently regulating. Generally, heterologous nucleic acid sequences are not endogenous to the cell or part of the genome in which they are present, and have been added to the cell, by infection, transfection, transformation, microinjection, electroporation, or the like. A "heterologous" nucleic acid construct may contain a control sequence/DNA coding sequence combination that is the same as, or different from a control sequence/DNA coding sequence combination found in the native cell.

The term "host cell", as used herein, may suitably be a cell of any fungus, whether a unicellular organism, a cell derived from a multicellular organism and placed in tissue culture or a cell present as part of a multicellular organism, which is susceptible to transformation with a nucleic acid construct according to the invention. Host cells such as yeast and other fungal cells may be used for replicating DNA and producing polypeptides encoded by nucleotide sequences as used in the invention. Suitable cells are generally filamentous fungi or yeasts. Particularly preferred are cells from filamentous fungi, preferably cells from *Aspergillus*, such as *A. niger* and *A. tubingensis*. Other preferred organisms include *Aspergillus oryzae, A. awamori, Myceliophthora thermophile, Trichoderma reesei, T. viride* or *T. longibrachiatum*.

As used herein, the term "vector" refers to a nucleic acid construct designed for transfer between different host cells. An "expression vector" refers to a vector that has the ability to incorporate and express heterologous DNA fragments in a foreign cell. Many prokaryotic and eukaryotic expression vectors are commercially available. Selection of appropriate expression vectors is within the knowledge of those having skill in the art.

As used herein, the term "engineered fungal strain" refers to a fungal strain constructed using genetic engineering technology.

As used herein, the term "parental strain" refers to a microorganism strain the genome of which can be mutated once, twice, or more times, to generate an engineered strain.

As used herein, the term "transformed" refers to a cell has been transformed by the use of recombinant DNA techniques. Transformation typically occurs by insertion of one or more nucleotide sequences into a cell. The inserted nucleotide sequence may be a heterologous nucleotide sequence, i.e., is a sequence that is not natural to the cell that is to be transformed, such as a fusion protein.

The term "derived" encompasses the terms "originated" "obtained," "obtainable," and "created," and generally indicates that one specified material find its origin in another specified material or has features that can be described with reference to the another specified material.

As used herein, the term "gene" means the segment of DNA involved in producing a polypeptide, that may or may not include regions preceding and following the coding region, e.g. 5' untranslated (5' UTR) or "leader" sequences and 3' UTR or "trailer" sequences, as well as intervening sequences (introns) between individual coding segments (exons). In certain embodiments, a gene may suitably encode certain commercially important industrial proteins or peptides, such as enzymes, e.g., proteases, mannanases, xylanases, amylases, glucoamylases, cellulases, oxidases or lipases. A gene of interest may be a naturally occurring gene, a mutated gene or a synthetic gene.

As used herein, the term "mutation" refers to any change or alteration in a nucleic acid sequence. Several types of mutation exist, including point, frame shift, and splicing mutations. Mutation may be performed specifically (e.g. site directed mutagenesis) or randomly (e.g. via chemical agents, passage through repair minus bacterial strains).

As used herein, the term "improving the protein production" refers to a protein production process whereby the amount of protein produced from that process is increased. The protein thus produced may be produced into the culture medium or within the host cell, however, the former is preferred. Increased production may be detected for example as higher maximal level of protein or enzymatic activity, such as cellulase or hemicellulase activity, or total extracellular protein produced as compared to the parent host organism.

As used herein, the term "specific productivity" refers to total amount of protein produced per cell per time over a given time period.

As used herein, the term "% identity" is used interchangeably with the term "% homology," and both refer to the level of nucleic acid or amino acid sequence identity between the nucleic acid sequences that encode any one of the inventive polypeptides or the inventive polypeptide's amino acid sequences, when aligned using a sequence alignment program.

III. Engineered Fungal Strain Having Improved Protein Production

The present disclosure relates, in a first aspect, to an engineered, transformed or derivative fungal strain capable of producing an altered level of a protein of interest, and in a second aspect, to methods of genetically modifying a fungal strain such that it has an ability to produce an altered level of protein of interest. Moreover, the present disclosure pertains to a protein of interest produced by fermenting such engineered, transformed or derivative fungal strain, and further, pertains to a composition comprising the protein of interest thus produced. Furthermore, the present disclosure pertains to a method of producing a protein of interest employing an engineered, transformed or derivative fungal strain, as well as a method of producing and using a composition comprising the protein of interest. The present disclosure also relates to a method for identifying or selecting for an engineered fungal strain capable of producing an altered level of a protein of interest as compared to a parental strain.

In a first aspect, the present disclosure provides an engineered fungal strain, capable of producing an altered level of a protein of interest as compared to a parental strain, wherein the fungal strain comprises a variant histidine kinase gene and/or is capable of expressing a variant histidine kinase. In some embodiments, the present disclosure provides an engineered fungal strain capable of producing a significantly greater quantity of a protein of interest as compared to its parental strain. For example, the engineered fungal strain is capable of producing at least about 5%, at least about 10%, at least about 20%, at least about 50%, at least about 75%, at least about 100%, or even at least about 150% greater amounts of a protein of interest as compared to its parental strain.

In a second aspect, the present disclosure provides a transformed fungal strain or derivative fungal strain thereof, capable of producing an altered level of a protein of interest as compared to a parental strain, wherein the transformed fungal strain or the derivative fungal strain comprises a variant histidine kinase gene and/or is capable of expressing a variant histidine kinase gene.

In a third aspect, the present disclosure provides a method for improving protein production by an engineered, transformed, or derivative fungal strain, as compared to its native, unengineered, untransformed, or non-derivative parental strain, the method comprising employing an engineered, transformed or derivative fungal strain, wherein the engineered, transformed or derivative fungal strain comprises a variant histidine kinase gene and/or is capable of expressing a variant histidine kinase.

In any of the aspects presented herein, the variant histidine kinase is a variant of a wild type histidine kinase. In some embodiments, the variant histidine kinase comprises a polypeptide or amino acid sequence that is at least about 60% (e.g., at least about 60%, at least about 65%, at least about 70%, at least about 75%, at least about 80%, at least about 85%, at least about 90%, at least about 95%, at least about 96%, at least about 97%, at least about 98%, at least about 99%, or even higher %) identical to SEQ ID NO:1, but is not 100% identical to SEQ ID NO:1. In other embodiments, the variant histidine kinase comprises a polypeptide or amino acid sequence that is at least about 60% (e.g., at least about 60%, at least about 65%, at least about 70%, at least about 75%, at least about 80%, at least about 85%, at least about 90%, at least about 95%, at least about 96%, at least about 97%, at least about 98%, at least about 99%, or even higher %) identical to SEQ ID NO: 43, but is not 100% identical to SEQ ID NO: 43. For instance, the variant histidine kinase is suitably one encoded by a variant histidine kinase gene, wherein the variant histidine kinase comprises an amino acid sequence that is at least about 60% (e.g., at least about 60%, at least about 65%, at least about 70%, at least about 75%, at least about 80%, at least about 85%, at least about 90%, at least about 95%, at least about 96%, at least about 97%, at least about 98%, at least about 99%, or even higher %) identical to SEQ ID NO: 1, and a mutation at position 743 of SEQ ID NO: 1 or SEQ ID NO: 43 and a mutation at position 786 of SEQ ID NO: 43.

A. Histidine Kinase

Histidine kinase is a sensor protein, which can detect and transform external signals into transducible cellular events. Detection of external stimuli and the transfer of these signals within the cell to give an appropriate response are vital for organisms in order to adapt to varying environmental conditions during their life cycles. Signaling mechanisms are found in all living cells as two component systems or as phosphorelay systems in more complex organisms. Such systems confer signal transfer of a phosphoryl group from an, often membrane bound, histidine kinase to a response regulator protein and thus trigger various physiological responses. Phosphorylation can promote oligomerization (Weiss, V., F. Claverie-Martin, and B. Magasanik. Proc. Natl. Acad. Sci. USA (1992) 89:5088-5092; Webber, C. A., and R. J. Kadner. Mol. Microbiol. (1997) 24:1039-1048), dimerization (Cobb, M. H., and E. J. Goldsmith. Trends Biochem. Sci. (2000) 25:7-9), interactions with other proteins (Blat, Y., and M. Eisenbach. Biochemistry (1994) 33:902-906; Newton, A. C. Chem. Rev. (2001) 101:2353-2364), interactions with DNA (Aiba, H., F. Nakasai, S. Mizushima, and T. Mizuno. J. Biochem. (1989) 106:5-7), or combinations of these mechanisms (Harlocker, S. L., L. Bergstrom, and M. Inouye. J. Biol. Chem. (1995) 270:26849-26856). Phosphorelay systems have been implicated in regulating differentiation processes, chemotaxis, secondary metabolite production, and virulence-associated processes in pathogenic and nonpathogenic bacteria and fungi (Grebe, T. W., and J. B. Stock. Adv. Microb. Physiol. (1999) 41:139-227; Wolanin, P. M., P. A. Thomason, and J. B. Stock. Genome Biol. (2002) 3: Reviews 3013).

Hybrid-type histidine kinase, phosphorelay signaling systems, consisting of two components as basic signaling factors: autophosphorylating histidine kinase and a response regulator that receives phosphoric acid therefrom to send the information to the downstream region, are involved in several signal transduction pathways in plants, slime molds, fungi, and bacteria, but not in animals (Catlett, N. L., et al. Cell (2003) 2, 1151-1161). They play pivotal roles in responses to environmental stimuli and regulate various processes, including virulence in plant and animal pathogens (Wolanin, P. M., P. A. Thomason, and J. B. Stock. 2002. Genome Biol. (2002) 3: Reviews 3013).

In fungi, histidine kinases are classified into 11 groups (Catlett, N. L., et al. Cell (2003) 2, 1151-1161). Typically, the hybrid-type histidine kinase genes contain in addition to the HisKA domain, a REC (signal receiver) domain (PF00072), a HATPase (histidine-like ATPase; PF02518) domain, and different signaling domains, for example, HAMP-(histidine kinase, adenylyl cyclase, methyl-accepting protein, and phosphatase; PF00672), and ATPase domains (PF13191). Group III histidine kinases, have a unique N-terminal region consisting of HAMP domain repeats, which are found in signaling-related proteins, including HKs, adenylyl cyclases, methyl-accepting chemotaxis proteins, and phosphatases (Aravind L, Ponting C P. FEMS Microbiol Lett (1999)176: 111-116).

The group III histidine kinases were known as mediators of environmental stress responses, pathogenicity, hyphal development, and sporulation (Li, S., et al. EMBO J. (1998) 17:6952-6962.; Hohmann, S. Mol. Biol. Rev. (2002) 66:300-372.; Nemecek, J. C., et al. Science (2006) 312:583-588.; Viaud, M., et al. Mol. Plant Microbe Interact. (2006) 19:1042-1050; Islas-Flores, et al. Asian J. Biochem. (2011) 6:1-14.). The mutation of these histidine kinase genes resulted in resistance to phenylpyrrole and dicarboximide fungicides and also in increased osmosensitivity (Cui, W.; Beever, R. E., Parkes, S. L., Weeds, P. L. & Templeton, M. D. Fungal Genet. Biol. (2002), 36, 187-198; Ochiai, N.; Fujimura, M., Motoyama, T., Ichiishi, A., Usami, R., Horikoshi, K. & Yamaguchi, I. Pest. Manag. Sci., (2001) 57, 437-442). In *C. heterostrophus*, null mutants for dic1 and mutants with a deletion or point mutation in the HAMP domain repeat were highly sensitive to osmotic stress and highly resistant to the previously mentioned fungicides (Yoshimi A, Tsuda M, Tanaka C Mol Genet Gennomics (2004) 271: 228-236). Similar effects resulting from mutations were observed in *N. crassa* os-1 and *B. fuckeliana* daf1 (Cui, W.; Beever, R. E., Parkes, S. L., Weeds, P. L. & Templeton, M. D. Fungal Genet. Biol. (2002), 36, 187-198; Ochiai, N.; Fujimura, M., Motoyama, T., Ichiishi, A., Usami, R., Horikoshi, K. & Yamaguchi, I. Pest. Manag. Sci., (2001) 57, 437-442). A single amino acid change within the kinase domain or the regulator domain of *C. heterostrophus* dic1 altered the sensitivity to osmotic stress and conferred a moderate resistance to the fungicides. Thus, the group III histidine kinase is considered to be a putative osmosensor (Schumacher, M. et al., CURR MICROBIOL (1997) 34, 340-347). Furthermore, members of group III histidine kinases are believed to be the target of commercial pesticides such as fludioxonil, iprodione, and the antifungal natural product ambruticin (Motoyama, T.; Ohira, T., Kadokura, K., Ichiishi, A., Fujimura, M., Yamaguchi, I. & Kubo, T. Curr. Genet., (2005b) 47, 298-306; Dongo A, Bataillé-Simoneau N, Campion C, Guillemette T, Hamon B, et al. Appl, Environ. Microbiol. (2009) 75: 127-134).

In one example, the domain architecture of *T. reesei* histidine kinase gene (TrNik-1) was analyzed by bioinformatics in this present disclosure, and it was shown that TrNik-1 contains 5 HAMP functional domains, 1 HisKA functional domain, 1 HATPase domain and 1 REC functional domain (FIG. 1). According to the domain architecture, TrNik-1 belongs to group III histidine kinase. The amino acid or polypeptide sequence of *Trichoderma reesei* histidine kinase (TrNik1) is presented herein below as SEQ ID NO:1:

```
MIEDTAALAAAAELIASLACDPASASASSSLVSVGPGSSIKLPGRENPA

KRTLEIELEKLVLRISQLESRASASANASVFPETPNEVNDTLFNDDVDP

SVNGRPPLTKEALQGLRDHVDDQSKLLDSQRQELAGVNAQLLEQKQLQE

RALAMLEQERVATLERELWKHQKANEAFQKALREIGEIVTAVARGDLTM

KVRMNSVEMDPEITTFKRTINAMMDQLQTFASEVSRVAREVGTEGLLGG

QARIGGVDGVWKELTDNVNIMAQNLTDQVREIASVTTAVAHGDLTKKIE

RPAKGEILQLQQTINTMVDQLRTFASEVTRVARDVGTEGILGGQADVGG

VKGMWNDLTVNVNAMANNLTTQVRDIIKVTTAVAKGDLTQKVQAECRGE

MFKLKSTINSMVDQLQQFAREVTKIAREVGTEGRLGGQATVHDVEGTWR

DLTENVNGMAMNLTTQVREIAKVTTAVARGDLTKKIGVEVKGEILELKN

TINQMVDRLGTFAVEVSKVAREVGTDGTLGGQAQVANVEGKWKDLTENV

NTMASNLTVQVRSISAVTQAIANGDMSQTIDVEANGEIQVLKETINNMV

SRLSSFCYEVQRVAKDVGVDGKMGAQADVAGLNGRWKEITTDVNTMASN

LTTQVRAFSDITNLATDGDFTKLVDVEASGEMDELKKKINQMISNLRDS

IQRNTQAREAAELANKTKSEFLANMSHEIRTPMNGIIGMTQLTLDTDLT

QYQREMLNIVNDLANSLLTIIDDILDLSKIEARRMVIEEIPYTLRGTVF
```

-continued

```
NALKTLAVKANEKFLDLTYKVDSSVPDYVIGDSFRLRQIILNLVGNAIK

FTEHGEVSLTIQEQEDKRHVGPGEYAIEFIVEDTGIGIAKDKLNLIFDT

FQQADGSMTRKFGGTGLGLSISKRFVNLMGGDLWVNSEVGKGSEFHFTC

RVKLADVHAESVQQQLKPYRGHQVLFVDKSQSNAATHIGEMLEEIGLHP

VVVNSEKSSALTRLKEGGALPYDAIIVDSIDTARRLRAVDDFKYLPIVL

LAPVVHVSLKSCLDLGITSYMTMPCKLIDLSNGMIPALENRATPSLADV

TKSFEILLAEDNTVNQKLAVKILEKYHHVVTVVGNGWEAVEAVKQKKFD

VILMDVQMPIMGGFEATGKIREYERGMGTHRTPIIALTAHAMMGDREKC

IQAQMDEYLSKPLQQNQLIQTILKCATLGGALLEKNRERELALQAEAKA

YQDLPY
```

The amino acid or polypeptide sequence of *Aspergillus niger* histidine kinase (AnNik1) is presented herein below as SEQ ID NO: 43:

```
MAGADETLAAAAAILRGLAKETPSSSAPPFDFEFSHPPANGYDTKLAKL

PGETSSAKAAFEQELEALVRRVRHLEFQNVSHHQSTPKSSQSSLTPGEK

DADFLWSFGLSRVSSRDGSDSCLSQHQKTTQQQQQQPHGSRRSAIEPE

DHEVEEDIDDEESDEDEELNSRTRLVREEDISYLRNHVQKQAEEISFQK

DIIAQVRDELQQQEEQTRRALTKVENEDVVLLERELRKHQQANEAFQKA

LREIGGIITQVANGDLSMKVQIHPLEMDPEIATFKRTINTMMDQLQVFG

SEVSRVAREVGTEGILGGQAQITGVHGIWKELTENVNIMAKNLTDQVRE

IAAVTTAVAHGDLSQKIESRAQGEILELQQTINTMVDQLRTFATEVTRV

ARDVGTEGVLGGQAQIEGVQGMWNELTVNVNAMANNLTTQVRDIATVTK

AVAKGDLTQKVQANCKGEIAELKNIINSMVDQLRQFAQEVTKIAKEVGT

DGVLGGQATVNDVEGTWKDLTENVNRMANNLTTQVREIADVTTAVAKGD

LTKKVTANVQGEILDLKSTINGMVDRLNTFAFEVSKVAREVGTDGTLGG

QAKVDNVEGKWKDLTDNVNTMAQNLTSQVRSISDVTQAIAKGDLSKKIE

VHAQGEILTLKVTINHMVDRLAKFATELKKVARDVGVDGKMGGQANVEG

IAGTWKEITEDVNTMAENLTSQVRAFGEITDAATDGDFTKLITVNASGE

MDELKRKINKMVSNLRDSIQRNTAAREAAELANRTKSEFLANMSHEIRT

PMNGIIGMTQLTLDTDDLKPYTREMLNVVHNLANSLLTIIDDILDISKI

EANRMVIESIPFTVRGTVFNALKTLAVKANEKFLSLTYQVDNTVPDYVI

GDPFRLRQIILNLVGNAIKFTEHGEVKLTICKSDREQCAADEYAFEFSV

SDTGIGIEEDKLDLIFDTFQQADGSTTRRFGGTGLGLSISKRLVNLMGG

DVWVTSEYGHGSTFHFTCVVKLADQSLSVIASQLLPYKNHRVLFIDKGE

NGGQAENVMKMLKQIDLEPLVVRNEDHVPPPEIQDPSGKESGHAYDVII

VDSVATARLLRTFDDFKYVPIVLVCPLVCVSLKSALDLGISSYMTTPCQ

PIDLGNGMLPALEGRSTPITTDHSRSFDILLAEDNDVNQKLAVKILEKH

NHNVSVVSNGLEAVEAVKQRRYDVILMDVQMPVMGGFEATGKIREYERE

SGLSRTPIIALTAHAMLGDREKCIQAQMDEYLSKPLKQNQMMQTILKCA

TLGGSLLEKSKESRISSSGEMHPVHHSGPDGKSQQRPGLEPRSVTATST

INRGGGLASPNVDRADELAVERALLRSNSS
```

B. Engineered Fungal Strain Comprising a Mutated or Knocked Out Histidine Kinase In one embodiment, the modification of the *Trichoderma reesei* native nik1 histidine kinase allele can cause an increase in the amount of secreted proteins. The nik1 modification was a single nucleotide T to C substitution in the open reading frame (ORF) (SEQ ID NO:1) that changes the amino acid at position 743 of the Nik1 protein from Met (ATG) to Thr (ACG).

Figure 4A:
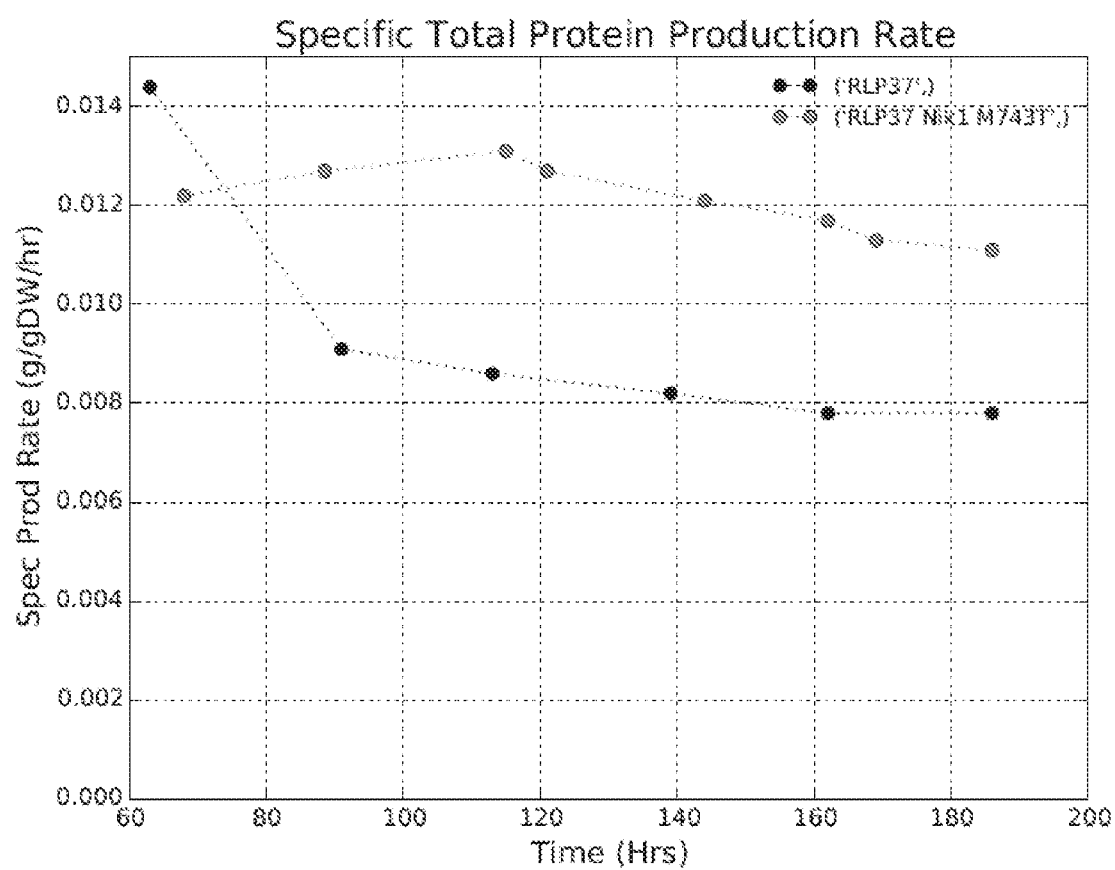
FIGS. 4A-4B. Compares the protein production of RLP37 and RLP37 Nik1$^{M743T}$ in DASGIP 2 L scale fermentation.

The comparison of the protein production of a strain containing the modified nik1$^{M743T}$ histidine kinase allele with the host strain containing the nik1 wild type (native) allele has been carried out, and it was found that the specific total protein production rate and yield on fed sugars of RLP37 Nik1$^{M743T}$ showed a significant improvement over RLP37 (FIG. 4). This indicated that introducing the modified nik1 histidine kinase into a host *T. reesei* strain causes an increase in protein production.

In other embodiments, the modification of the *Aspergillus niger* native nik1 histidine kinase allele can cause an increase in the amount of secreted proteins. The nik1 modification was a single nucleotide T to C substitution in the open reading frame (ORF) (SEQ ID NO: 43) that changes the amino acid at position 786 of the Nik1 protein from Met (ATG) to Thr (ACG).

Figure 15:
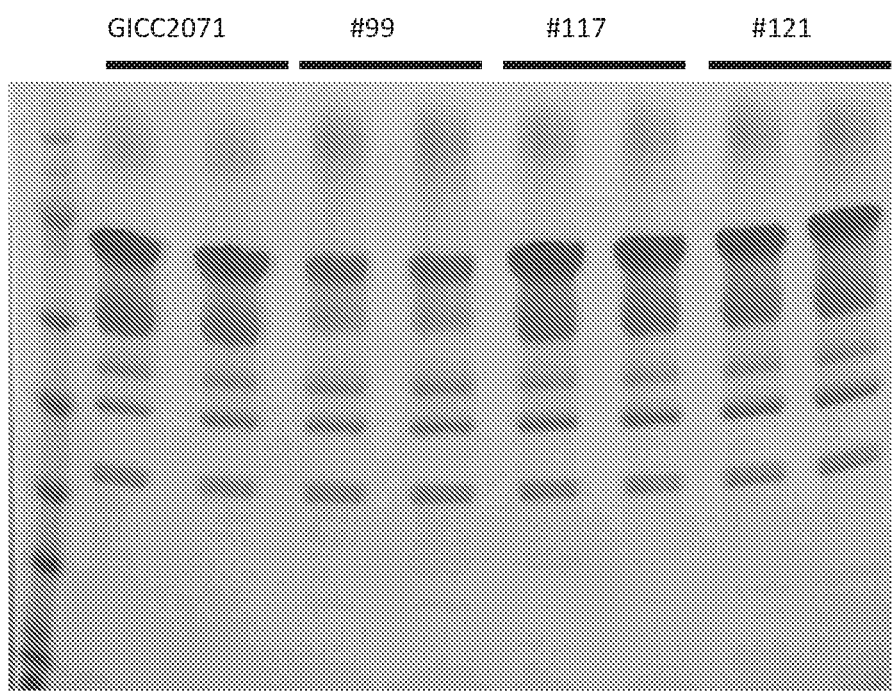
FIG. 15. Compares the protein production of strain GICC2071 containing the wild-type nik1 allele (control), and GICC2071 Nik1$^{M786T}$ mutant strains #99, 117, and 121, containing the nik1$^{M786T}$ allele, at shake flask scale. Supernatants from shake flasks were run on SDS-PAGE.
Figure 16:
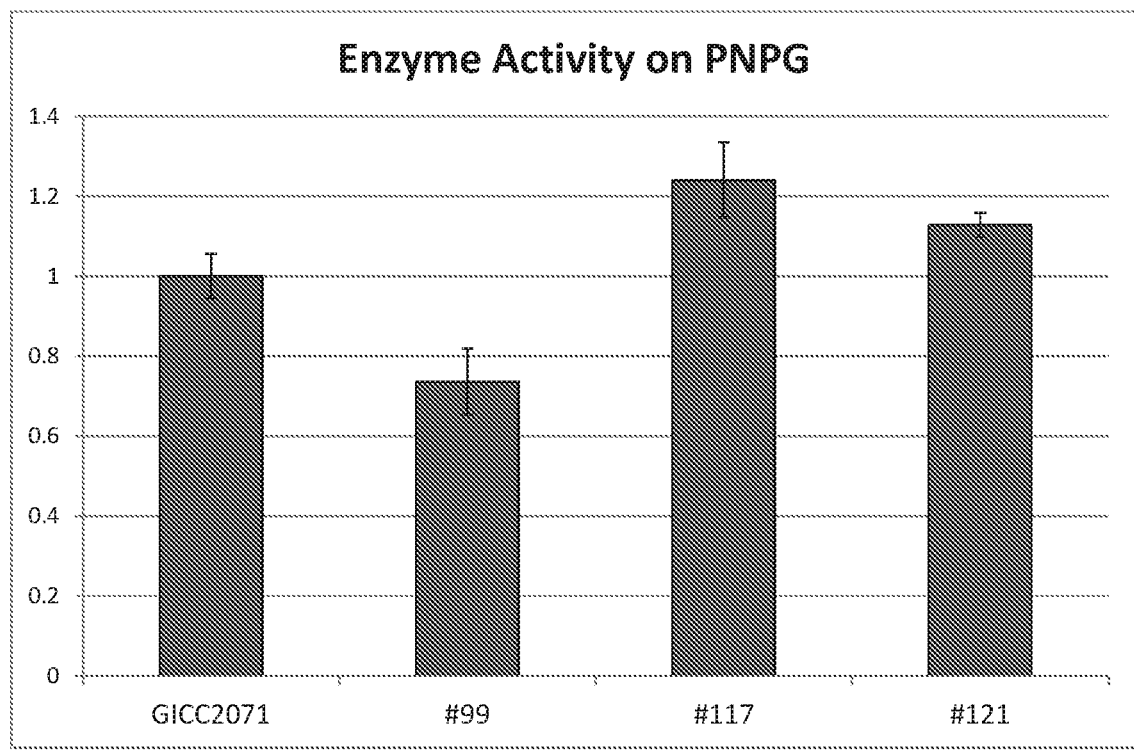
FIG. 16. Compares supernatant enzyme activity on PNPG between strain GICC2071 containing the wild-type nik1 allele and GICC2071 Nik1$^{M786T}$ mutant strains #99, 117, and 121, containing the nik1$^{M786T}$ allele, at shake flask scale. Relative absorbance was normalized to GICC2071 control. Error bars represent standard deviation.

The comparison of the protein production of a strain containing the modified nik1$^{M786T}$ histidine kinase allele with the host strain containing the nik1 wild type (native) allele has been carried out, and it was found that the protein production and enzyme activity on p-nitrophenyl-α-D-glucopyranoside (PNPG) substrate of GICC2071 Nik1$^{M786T}$ showed an improvement over wild-type parent GICC2071 (FIGS. 15 and 16). This indicated that introducing the modified nik1 histidine kinase into a host *A. niger* strain causes an increase in protein production.

In some embodiments, the variant histidine kinase is a variant of the native histidine kinase in that it comprises a mutation of any kind, e.g., single, or multiple (e.g., a few, namely, 1, 2, 3, 4, 5, 6, 7, 8, 9, or even 10 or more) mutations, such as replacements, insertions, deletions, transpositions, terminations (stop codons introduced) and point mutations. In certain instances, a single base pair substitution whereby a single nucleotide base is substituted with a different nucleotide base at the same position, with the corresponding substitution of the complementary base on the other strand of the DNA, can occur. Any such single base pair substitution is contemplated herein as an embodiment of the invention, and accordingly the variant histidine kinase may be encoded by a polynucleotide sequence that comprises a single base-pair substitution as compared to the wild type, parent, histidine kinase gene. The mutations of the variant polynucleotide can appear in protein coding regions or in regions which encode ribosomal or transfer RNAs.

The mutations can be prepared using any mutagenesis procedure known in the art, such as site-directed mutagenesis, synthetic gene construction, semi-synthetic gene construction, random mutagenesis, shuffling, etc.

Site-directed mutagenesis is a technique in which one or more (e.g., several) mutations are introduced at one or more defined sites in a polynucleotide encoding the parent. Site-directed mutagenesis can be accomplished in vitro by PCR involving the use of oligonucleotide primers containing the desired mutation. Site-directed mutagenesis can also be performed in vitro by cassette mutagenesis involving the cleavage by a restriction enzyme at a site in the plasmid comprising a polynucleotide encoding the parent and subsequent ligation of an oligonucleotide containing the mutation in the polynucleotide. Usually the restriction enzyme that digests the plasmid and the oligonucleotide is the same, permitting sticky ends of the plasmid and the insert to ligate to one another. See, e.g., Scherer and Davis, Proc. Natl. Acad. Sci. USA (1979) 76: 4949-4955; and Barton et al., Nucleic Acids Res. (1990) 18: 7349-4966. Site-directed mutagenesis can also be accomplished in vivo by methods known in the art. See, e.g., U.S. Patent Application Publication No. 2004/0171154; Storici et al., Nature Biotechnol. (2001) 19: 773-776; Kren et al., Nat. Med. (1998) 4: 285-290; and Calissano and Macino, Fungal Genet. Newslett. (1996) 43: 15-16. Any site-directed mutagenesis procedure can be used in the present invention. There are many commercial kits available that can be used to prepare variants.

Random mutagenesis may be accomplished through one of various means. One method is chemical mutagenesis by outgrowth in the presence of a mutagenizing reagent such as 2-aminopurine (2AP), N-methyl-N-nitro-N-nitrosoguanidine (MNNG), or ethyl methane sulfonate (EMS), among others (Foster, P. L. Methods Enzymol (1991) 204: 114-125.). Methods for chemical mutagenesis are well known in the art and are described in detail by Miller, J. H. (A short course in bacterial genetics: a laboratory manual and handbook for *Escherichia coli* and related bacteria. Cold Spring Harbor Laboratory Press, Plainview, N.Y. 1992). Mutagenesis may also be accomplished by expressing a mutator gene such as mutD5 off of a plasmid as described by Selifonova et al. (Appl Environ. Microbio. (2001) 167: 3645-3649). Cellular genomes may also be manipulated through transposon mutagenesis, genome shuffling, overexpression of genes from a plasmid, or other cellular engineering techniques (Kleckner, N., Bender, J., and Gottesman, S., Methods Enzymol (1991) 204: 139-180; Patnaik, R., Biotechnol. Frog. (2008) 24: 38-47). Mutant cells may also be produced by simply outgrowing cells and allowing replication errors to naturally occur, as in the method of Miroux and Walker (U.S. Pat. No. 6,361,966). In order to obtain increasingly better mutants, 2 or more rounds of mutagenesis may be performed, and each round may use the same or a different method of mutagenesis.

In certain embodiments, the variant histidine kinase is a variant group III histidine kinase, and may be a naturally-occurring variant of TrNik-1 or AnNik-1 that has at least at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, or even at least about 99% amino acid sequence identity to an amino acid sequence of SEQ ID NO:1 or SEQ ID NO: 43, although the variant histidine kinase does not have 100% identical sequence to SEQ ID NO:1 or SEQ ID NO: 43.

In certain embodiments, the variant histidine kinase may be identified by screening for resistance or sensitivity to certain antifungal compounds, such as, for example, in the presence of high levels of a dicarboximide or phenylpyrrole fungicide such as iprodione or fludioxonil in the medium.

In some embodiments, the variant histidine kinase may be obtained from a fungal strain that is not *Trichoderma reesei* or *Aspergillus niger*, and the variant histidine kinase comprises a polypeptide sequence that is at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, or even at least about 99% identical to the amino acid sequence of SEQ ID NO: 1 or SEQ ID NO: 43; however the variant histidine kinase is not 100% identical to SEQ ID NO:1 or SEQ ID NO: 43.

In some embodiments, the histidine kinase is derived from *Trichoderma* spp., particularly *Trichoderma reesei* (*longibrachiatum*). The histidine kinase may also be derived from another fungus, such as *Absidia* spp.; *Acremonium* spp.; *Agancus* spp., *Anaeromyces* spp; *Aspergillus* spp, including *A. auculeatus, A. awamon, A. flavus, A. foetidus, A. fumaricus, A. fumigatus, A. nidulans, A. niger, A. oryzae, A. terreus* and *A. versicolor, Aeurobasidium* spp.; *Cepha/osporum* spp.; *Chaetomium* spp.; *Chrysosporium* spp; *Coprinus* spp; *Dactyllum* spp.; *Fusarium* spp., including *F. conglomerans, F. decemcellulare, F. javanicum, F. lim, Foxysporum* and *F. solani; Gliocladium* spp.; *Humicola* spp, including *H. insolens* and *H. lanuginosa; Mucor* spp.; *Myceliophthora* spp, including *M. thermophila; Neurospora* spp., including *N. crassa* and *N. sitophila; Neocallimastix* spp; *Orpinomyces* spp.; *Penicillium* spp; *Phanerochaete* spp.; *Phlebia* spp.; *Piromyces* spp.; *Pseudomonas* spp.; *Rhizopus* spp.; *Schizophyllum* spp.; *Trametes* spp; *Trichoderma* spp., including *T reesei, T reesei* (*longibrachiatum*) and *T. vinde*; or *Zygorhynchus* spp. Similarly, it is envisioned that histidine kinase may be found in bacteria such as *Bacillus* spp., *Cellulomonas* spp.; *Clostridium* spp., *Myceliophthora* spp.; *Thermomonospora* spp; *Streptomyces* spp., *S. olivochromogenes; Fibrobacter succinogenes*, and in yeast including *Candida torresn; C. parapsllosis; C. sake; C. zeylanoides, Pichia minuta; Rhodotorula glutinis; R. mucilaginosa,* or *Sporobolomyces roseus*.

Figure 12A:
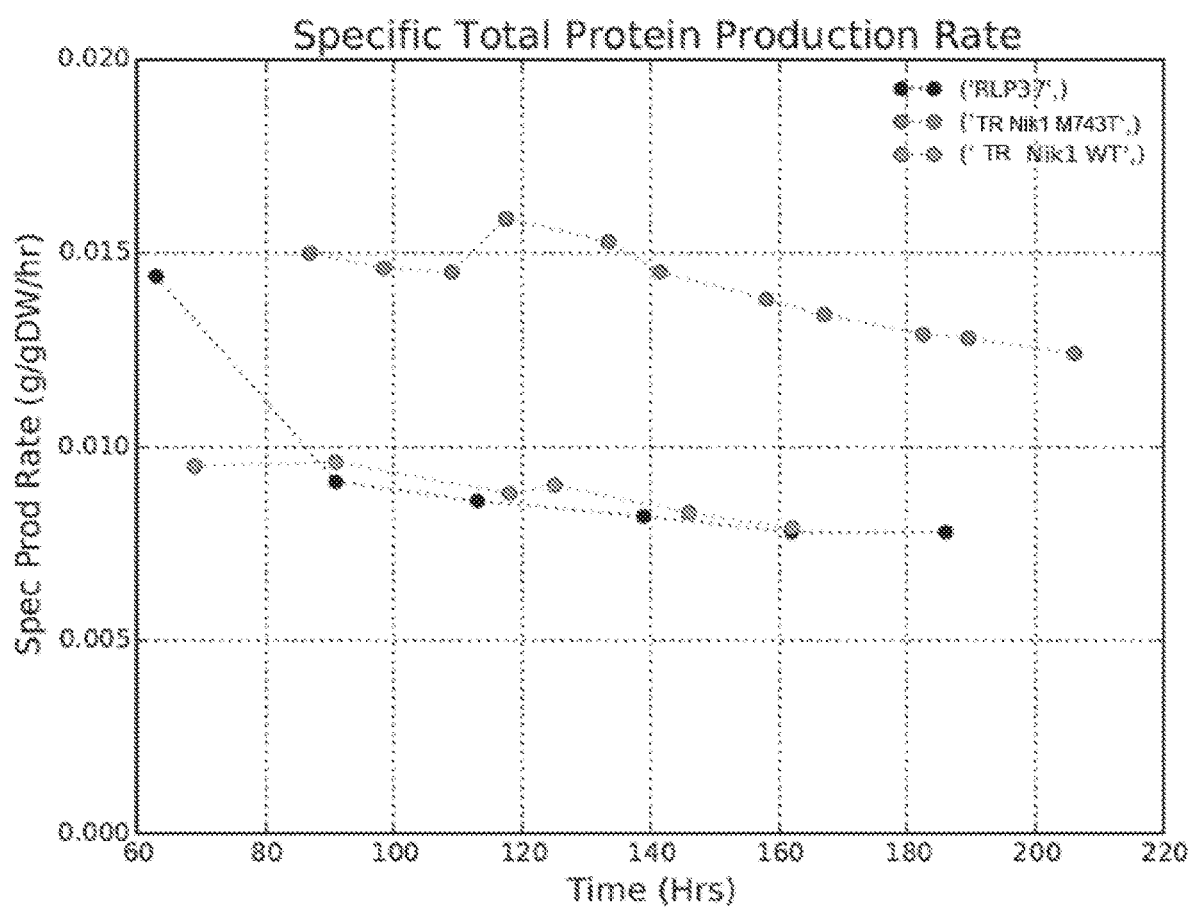
FIGS. 12A-12B. Compares the protein production of RLP37, the parental strain for TR Nik1$^{M743T}$, TR Nik1$^{M743T}$, and TR Nik1$^{WT}$ in DASGIP 2 L scale fermentation.
Figure 12B:
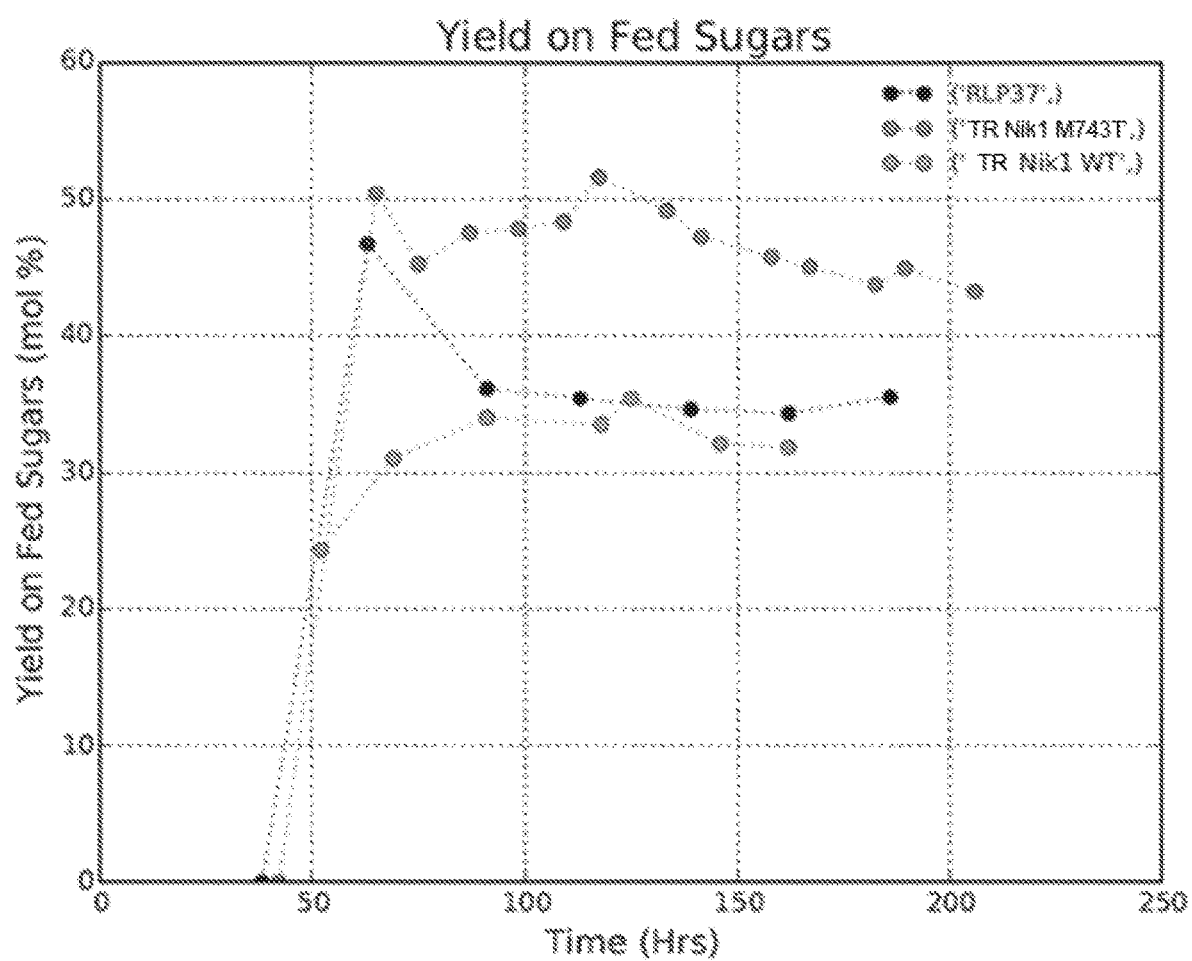

In one example, a Nik1 deletion strain (RLP37 ΔNik1) was constructed in order to determine if the nik1$^{M743T}$ allele resulted in a gain-of-function or loss-of-function. The comparison of protein production and other features of the RLP37 ΔNik1 strain with the RLP37 host strain containing the wild type allele showed that the nik1$^{M743T}$ allele is a gain-of-function allele resulting in a gain-of-function phenotype (FIG. 12).

In certain embodiments, the variant histidine kinase gene encodes a polypeptide that functions as part of a signaling pathway that responds to external osmotic pressure. It may be expected that mutations in other components of this signaling pathway would also be beneficial. These components include, without limitation, MAP kinase proteins and transcription factors that regulate expression of other genes in response to osmotic pressure. Strains with mutations in this pathway can be identified by screening for resistance or sensitivity to osmotic stress, such as, for example, in the presence of high levels of sorbitol or salt in the medium.

For purposes of the present invention, the term "osmotic pressure" refers to the hydrostatic pressure required to stop the net flow of water across the cell membrane of a filamentous fungus. For example, osmotic pressure exposed to a fungal cell can vary by the concentration of components such as salts or sorbitol (e.g., as high as 1.2M) in the growth medium where the fungal cell is cultivated. A cell's capability to withstand high osmotic pressure is beneficial and can be connected with the cell's capacity to produce greater amount of a protein of interest. Along these lines, the engineered fungal strains or derivative fungal strains of the present invention has improved capacity to withstand osmotic pressure as compared to their parental strains.

C. Detection of Protein Production

To confirm that an engineered fungal strain has a capability of producing an improved level of a protein of interest, various methods of screening may be performed. The expression vector may encode a polypeptide fusion to the target protein which serves as a detectable label or the target protein itself may serve as the selectable or screenable marker. The labeled protein may be detected via western blotting, dot blotting (methods available at the Cold Spring Harbor Protocols website), ELISA, or, if the label is GFP, whole cell fluorescence or FACS. For example, a 6-histidine tag would be included as a fusion to the target protein, and this tag would be detected by western blotting. If the target protein expresses at sufficiently high levels, SDS-PAGE combined with Coomassie/silver staining, may be performed to detect increases in mutant expression over wild type, in which case no label is necessary. In addition, other methods may be used to confirm the improved level of a protein of interest, such as, the detection of the increase of protein activity or amount per cell, protein activity or amount per milliliter of medium, allowing cultures or fermentations to continue efficiently for longer periods of time, or through a combination of these methods.

The detection of specific productivity is another method to evaluate the protein production. Specific productivity (Qp) can be determined by the following equation:

$$Qp = gP/gDCW \cdot hr$$

wherein "gP" is grams of protein produced in the tank, "gDCW" is grams of dry cell weight (DCW) in the tank, "hr" is fermentation time in hours from the time of inoculation, which include the time of production as well as growth time.

In some embodiments, the engineered, transformed or derivative fungal strain is capable of producing at least about 0.5%, for example, at least about 0.5%, at least about 0.7%, at least about 1%, at least about 1.5%, at least about 2.0%, at least about 2.5%, or even at least about 3%, or more of a protein of interest, as compared to its parental strain.

D. Employing the Engineered, Transformed or Derivative Fungal Strain for Production of Proteins of Interest In one aspect, the present disclosure provides a method of producing a protein of interest comprising fermenting an engineered, transformed or derivative fungal strain, wherein the engineered, transformed or a derivative fungal strain secrete the protein of interest, wherein the engineered, transformed or a derivative fungal strain comprises a mutation in its histidine kinase gene.

The standard techniques for transformation of fungi and culturing the fungi are well known in the art can be used to transform the improved hosts of the present invention for the production of recombinant proteins. Introduction of a DNA construct or vector into a host cell includes techniques such as transformation; electroporation; nuclear microinjection; transduction; transfection, e.g., lipofection mediated and DEAE-Dextrin mediated transfection; incubation with calcium phosphate DNA precipitate; high velocity bombardment with DNA-coated microprojectiles; gene gun or biolistic transformation and protoplast fusion. General transformation techniques are known in the art. See, e.g., Ausubel et al. (1987), supra, chapter 9; Sambrook et al. (2001), supra; and Campbell et al., Curr. Genet. (1989)16: 53-56. The expression of heterologous protein in *Trichoderma* is described, for example, in U.S. Pat. Nos. 6,022,725; 6,268,328; Harkki et al., Enzyme Microb. Technol. (1991) 13: 227-233; Harkki et al., BioTechnol. (1989) 7: 596-603; EP 244,234 and EP 215,594. Reference is also made to Cao et al., Science (2000) 9: 991-1001 for transformation of *Aspergillus* strains.

Usually transformation of *Trichoderma* sp. uses protoplasts or cells that have been subjected to a permeability treatment, typically at a density of $10^5$ to $10^7$/mL, particularly $2\times10^6$/mL. A volume of 100 µL of these protoplasts or cells in an appropriate solution (e.g., 1.2 M sorbitol and 50 mM $CaCl_2$) is mixed with the desired DNA. Generally, a high concentration of polyethylene glycol (PEG) is added to the uptake solution. Additives, such as dimethyl sulfoxide, heparin, spermidine, potassium chloride and the like, may also be added to the uptake solution to facilitate transformation. Similar procedures are available for other fungal host cells. See, e.g., U.S. Pat. Nos. 6,022,725 and 6,268,328, both of which are incorporated by reference.

In some embodiments, the present invention provides a method of producing a protein of interest comprising fermenting the engineered fungal strain or the transformed fungal strain and derivative fungal strain, wherein the engineered or transformed and derivative fungal strain secret the protein of interest. The fermentation method well known in the art can be used to ferment the engineered or the transformed or the derivative fungal strain. In some embodiments, fungal cells are grown under batch or continuous fermentation conditions. A classical batch fermentation is a closed system, where the composition of the medium is set at the beginning of the fermentation and is not altered during the fermentation. At the beginning of the fermentation, the medium is inoculated with the desired organism(s). In this method, fermentation is permitted to occur without the addition of any components to the system. Typically, a batch fermentation qualifies as a "batch" with respect to the addition of the carbon source, and attempts are often made to control factors such as pH and oxygen concentration. The metabolite and biomass compositions of the batch system change constantly up to the time the fermentation is stopped. Within batch cultures, cells progress through a static lag phase to a high growth log phase and finally to a stationary phase, where growth rate is diminished or halted. If untreated, cells in the stationary phase eventually die. In general, cells in log phase are responsible for the bulk of production of product.

A suitable variation on the standard batch system is the "fed-batch fermentation" system. In this variation of a typical batch system, the substrate is added in increments as the fermentation progresses. Fed-batch systems are useful when catabolite repression likely inhibits the metabolism of the cells and where it is desirable to have limited amounts of substrate in the medium. Measurement of the actual substrate concentration in fed-batch systems is difficult and is therefore estimated on the basis of the changes of measurable factors, such as pH, dissolved oxygen and the partial pressure of waste gases, such as $CO_2$. Batch and fed-batch fermentations are common and well known in the art.

Continuous fermentation is an open system where a defined fermentation medium is added continuously to a bioreactor, and an equal amount of conditioned medium is removed simultaneously for processing. Continuous fermentation generally maintains the cultures at a constant high density, where cells are primarily in log phase growth. Continuous fermentation allows for the modulation of one or more factors that affect cell growth and/or product concentration. For example, in one embodiment, a limiting nutrient, such as the carbon source or nitrogen source, is maintained at a fixed rate and all other parameters are allowed to moderate. In other systems, a number of factors affecting growth can be altered continuously while the cell concentration, measured by media turbidity, is kept constant. Continuous systems strive to maintain steady state growth conditions. Thus, cell loss due to medium being drawn off should be balanced against the cell growth rate in the fermentation. Methods of modulating nutrients and growth factors for continuous fermentation processes, as well as techniques for maximizing the rate of product formation, are well known in the art of industrial microbiology.

E. Proteins of Interest Produced by the Engineered, Transformed or Derivative Strain In certain aspects, the present disclosure provides a protein of interest produced by fermenting an engineered, transformed or a derivative fungal strain, wherein the engineered, transformed or a derivative fungal strain comprises a variant histidine kinase gene and/or is capable of expressing a variant histidine kinase.

The protein of interest can be any endogenous and heterologous protein. The protein can contain one or more disulfide bridges or is a protein whose functional form is a monomer or multimer, i.e. the protein has a quaternary structure and is composed of a plurality of identical (homologous) or nonidentical (heterologous) subunits, wherein the protein of interest is preferably the protein with properties of interest. The protein of interest or the variant protein of interest may be a hemicellulase, peroxidases, protease, cellulase, xylanase, lipase, phospholipase, esterase, cutinase, pectinase, keratinase, reductase, oxidase, phenol oxidase, lipoxygenase, ligninase, pullulanase, tannase, pentosanase, mannanase, beta-glucanase, arabinosidase, hyaluronidase, chondroitinase, laccase, amylase, glucoamylase, a mixture of two or more of these enzymes, a functional fragment of any of these enzymes, or a mixture of any of these enzymes and functional fragments thereof. Non-limiting examples of proteins of interest or variant proteins may also include proteins or enzymes involved in starch metabolism, proteins or enzymes involved in glycogen metabolism, acetyl esterases, aminopeptidases, amylases, arabinases, arabinofuranosidases, carboxypeptidases, catalases, cellulases, chitinases, chymosin, cutinase, deoxyribonucleases, epimerases, esterases, α-galactosidases, β-galactosidases, α-glucanases, glucan lyases, endo-β-glucanases, glucoamylases, glucose oxidases, α-glucosidases, β-glucosidases, glucuronidases, hemicellulases, hexose oxidases, hydrolases, invertases, isomerases, laccases, lipases, lyases, mannosidases, oxidases, oxidoreductases, pectate lyases, pectin acetyl esterases, pectin depolymerases, pectin methyl esterases, pectinolytic enzymes, peroxidases, phenoloxidases, phytases, polygalacturonases, proteases, rhamno-galacturonases, ribonucleases, thaumatin, transferases, transport proteins, transglutaminases, xylanases, hexose oxidase (D-hexose: 02-oxidoreductase, EC 1.1.3.5), variants thereof, functional fragments thereof, or combinations thereof.

The protein of interest may also suitably be a peptide hormone, a growth factor, a clotting factor, a chemokine, a cytokine, a lymphokine, an antibody, a receptor, an adhesion molecule, a microbial antigen (e.g., HBV surface antigen, HPV E7, etc.), a variant thereof, a functional fragment thereof, or a mixture of any of these substances above.

Other types of proteins or variants of interest may include those capable of providing nutritional value to a food or to a crop. Non-limiting examples include plant proteins that can inhibit the formation of anti-nutritive factors and plant proteins that have a more desirable amino acid composition (e.g., a higher lysine content than a non-transgenic plant).

F. Use of the Composition Thus Made

In certain aspects, the present disclosure provides a composition comprising a protein of interest produced by an engineered fungal cell, wherein the engineered fungal cell comprises a variant histidine kinase gene and/or is capable of expressing a variant histidine kinase. The composition is suitably produced using a method provided herein. The composition comprises a protein of interest, encoded by a gene of interest, expressed using a method described herein. The composition may be used in various useful industrial applications such as, for example, in biomass hydrolysis, cleaning applications, grain processing, animal nutrition, food composition, textile treatment, and the like.

For example, the composition produced by the engineered host cell of the present disclosure, and/or using the method or process provided herewith, can be used in lignocellulosic biomass hydrolysis. Lignocellulose, the world's largest renewable biomass resource, is composed mainly of lignin, cellulose, and hemicellulose, of which the large part of the latter is xylan. The conversion of lignocellulosic feedstocks into ethanol has the advantages of the ready availability of large amounts of feedstock, the desirability of avoiding burning or land filling the materials, and the cleanliness of the ethanol fuel. Wood, agricultural residues, herbaceous crops, and municipal solid wastes have been considered as feedstocks for ethanol production. Once the lignocellulose is converted to fermentable sugars, e.g., glucose, the fermentable sugars are easily fermented by yeast into ethanol. Cellulose is a polymer of the simple sugar glucose covalently linked by beta-1,4-bonds. Many microorganisms produce enzymes that hydrolyze beta-linked glucans. These enzymes include endoglucanases, cellobiohydrolases, and beta-glucosidases. Xylans are polysaccharides formed from 1,4-β-glycoside-linked D-xylopyranoses. Xylanases (e.g., endo-1,4-beta-xylanase, EC 3.2.1.8) hydrolyze internal β-1,4-xylosidic linkages in xylan to produce smaller molecular weight xylose and xylo-oligomers. The disclosure provides a transformed fungal cell, which has demonstrated improved protein production, suitable and advantageous as a producer of industrial enzymes, variants, and mixtures of interest to such lignocellulosic biomass use.

In another example, the composition produced by the engineered host cell of the present disclosure, and/or using the method or process provided herewith can be used in cleaning application. Enzymatic cleaning components are popular because of their ability to break down soils, stains, and other debris that are otherwise not readily removed by conventional chemical detergents. Well-known enzymes useful for cleaning include proteases and amylases, with other enzymes such as lipases, pectinases, mannanases, even certain cellulases, each providing a set of different functionalities. Proteases combat protein-based stains; amylases work on carbohydrates and starches; and lipases break down lipids or fats, for example. The disclosure provides a transformed fungal cell, which has demonstrated improved protein production, suitable and advantageous as a producer of industrial enzymes, variants, and mixtures of interest to such use in cleaning applications.

In another example, the composition produced by the engineered host cell of the present disclosure, and/or using the method or process provided herewith can be used in grain procession. Starch is the commonest storage carbohydrate in plants, used by the plants themselves as well as by microbes and by higher organisms. A great variety of enzymes are able to catalyze starch hydrolysis. Starch from all plant sources occurs in the form of granules, but depending on the species of the plant source, starch presents in markedly different size and physical characteristics. Acid hydrolysis of starch had widespread use in the past, however this process has now largely been replaced by enzymatic processes, which are known to demand less corrosion-resistant materials and other benefits, need less energy for heating and are relatively easier to control than the acid process. The disclosure provides a transformed fungal cell, which has demonstrated improved protein production, suitable and advantageous as a producer of industrial enzymes, variants, and mixtures of interest to such use in starch degradation and grain processing.

In another example, the composition produced by the engineered host cell of the present disclosure, and/or using the method or process provided herewith can be used in food application. Enzymes produced by bacteria, yeasts and molds (or moulds) have been used in food application to make foods such as bread, cheese, beer and wine for many thousands of years. Today enzymes are used in bakery, cheese making, starch processing and production of fruit juices and other drinks, providing various benefits such improved texture, appearance and nutritional value, generate desirable flavors and aromas, and the like. Food enzymes typically originate in animals and plants (for example, a starch-digesting enzyme, amylase, can be obtained from germinating barley seeds) as well as from a range of beneficial microorganisms. Enzymes are deemed viable and desirable alternatives to traditional chemical-based technology, replacing synthetic chemicals in many processes. Enzymes can help improve the environmental performance of food production processes, reducing energy consumption and improving biodegradability of waste or side products. Enzymes tend to be more specific in their actions than synthetic chemicals, and as such, enzymatic processes tend to give fewer side reactions and waste or byproducts, and consequently producing higher quality products and reducing the likelihood of pollution. Enzymatic processes are often also the only processes possible. An example of this is in the production of clear apple juice concentrate, which relies on the use of the enzyme, pectinase. Most of the food enzymes are produced from microorganisms such *Bacillus, Aspergillus, Streptomyces* or *Kluyveromyces*. The disclosure provides a transformed fungal cell, which has demonstrated improved protein production, suitable and advantageous as a producer of industrial enzymes, variants, and mixtures of interest to such use in food applications.

In another example, the composition produced by the engineered host cell of the present disclosure, and/or using the method or process provided herewith can be used in animal feed additive. Cellulase, xylanase, beta-glucanase, alpha-amylase, protease, lipase, phytase and other carbohydrase have been widely used in animal feed industry. Since many plant based feeds contain substances with anti-nutritional factors that reduce animal growth, the enzymes added to such feeds improve digestibility of these anti-nutritional factors by degrading fibers, proteins, starches and phytates, rendering them more digestible by the animals, and enabling the use of cheaper and often locally produced feeds, while maximizing meat, egg or milk productivity. At the same time, the enzymes added to such feeds also may provide benefits supporting gut health and enhanced animal performance. The disclosure provides a transformed fungal cell, which has demonstrated improved protein production, suitable and advantageous as a producer of industrial enzymes, variants, and mixtures of interest to such use in animal feed applications.

In yet a further example, the composition produced by the engineered host cell of the present disclosure, and/or using the method or process provided herewith can be used in textile applications. Enzymes have become an integral part of the textile processing. There are two well-established enzyme applications in the textile industry. First, enzymes such as amylases are commonly used in the preparatory finishing area for desizing. Second, enzymes such as cellulases are commonly used in the finishing area for softening, bio-stoning and reducing of pilling propensity of cotton goods. Other enzymes such as, for example, pectinases, lipases, proteases, catalases, xylanases etc., are also used in textile processing. Moreover, there are various applications which entail enzymes included fading of denim and non-denim, bio-scouring, bio-polishing, wool finishing, peroxide removal, decolourization of dyestuff, etc. (Cavaco-Paulo A and Gübitz G M. Textile Processing with Enzymes, 2003, 1st Edition; Chelikani P, Fita I, Loewen P C. Cell Mol Life Sci. (2004) 61:192-208; Nalankilli. G., Colourage, 1998, XLV (10), 17-19; Shenai, V. A. and Saraf, N. M. Technology of Finishing, (1990), Vol. X.II Edition). The disclosure provides a transformed fungal cell, which has demonstrated improved protein production, suitable and advantageous as a producer of industrial enzymes, variants, and mixtures of interest to such use in textiles applications.

G. The Screening Method for Identifying the Fungal Strain Capable of Producing an Altered Level of a Protein of Interest In a further aspect, the disclosure provides a method for identifying or selecting for an engineered fungal strain capable of producing an altered level of a protein of interest as compared to a parental strain, comprising the steps of:
  (a) inoculating the strain onto the surface of agar plate with osmotic agents or/and dicarboximide or phenylpyrrole fungicide; and
  (b) selecting or screening for the strains that grow faster or slower than the parental strain.

In some embodiments, the engineered fungal strain capable of producing an altered level of a protein of interest as compared to a parental (unaltered) strain, comprises a mutation that causes altered sensitivity or resistance to external osmotic pressure as compared to the parental strain.

In some embodiments, the engineered fungal strain capable of producing an altered level of protein of interest as compared to a parental (unaltered) strain, comprises a mutation that causes altered sensitivity or resistance to a dicarboximide or phenylpyrrole fungicide as compared to the parental strain.

In some embodiments, the engineered fungal strain capable of producing an altered level of protein of interest as compared to a parental (unaltered) strain comprises a mutation that causes altered sensitivity or resistance to osmotic pressure and altered sensitivity or resistance to a dicarboximide or phenylpyrrole fungicide compared to the parental strain.

It is believed that mutations in other components of this signaling pathway would also be beneficial to the productivity of the fungal strain. These components include, without limitation, MAP kinase proteins and transcription factors that regulate expression of other genes in response to osmotic pressure.

Strains with mutations in this pathway can be identified by screening for resistance or sensitivity to osmotic stress, such as, for example, in the presence of high levels of osmotic agent in the medium. In general, the strains are inoculated onto the surface of nutrient agar plates with various levels of osmotic agent, which can be one or a combination of one or more sugars, sugar alcohols or salts (e.g. glucose, sucrose, fructose, oligofructose, fructo-oligosaccharide, inverted sugar, sorbitol, xylitol, galactosylosorbitol, sodium chloride or potassium chloride), such that individual colonies arise and can be distinguished upon culture. The growth of the mutant was significantly impaired; it tended to form small clumps of irregular-shaped hyphae that were hyper-branched and swollen. These results indicated that the mutant is unable to form a well-defined mycelium under conditions of high osmotic pressure.

The altered sensitivity may manifest itself as an ability to grow faster than the parent, non-mutated cell under conditions of high osmotic pressure (i.e., resistance to high osmotic pressure) or as a reduced growth rate compared to the parent, non-mutated cell under conditions of high osmotic pressure (i.e., sensitivity to high osmotic pressure).

Individual colonies that grow faster or slower than the parental type are picked for further evaluation by growth under identical conditions in submerged (liquid culture) and their specific total secreted protein production rates and yields on fed sugar compared. In this way, mutant fungal strains are identified that have altered sensitivity to osmotic pressure and increased secreted protein production rates compared to a parental strain.

EXAMPLES

Aspects of the present strains, compositions and methods may be further understood in light of the following examples, which should not be construed as limiting. Modifications to materials and methods will be apparent to those skilled in the art.

Example 1

Figure 2:
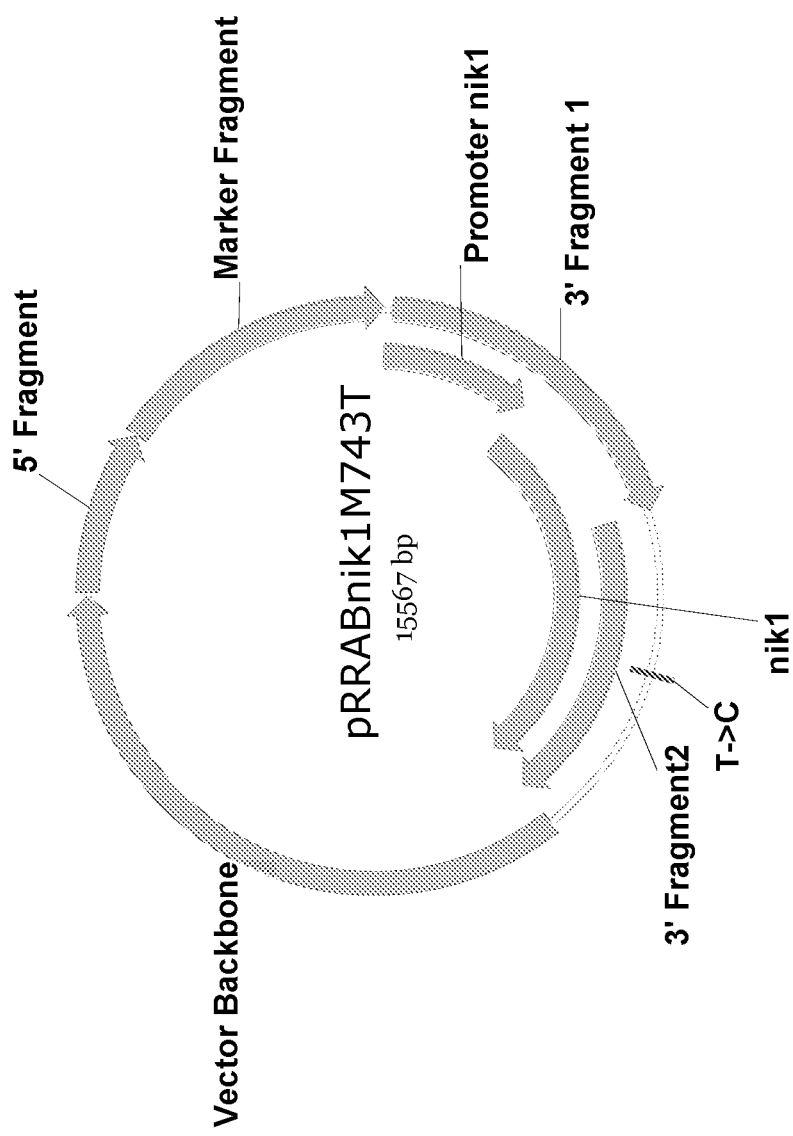
FIG. 2. Depicts a map of pRRAB nik1$^{M743T}$ with the gene replacement cassette containing the nik1$^{M743T}$ allele.

Creating an Engineered Fungal Strain with One Mutation in Nik1 Gene 1.1 Generation of Nik1$^{M743T}$ Gene Replacement Cassette A gene replacement construct was made (FIG. 2) by fusing a DNA fragment containing the 5' region upstream of the nik1 locus, a loxP-flanked hygromycin B-resistance marker cassette and two DNA fragments containing the promoter and nik1 gene (including the T to C substitution that changes the amino acid at position 743 from methionine to threonine), with the 2µ backbone-containing yeast vector pRS426 (from pRS426 phagemid in *E. coli*, ATCC® 77107™).

The following primers were prepared by Integrated DNA Technologies, Inc. (Coralville, Iowa, USA)

RRab88 (Forward)—5'-CGATTAAGTTGGGTAAC-GCCAGGGCCTAGGTGGCTTTGAGCGGTGTT-GATGTGTA-3' (SEQ ID NO:2), which was used to amplify DNA sequence upstream of nik1 (5' Flank) with AvrII restriction site and vector backbone tail overhang for plasmid pRRabnik1M743T.

RRab89 (Reverse)—5'-TACACATCAACACCGCT-CAAAGCCACCTAGGCCCTGGCGTTACCCAACT-TAATCG-3' (SEQ ID NO:3), which was used to amplify the vector backbone with an AvrII restriction site and 5' Flank tail overhang for plasmid pRRabnik1M743T.

RRab90 (Forward)—5'-CTGCTCGAGAAGAACCGT-GAGCGAGCCTAGGGTGAGGGTTAAT-TGCGCGCTTGG C-3' (SEQ ID NO:4), which was used to amplify the vector backbone with an AvrII restriction site and 3' Flank fragment 2 tail overhang for plasmid pRRabnik1M743T.

RRab91 (Reverse)—5'-GCCAAGCGCGCAATTAACC-CTCACCCTAGGCTCGCTCACGGTTCTTCTC-GAGCAG-3' (SEQ ID NO:5), which was used to amplify nik1 DNA sequence (3' Flank, fragment 2) with AvrII restriction site and vector backbone tail overhang for plasmid pRRabnik1M743T.

RRab92 (Forward)—5'-GAATCCACGTGCCGCGA-GGCTCAGCATTTAAATATAACTTCGTATAGCATA-CATT ATACGAAGTTATCCTGGGCTTGTGACTGG-TCGCGA-3' (SEQ ID NO:6), which was used to amplify the hygromycin resistance marker with a loxP site along with a SwaI restriction site and 5' Flank tail overhang for plasmid pRRabnik1M743T.

RRab93 (Reverse)—5'-TCGCGACCAGTCACAAGC-CCAGGATAACTTCGTATAATGTATGCTATACGA-AGTT ATATTTAAATGCTGAGCCTCGCGGCACGTG-GATTC-3' (SEQ ID NO:7), which was used to amplify DNA sequence upstream of nik1 (5' Flank) with a SwaI restriction site and hph+loxP site tail overhang for plasmid pRRabnik1M743T.

RRab94 (Forward)—5'-CGTAACACCCAATACG-CCGGCCGATAACTTCGTATAGCATACATTATACG-AAGTT ATGCGGCCGCGCCCAGGATCACAAACC-CACCGCAG-3' (SEQ ID NO:8), which was used to amplify nik1 gene (3' Flank Fragment 1) with Nod restriction site and hph+loxP site tail overhang for plasmid pRRabnik1M743T.

RRab95 (Reverse)—5'-CTGCGGTGGGTTTGT-GATCCTGGGCGCGGCCGCATAACTTCGTATAAT-GTATGCT ATACGAAGTTATCGGCCGGCGTAT-TGGGTGTTACG-3' (SEQ ID NO:9), which was used to amplify the hygromycin resistance marker with a loxP site along with a Nod restriction site and 3' Flank fragment 1 tail overhang for plasmid pRRabnik1M743T.

RRab110 (Forward)—5'-GAAATTGCCTCCGT-CACAACAGCCGTCGCTCACGGCGATCTGACAA-AGAA-3'(SEQ ID NO:10), which was used to amplify nik1 DNA sequence (3' Flank Fragment 2) with 3' Flank fragment 1 overhang for plasmid pRRabnik1M743T.

RRab111 (Reverse)—5'-TTCTTTGTCAGATCGCCGT-GAGCGACGGCTGTTGTGACGGAGGCAATTTC-3' (SEQ ID NO:11), which was used to amplify nik1 gene (3' Flank Fragment 1) with 3' Flank fragment 2 overhang for plasmid pRRabnik1M743T.

PCR amplifications were performed using the PfuUltraII Fusion HS DNA polymerase (Agilent Technologies, Santa Clara, Calif., USA) and a Tetrad 2 thermal cycler (Bio-Rad, Hercules, Calif., USA). PCR products were separated on EX gels (Life Technologies, Grand Island, N.Y., USA), and fragments of the correct length were purified using the QIAquick Gel Extraction kit (Qiagen Inc., Valencia, Calif., USA). Each of the four DNA fragments had a 5' primer extension complementary to the adjacent DNA fragment to provide a sufficient length of homologous sequence for recombination, and all were recombined into the final construct in the *Saccharomyces cerevisiae* strain YPH499 (ATCC 76625) using the yeast's native recombination machinery. The Frozen EZ Yeast Transformation II™ kit (Zymo Research, Orange, Calif., USA) was used for yeast transformations. Transformants were plated on SD-U plates to select for complementation of uridine auxotrophy. Individual colonies from the transformation plates were selected to extract plasmid DNA using the Zymoprep™ Yeast Plasmid Miniprep II kit (Zymo Research, Orange, Calif., USA). From each miniprep 1 µL was directly transformed into One Shot® TOP10 chemically competent *E. coli* cells (Life Technologies, Grand Island, N.Y., USA), and plated on LB plates with carbenicillin. Individual colonies from the transformation plates were selected to extract plasmid DNA using the QIAprep Spin Miniprep kit (Qiagen Inc., Valencia, Calif., USA). DNA obtained this way was sequenced at Sequetech Corporation (Mountain View, Calif., USA), and a plasmid with the correct sequence selected for DNA amplification. The gene replacement cassette was amplified with PCR using the following primers:

```
RRab156
                                    (SEQ ID NO: 12)
(5'-TGGCTTTGAGCGGTGTTGATGTGTA-3');
and RRab157
                                    (SEQ ID NO: 13)
(5'-CTCGCTCACGGTTCTTCTCGAGCAG-3').
```

The PCR product was purified and concentrated using a QIAquick PCR purification kit (Qiagen Inc., Valencia, Calif., USA).

1.2. RLP37 Host Strain Transformation with Nik1$^{M743T}$ Allele-Containing Gene Replacement Cassette, Candidate Selection, Verification and Characterization The purified concentrated gene replacement cassette was transformed into the *T. reesei* host strain RLP37 (described by Sheir-Neiss, et al., Appl. Microbiol. Biotechnol. 20:46-53 (1984)) using PEG-mediated transformation (Penttila et al., Gene, 61(2):155-64 (1987)). Transformants were plated on Vogel's medium (Vogel, Microbial Genet. Bull. 13:42-43 (1956); Vogel, Am. Nat. 98:435-446 (1964)) containing 100 µg/mL hygromycin B using overlays, and incubated at 28° C. Genomic DNA from stable transformants resistant to hygromycin B was extracted using the NucleoSpin® PlantII kit (Machery-Nagel, Bethlehem, Pa., USA). This genomic DNA was then used as template for diagnostic PCRs to confirm homologous recombination of the gene replacement at the native nik1 locus. The primer pairs RRab117 and RRab167 used for diagnostic PCR are specified.

```
RRab117
                                    (SEQ ID NO: 14)
(5'-CGAACTGTGACCTTTCAAGT-3');
and RRab167
                                    (SEQ ID NO: 15)
(5'-GCACACACATCTCGGCCTTA-3').
```

Figures 3A, 3B, 3C, 3D, 3E, 3F:
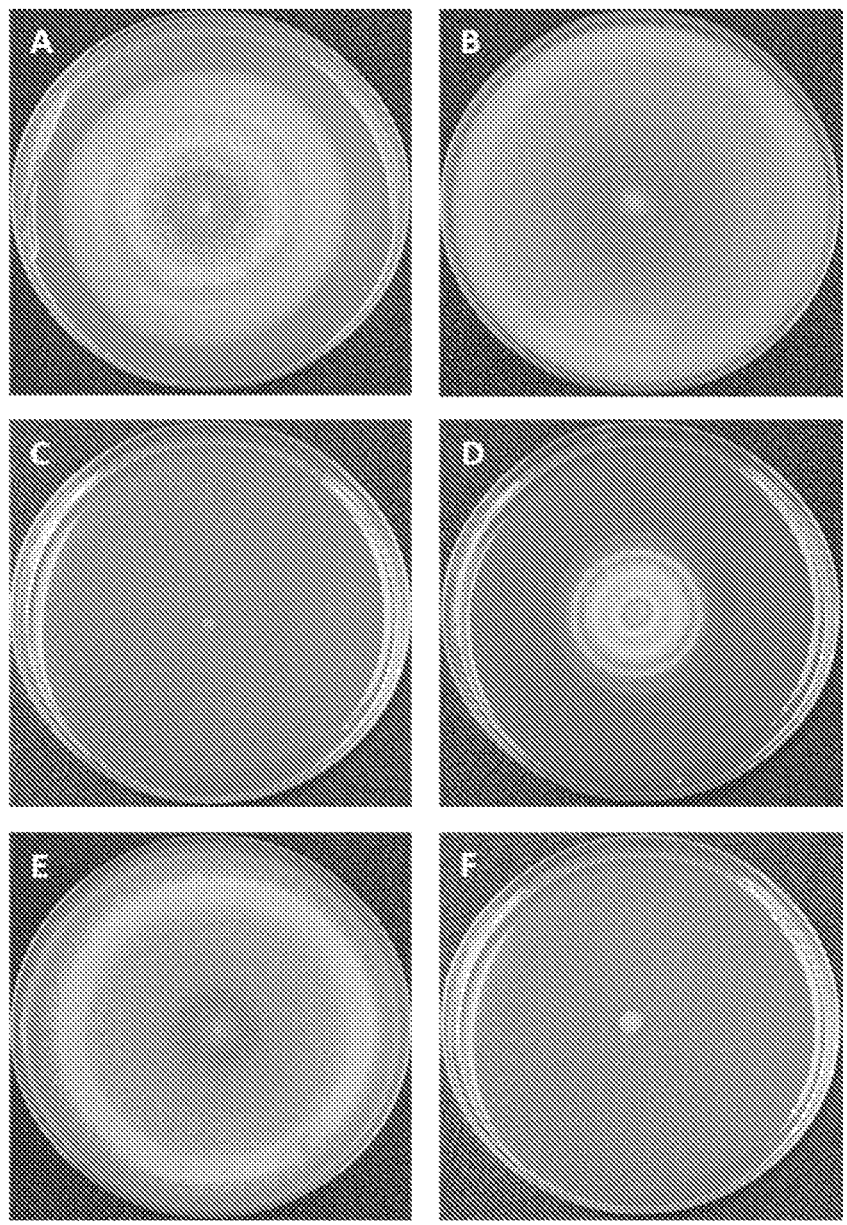
FIGS. 3A-3F. Compares colony phenotypes of RLP37, RLP37 Nik1$^{M743T}$, and RLP37 ΔNik1 on various media.

A strain with verified homologous integration of the nik1$^{M743T}$-containing gene replacement cassette labeled RLP37 Nik1$^{M743T}$ was selected and spore-purified. Spore-purification was performed by harvesting mature aerial conidiospores produced on a PDA plate culture in water, making 10× serial dilutions of the conidiospore suspension, plating the serial dilutions of the suspension on PDA plates and incubating them overnight at 28° C. The selected spore-purified strain was used for determining the effect of the gene replacement on protein production and remaining experiments. The phenotype of the RLP37 Nik1$^{M743T}$ strain on PDA plates consisted of slower growth and a lower yield of conidiospores when compared to the host RLP37 strain (FIGS. 3A and 3B). When sorbitol was added to Vogel's minimal medium colony growth of the strain was restricted compared to RLP37, indicating sensitivity to sorbitol most likely due to an inability to regulate a response to osmotic stress (FIGS. 3C and 3D).

1.3 Fermentation of *T. reesei* RLP37 Nik1$^{M743T}$ to Evaluate Total Protein Production

*Trichoderma reesei* strains RLP37 Nik$^{M743T}$ and RLP37 were grown under identical conditions in submerged (liquid culture), and their specific total protein production rates and yields on fed sugar compared in 2 L (DASGIP) and 14 L fermentors.

To create a seed culture, the spores of each strain were added separately to 50 mL of citrate minimal medium in a 250 mL flask. The cultures were grown for 48 h at 30° C. and 170 rpm in a shaking incubator. After 48 h, 145.6 mL of 50% glucose, and 0.6 g/kg of CaCl$_2$, adjusted to pH 3.5 was inoculated with the seed culture. Thereafter, the temperature was maintained at 30° C., and pH at 3.5. A glucose-sophorose feed was thereafter introduced, and the temperature was dropped to 25° C., pH increased to 4.8.

Figure 4B:
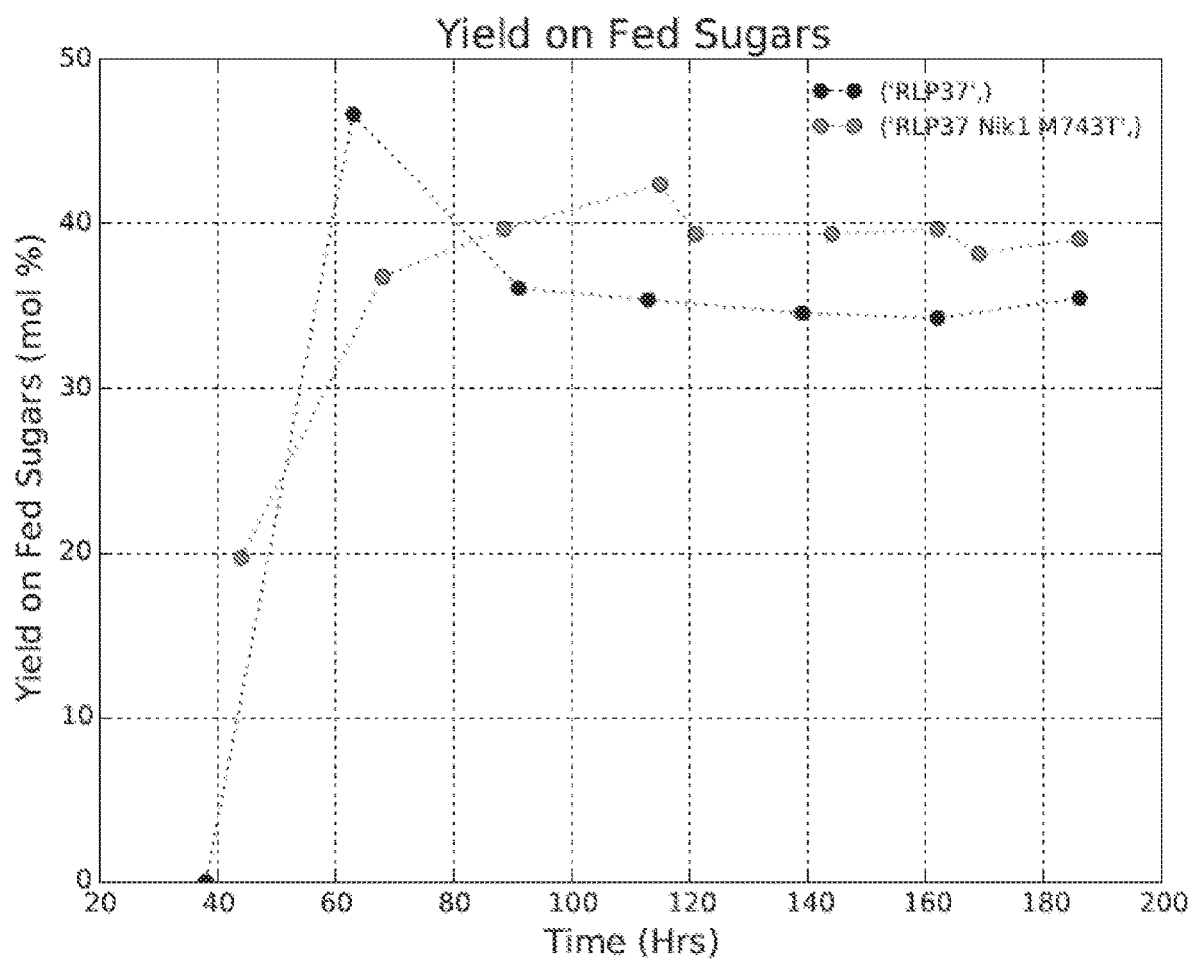

Dry cell weight, total protein concentrations and other parameters were measured, and specific total protein production rates and yield on fed sugars calculated. The RLP37 Nik1$^{M743T}$ strain containing the nik1$^{M743T}$ allele at the native locus showed an improvement in the specific total protein production rate (FIG. 4A) and an improvement in yield on fed sugars over the RLP37 host containing the native nik1 allele (FIG. 4B).

For 14 L fermentations, strains RLP37 Nik$^{M743T}$ and RLP37 were grown under identical conditions in submerged (liquid culture), and their total protein production and specific protein production rates were also compared. Fermentation runs were carried out using a similarly-prepared seed culture, and in 14 L fermenters. Post fermentation, total protein production and specific protein production rates were compared.

Figure 5A:
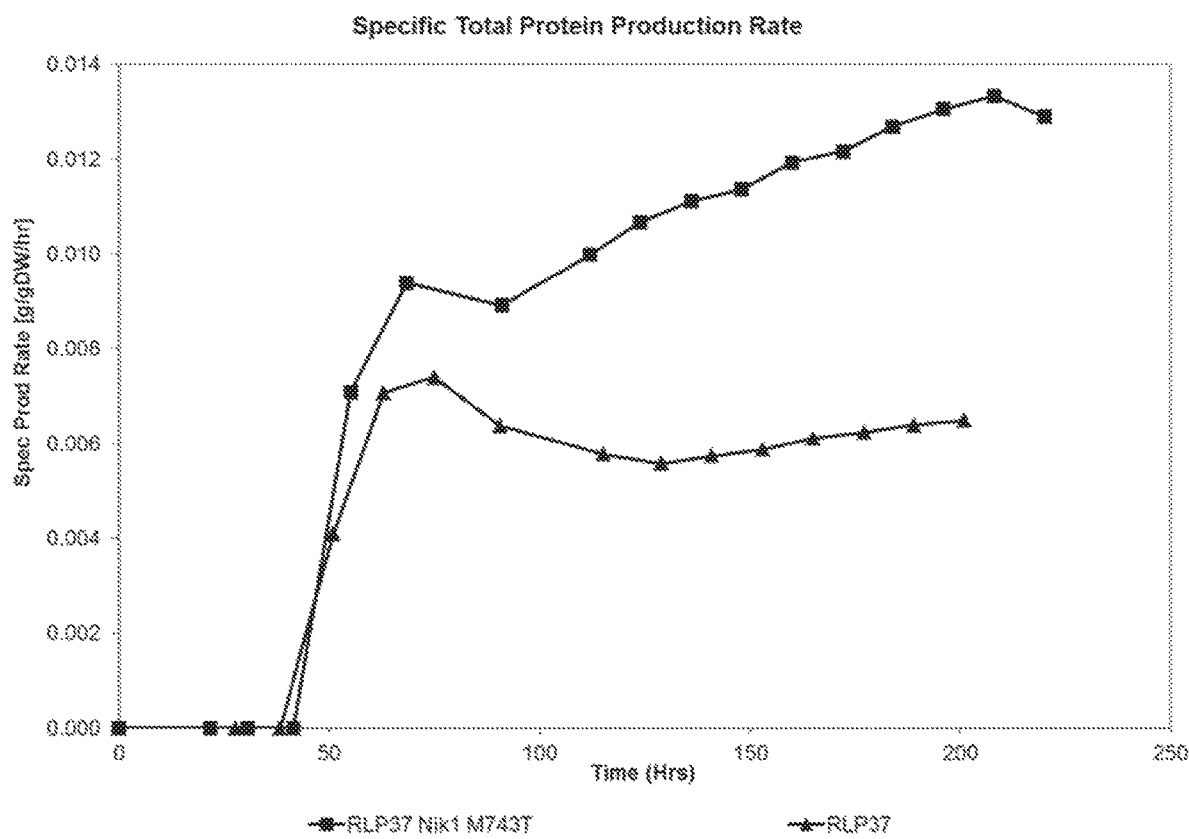
FIGS. 5A-5B. Compares the protein production of RLP37 and RLP37 Nik1$^{M743T}$ in 14 L scale standard fungal fermentation.
Figure 5B:
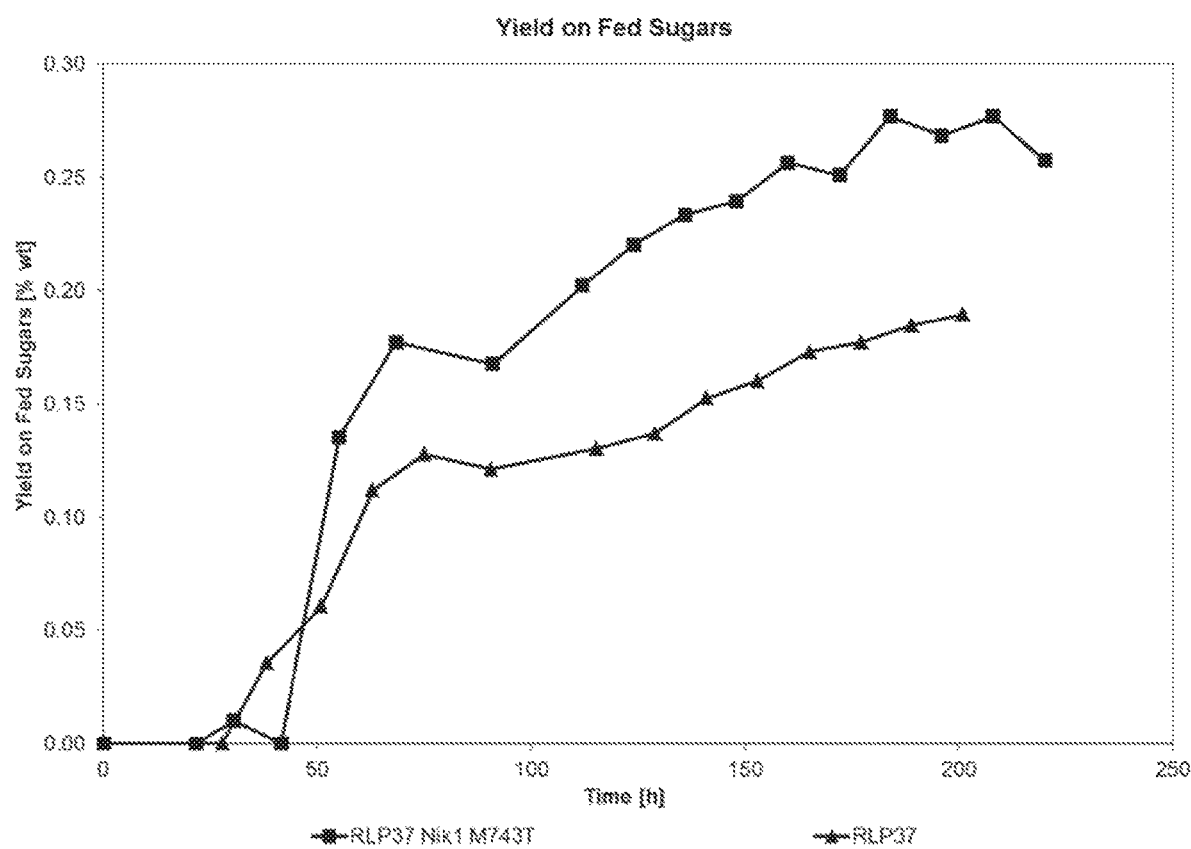

The RLP37 Nik1$^{M743T}$ strain showed a 101% increase in total protein specific production rate (FIG. 5A), and a 46% improvement in yield on fed sugars (FIG. 5B), indicating that introducing the modified nik1 histidine kinase into a host *T. reesei* strain causes an increase in protein production.

Example 2

Figure 6:
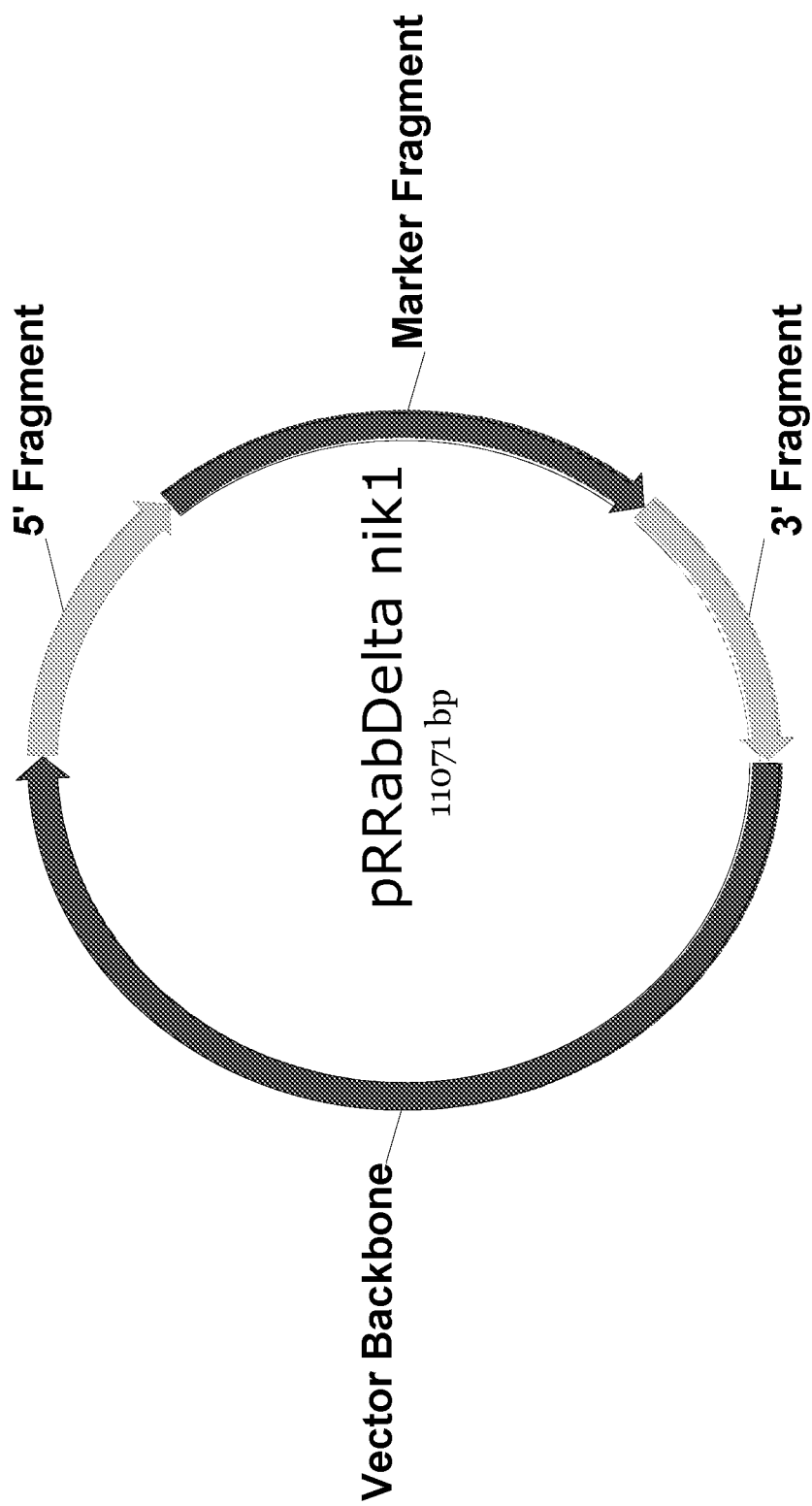
FIG. 6. Depicts a plasmid map of pRRAB Δnik1 containing the Δnik1::hph gene deletion cassette.

Creating a Fungal Strain with Nik1 Gene Deletion 2.1 ΔNik1::Hph Deletion Cassette Design and Creation A gene replacement construct was made (FIG. 6) by fusing a DNA fragment containing the 5' flank of the nik1 gene, a loxP-flanked hygromycin B-resistance cassette and a DNA fragment containing the 3' flank of the nik1 gene with the 2µ backbone-containing yeast vector pRS426 (from pRS426 phagemid in *E. coli*, ATCC® 77107™). The following primers were made by Integrated DNA Technologies Inc. (Coralville, Iowa, USA).

RRab266 (Forward)—5'-CCTGGGGAACCCCCCA-GCGCCCGGCGAGCTCATAACTTCGTATAGCATACAT-TAT ACGAAGTTATCCTGGGCTTGTGACTGGTC-GCGAGC-3' (SEQ ID NO:16), which was used to amplify the hygromycin resistance marker with a loxP site along with a SacI restriction site and 5' Flank tail overhang for plasmid pRRabΔnik1.

RRab267 (Reverse)—5'-CTTTCGCCGTCCAGGCG-TCCAGACACCTGGTATAACTTCGTATAATGTATGC-TAT ACGAAGTTATCGGCCGGCGTATTGGGTGT-TACGGA-3' (SEQ ID NO:17), which was used to amplify the hygromycin resistance marker with a loxP site along with a SexAI restriction site and 3' Flank tail overhang for plasmid pRRabΔ nik1.

RRab268(Forward)—5'-TCCGTAACACCCAATACG-CCGGCCGATAACTTCGTATAGCATACATTATAC-GAAG TTATACCAGGTGTCTGGACGCCTGGACGGC-GAAAGA-3' (SEQ ID NO:18), which was used to amplify DNA sequence downstream of nik1 (3' Flank) with SexAI restriction site and hph+loxP site tail overhang for plasmid pRRabΔnik1.

RRab269 (Reverse)—5'-CGCCAAGCGCGCAAT-TAACCCTCACGGCCATAATGGCCGCTGGGTTCT-GAACCTG TAAAGTAC-3' (SEQ ID NO:19), which was used to amplify DNA sequence downstream of nik1 (3' Flank) with SfiI restriction site and vector backbone tail overhang for plasmid pRRabΔnik1.

RRab270 (Forward)—5'-GTACTTTACAGGTTCAG-AACCCAGCGGCCATTATGGCCGTGAGGGTTAAT-TGCGC GCTTGGCG-3' (SEQ ID NO:20), which was used to amplify the vector backbone with SfiI restriction site and 3' flank tail overhang for plasmid pRRabΔnik1.

RRab271 (Reverse)—5'-TGTAGGTAAGGTAGATCGA-ACTGTGAAGCTTCCCTGGCGTTACCCAACT-TAATCG C-3' (SEQ ID NO:21), which was used to amplify DNA sequence upstream of nik1 (5' Flank) with HindIII restriction site and vector backbone tail overhang for plasmid pRRabΔnik1.

RRab272 (Forward)—5'-GCGATTAAGTTGGGTAAC-GCCAGGGAAGCTTCACAGTTCGATCTACCTTACC-TAC A-3' (SEQ ID NO:22), which was used to amplify DNA sequence upstream of nik1 (5' Flank) with HindIII restriction site and vector backbone tail overhang for plasmid pRRabΔnik1.

RRab273 (Reverse)—5'-GCTCGCGACCAGT-CACAAGCCCAGGATAACTTCGTATAATGTATGC-TATACGAAG TTATGAGCTCGCCGGGCGCTGG-GGGGTTCCCCAGG-3' (SEQ ID NO:23, which was used to amplify DNA sequence upstream of nik1 (5' Flank) with Sac' restriction site and hph+loxP site tail overhang for plasmid pRRabDelta nik1.

PCR amplifications were performed using the PfuUltraII Fusion HS DNA polymerase (Agilent Technologies, Santa Clara, Calif., USA) and a Tetrad 2 thermal cycler (Bio-Rad, Hercules, Calif., USA). PCR products were separated on EX gels (Life Technologies, Grand Island, N.Y., USA), and fragments of the correct length were purified using the QIAquick Gel Extraction kit (Qiagen Inc., Valencia, Calif., USA). Each of the four DNA fragments had a 5' primer extension complementary to the adjacent DNA fragment to provide a sufficient length of homologous sequence for recombination, and all were recombined into the final construct in the Saccharomyces cerevisiae strain YPH499 (ATCC 76625) using the yeast's native recombination machinery. The Frozen EZ Yeast Transformation II™ kit (Zymo Research, Orange, Calif., USA) was used for yeast transformations. Transformants were plated on SD-U plates to select for complementation of uridine auxotrophy. Individual colonies from the transformation plates were selected to extract plasmid DNA using the Zymoprep™ Yeast Plasmid Miniprep II kit (Zymo Research, Orange, Calif., USA). From each miniprep 1 μL was directly transformed into One Shot® TOP10 chemically competent E. coli cells (Life Technologies, Grand Island, N.Y., USA), and plated on LB plates with carbenicillin. Individual colonies from the transformation plates were selected to extract plasmid DNA using the QIAprep Spin Miniprep kit (Qiagen Inc., Valencia, Calif., USA). DNA obtained this way was sequenced at Sequetech Corporation (Mountain View, Calif., USA), and a plasmid with the correct sequence selected for DNA amplification. The gene deletion cassette was amplified using primers RRab 296 and RRab297.

```
RRab296 (Forward)
                                      (SEQ ID NO: 24)
5'-CACAGTTCGATCTACCTTACCTACA-3'

RRab297 (Reverse)
                                      (SEQ ID NO: 25)
5'-GCTGGGTTCTGAACCTGTAAAGTAC-3'
```

The PCR product was purified and concentrated using a QIAquick PCR purification kit (Qiagen Inc., Valencia, Calif., USA).

2.2 RLP37 Host Strain Transformation with ΔNik1::Hph Deletion Cassette, Candidate Selection, Verification and Characterization The purified concentrated Δnik1::hph cassette was transformed into the T. reesei host strain RLP37 using PEG-mediated transformation (Penttila, M., Nevalainen, H., Rätiö, M., Salminen, E., and Knowles, J. A versatile transformation system for the cellulolytic filamentous fungus Trichoderma reesei. Gene (1987) 61:155-164.). Transformants were plated on Vogel's minimal medium containing 100 μg/mL hygromycin B using overlays, and incubated at 28° C. Genomic DNA from stable transformants resistant to hygromycin B was extracted using NucleoSpin® PlantII kit (Machery-Nagel, Bethlehem, Pa., USA). This genomic DNA was then used as template for diagnostic PCRs to confirm homologous recombination of the deletion cassette at the native nik1 locus.

A strain with verified homologous integration of the Δnik1::hph deletion cassette labeled RLP37 Nik1$^{M743T}$ was selected and spore-purified. Spore-purification was performed by harvesting mature aerial conidiospores produced on a PDA plate culture in water, making 10× serial dilutions of the conidiospore suspension, plating the serial dilutions of the suspension on PDA plates and incubating them overnight at 28° C. The selected spore-purified strain was used for determining the effect of the gene replacement on protein production and remaining experiments. The phenotype of the RLP37 ΔNik1 strain on PDA plates consisted of slower growth and a lower yield of conidiospores when compared to the host RLP37 strain (FIGS. 3B and 3E). When sorbitol was added to Vogel's minimal medium colony growth of the strain was restricted compared to strain RLP37, indicating sensitivity to sorbitol possibly due to an inability to regulate a response to osmotic stress (FIGS. 3D and 3F).

2.3 Fermentation of T. reesei RLP37 ΔNik1 to Evaluate Total Protein Production

The RLP37 host strain and the RLP37 ΔNik1 strain were tested for the total protein production rate and yield on fed sugars in 2 L DASGIP fermentors. Seed cultures and fermentation procedures were performed in accordance with the same as described above in Example 1.

Figure 7A:
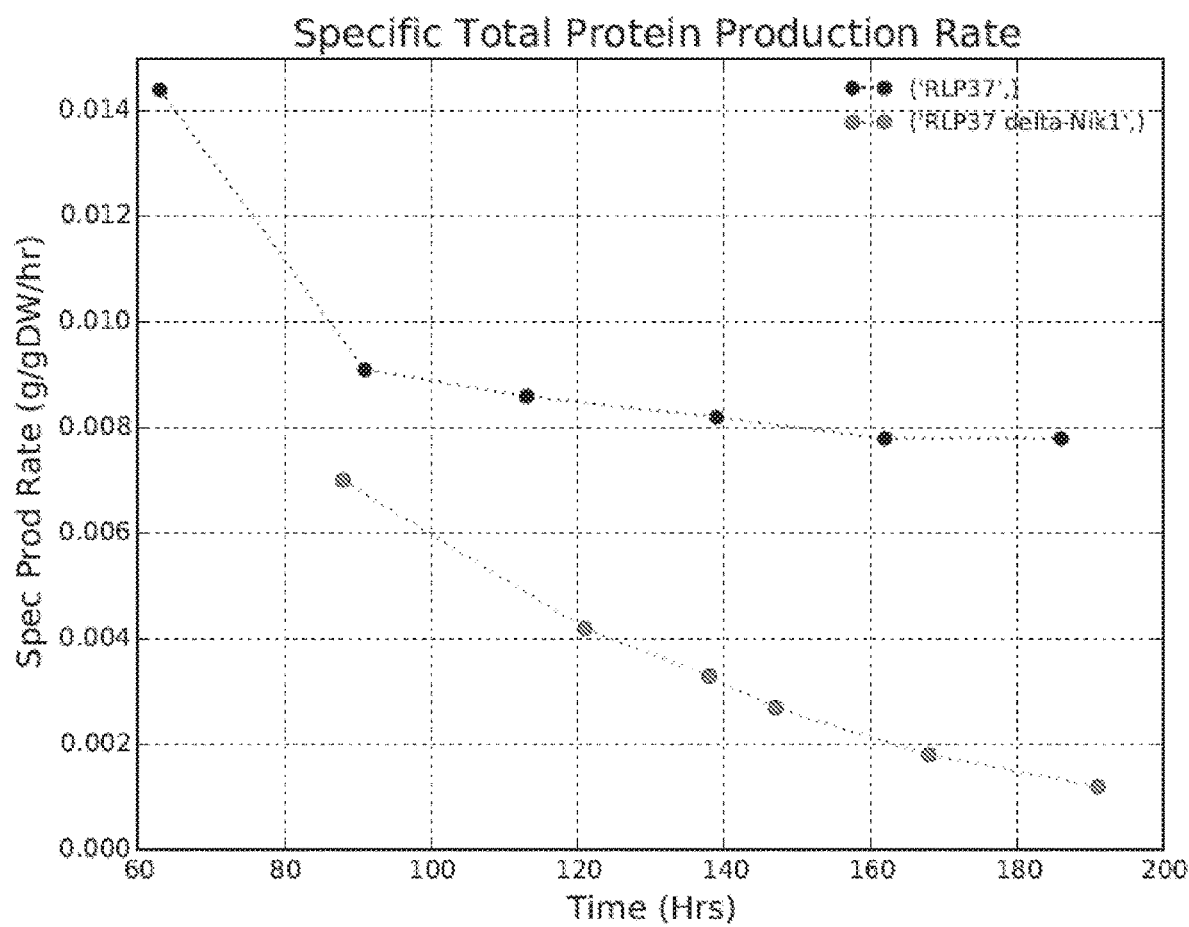
FIGS. 7A-7B. Compares the specific total protein production rate of RLP37 and RLP37 ΔNik1 during DASGIP 2 L scale fermentation.
Figure 7B:
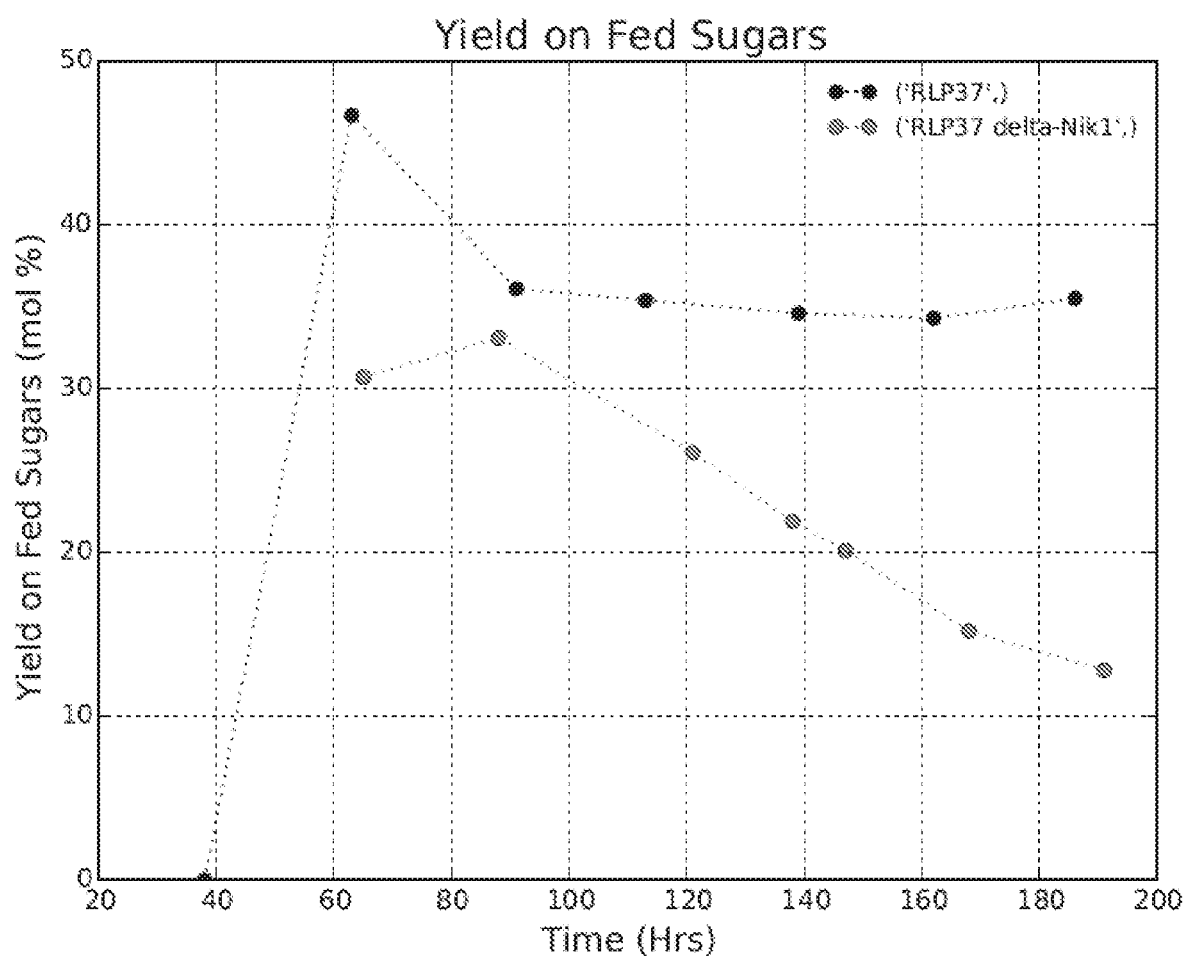

Dry cell weight, total protein concentrations and other parameters were measured, and specific total protein production rates and yield on fed sugars calculated. The total protein production rate of strain RLP37 ΔNik1 was reduced by 85%, and the yield on fed sugars by 39%, compared to the RLP37 control strain. This indicates that the deletion of the nik1 gene is detrimental to total protein production, and does not have the same effect as the replacement of the native nik1 allele with the nik1$^{M743T}$ allele. This also indicates that the nik1$^{M743T}$ allele is a gain-of-function allele resulting in a gain-of-function phenotype (FIG. 7).

Example 3

Engineered Fungal Strain as an Expression Host of a Cellulase of Interest 3.1 Transformation of *T. reesei* Host Strain Overexpressing CBH1 with Nik1$^{M743T}$ Allele-Containing Gene Replacement Cassette, Candidate Selection, Verification and Characterization The purified concentrated gene replacement cassette described in example 1.1 was transformed into a *T. reesei* host strain overexpressing CBH1 using PEG-mediated transformation (Penttila et al., Gene, 61(2):155-64 (1987)). Transformants were plated on Vogel's minimal medium containing 30 µg/mL hygromycin B using overlays, and incubated at 28° C. Genomic DNA from stable transformants resistant to 100 µg/mL hygromycin B was extracted using the NucleoSpin® PlantII kit (Machery-Nagel, Bethlehem, Pa., USA). This genomic DNA was then used as template for diagnostic PCRs to confirm homologous recombination of the gene replacement at the native nik1 locus. The primer pairs RRab117 (SEQ ID NO:14) and RRab167 (SEQ ID NO:15) were used for diagnostic PCR.

A strain with verified homologous integration of the nik1$^{M743T}$-containing gene replacement cassette labeled Cbh1 Nik1$^{M743T}$ was selected and spore-purified. Spore-purification was performed by harvesting mature aerial conidiospores produced on a PDA plate culture in water, making 10× serial dilutions of the conidiospore suspension, plating the serial dilutions of the suspension on PDA plates and incubating them overnight at 28° C. The selected spore-purified strain was used for determining the effect of the gene replacement on protein production and remaining experiments.

When sorbitol was added to Vogel's minimal medium, colony growth of the Cbh1 Nik1$^{M743T}$ strain was restricted, indicating sensitivity to sorbitol possibly due to an inability to regulate a response to osmotic stress (FIGS. 8E-8H). The native nik1$^{WT}$ was replaced with the nik1$^{M743T}$ allele in the *T. reesei* strain that does not overexpress the CBH1 cellulase (NoCbh1). It showed the same response to sorbitol, confirming that the nik1$^{M743T}$ is responsible for this response (FIGS. 8A-8D).

3.2 Fermentation of *T. reesei* Cbh1 Nik1$^{M743T}$ to Evaluate Total Protein Production

*Trichoderma reesei* CBH1 overexpression strain as described above and *Trichoderma reesei* Cbh1 Nik1$^{M743T}$ were grown under identical conditions in submerged (liquid) culture. The respective specific total protein production rates and yields on fed sugar were compared in 2 L (DASGIP) and 14 L scale fermentors.

To create a seed culture, the spores of each strain were added separately to 50 mL of citrate minimal medium in a 250 mL flask. The cultures were grown for 48 h at 30° C. and 170 rpm in a shaking incubator. After 48 h, 145.6 mL of 50% glucose, and 0.6 g/kg of CaCl$_2$, adjusted to pH 3.5, was inoculated with the seed culture. Thereafter, the temperature was maintained at 32° C., and pH at 3.5. A glucose-sophorose feed was thereafter introduced, and the temperature was dropped to 28° C., pH increased to 4.5.

Figure 9A:
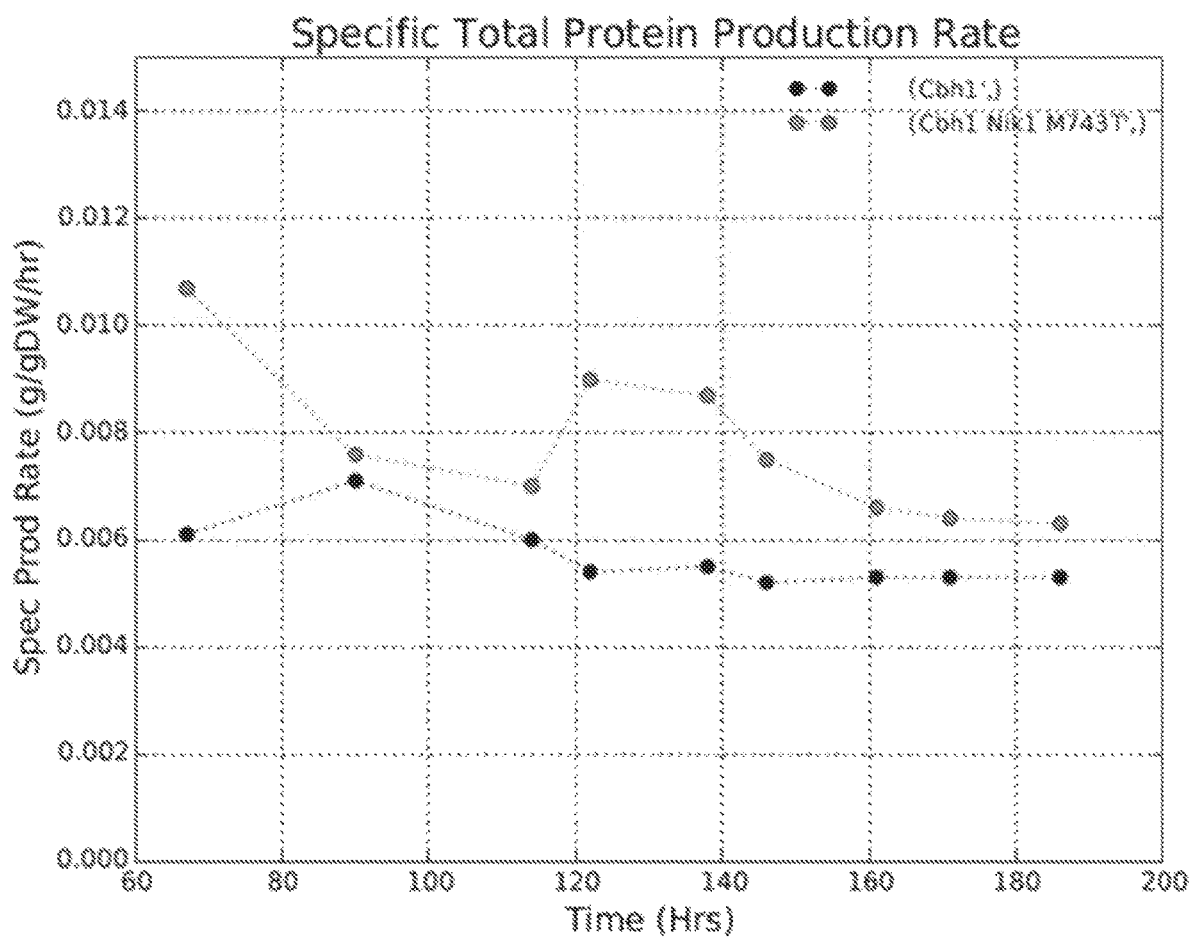
FIGS. 9A-9B. Compares the protein production of Cbh1 and Cbh1 Nik1$^{M743T}$ in DASGIP 2 L scale fermentation.
Figure 9B:
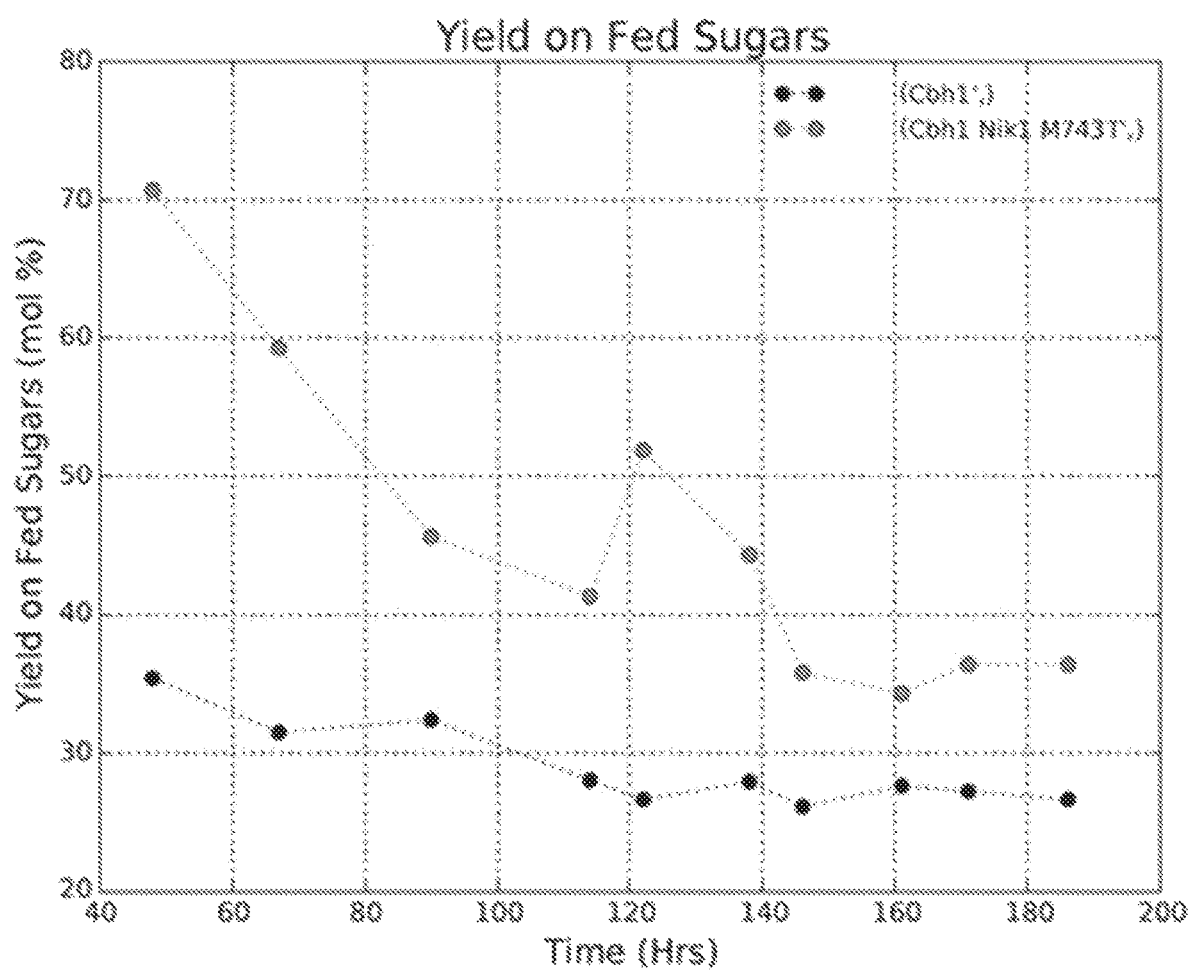

Dry cell weight, total protein concentrations and other parameters were measured, and specific total protein production rates and yield on fed sugars calculated. The Cbh1 Nik1$^{M743T}$ strain showed a 19% improvement in total specific protein production rate, and a 46% improvement in yield on fed sugars over strain Cbh1 (FIG. 9).

For 14 L fermentations, *Trichoderma reesei* Cbh1 strain and *Trichoderma reesei* Cbh1 Nik1$^{M743T}$ were grown under identical conditions in submerged (liquid culture), and their total protein production and specific protein production rates were compared. Fermentation runs were carried out using a similarly prepared seed culture, and in 14 L fermenters. Post fermentation, total protein production and specific protein production rates were compared.

Figure 10A:
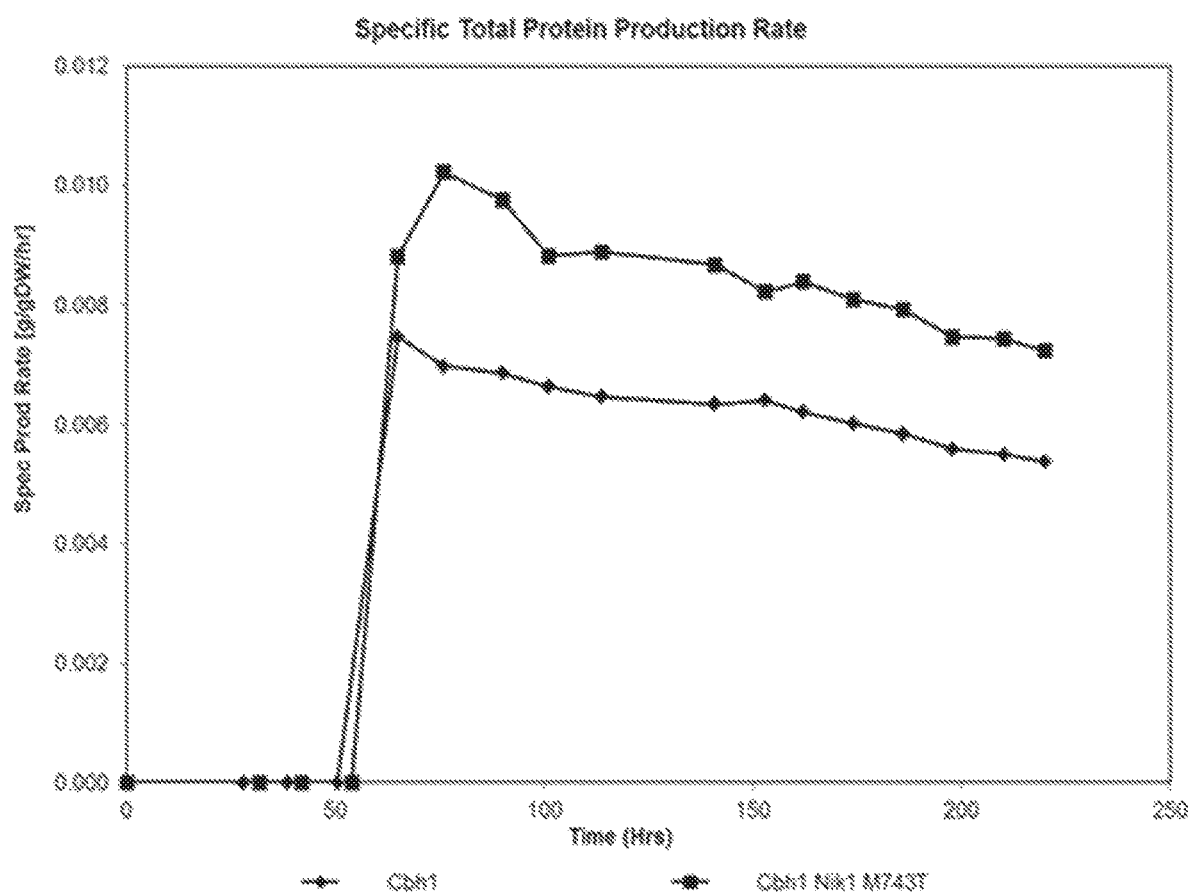
FIGS. 10A-10B. Compares the protein production of Cbh1 and Cbh1 Nik1$^{M743T}$ in 14 L scale standard fungal fermentation.
Figure 10B:
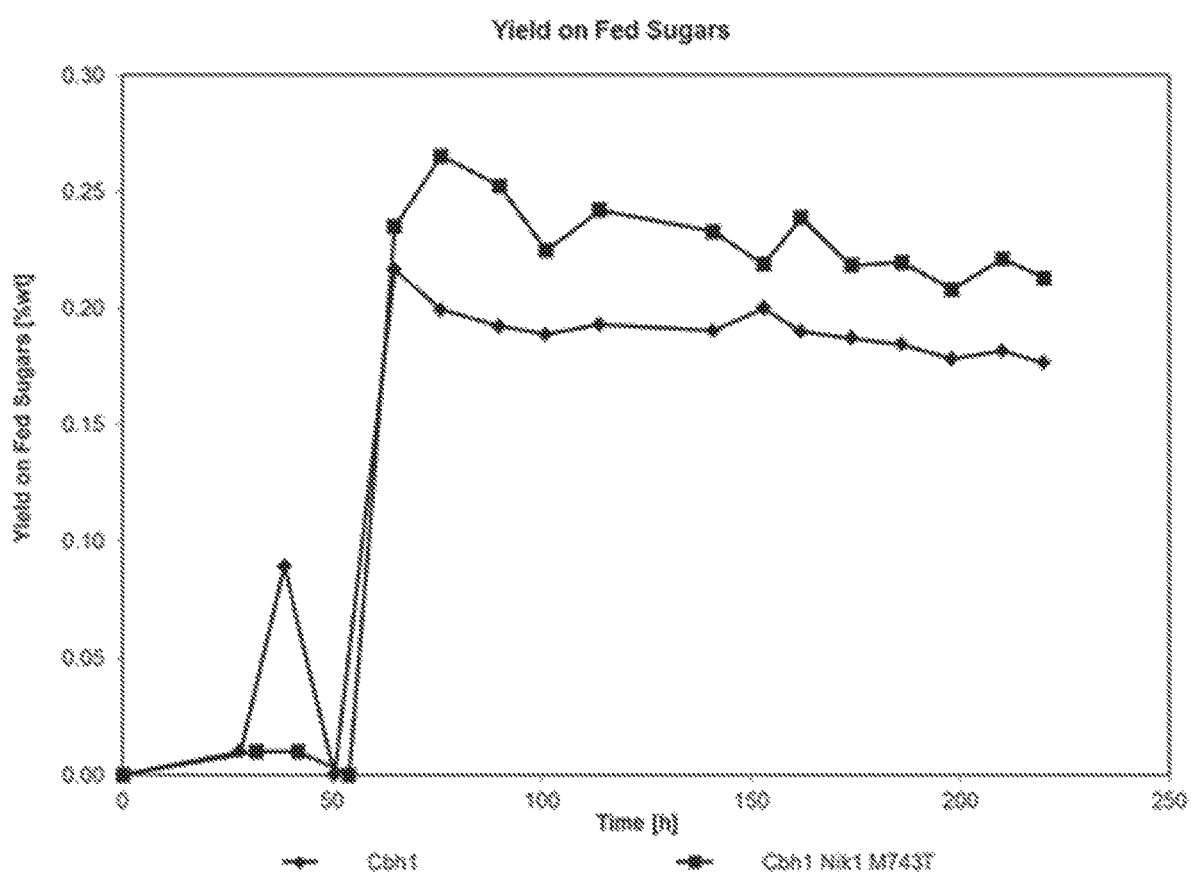

The Cbh1 Nik1$^{M743T}$ strain showed a 30% increase in total protein specific production rate (FIG. 10A), and a 20% improvement in yield on fed sugars (FIG. 10B) over Cbh1 strain, indicating that introducing the modified nik1 histidine kinase into a *T. reesei* CBH1 overexpressing strain causes an increase in protein production.

Example 4

Figure 11:
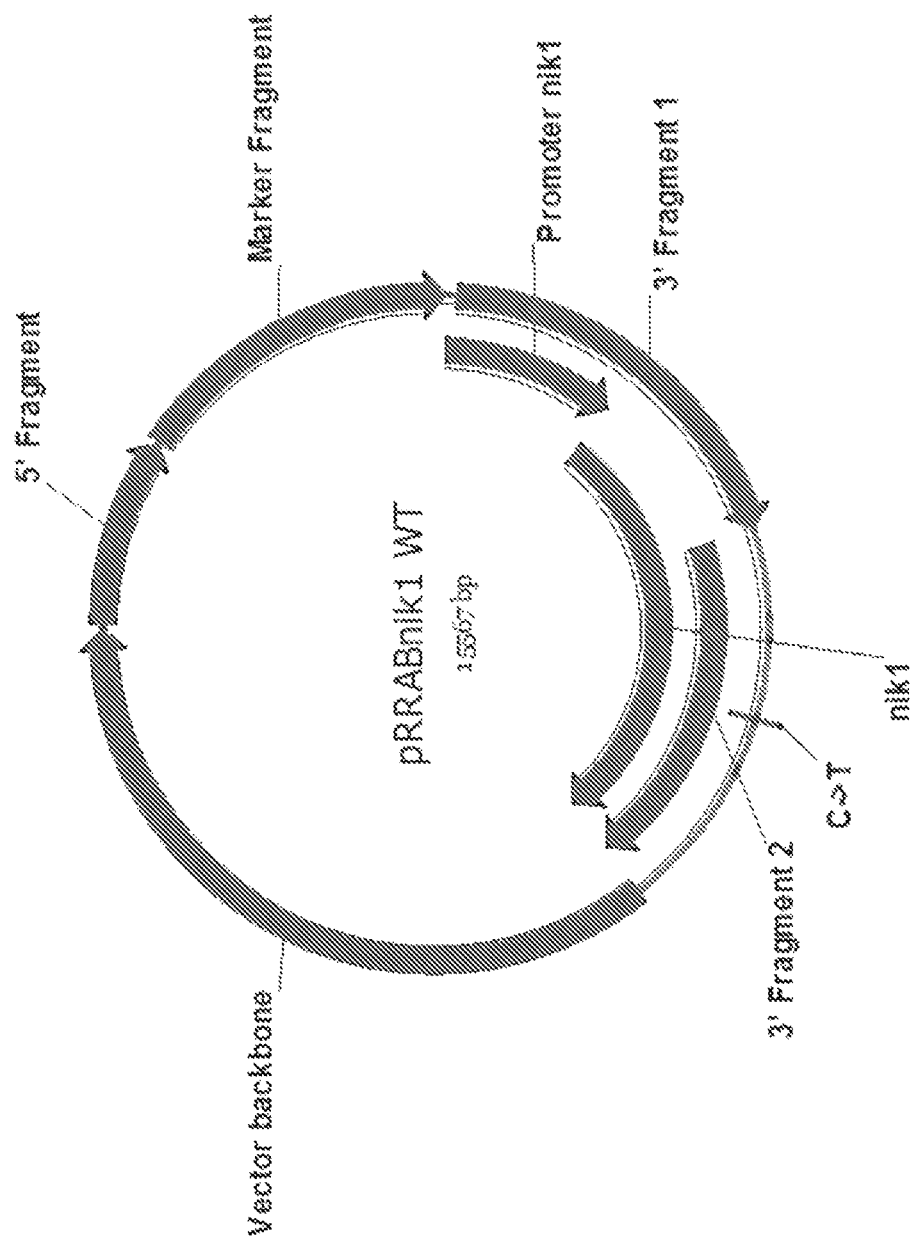
FIG. 11. Depicts a map of pRRAB nik1$^{WT}$ with the gene replacement cassette containing the nik1$^{WT}$ allele.

Reversion of the Gain-of-Function Phenotype by Replacement of Nik1$^{M743T}$ Allele with Nik1$^{wt}$ Allele in a *T. reesei* Host 4.1 Nik1$^{WT}$ Gene Replacement Cassette Design and Creation A gene replacement construct was prepared (FIG. 11) by fusing a DNA fragment containing the 5' region upstream of the nik1 locus, a loxP-flanked hygromycin B-resistance cassette and a DNA fragment containing the promoter and nik1 wild type gene, with the 2µ backbone-containing yeast vector pRS426 (from pRS426 phagemid in *E. coli*, ATCC® 77107™).

Primer pairs, RRab88 (SEQ ID NO:2) and RRab89 (SEQ ID NO:3); RRab90 (SEQ ID NO:4) and RRab91 (SEQ ID NO:5); RRab92 (SEQ ID NO:6) and RRab93 (SEQ ID NO:7); RRab94 (SEQ ID NO:8) and RRab95 (SEQ ID NO:9); RRab110 (SEQ ID NO:10) and RRab111 (SEQ ID NO:11) were used to amplify the DNA fragments (as described in Example 1.1, above).

PCR amplifications were performed using the PfuUltraII Fusion HS DNA polymerase (Agilent Technologies, Santa Clara, Calif., USA) and a Tetrad 2 thermal cycler (Bio-Rad, Hercules, Calif., USA). PCR products were separated on EX gels (Life Technologies, Grand Island, N.Y., USA), and fragments of the correct length were purified using the QIAquick Gel Extraction kit (Qiagen Inc., Valencia, Calif., USA). Each of the four DNA fragments had a 5' primer extension complementary to the adjacent DNA fragment to provide a sufficient length of homologous sequence for recombination, and all were recombined into the final construct in the *Saccharomyces cerevisiae* strain YPH499 (ATCC 76625) using the yeast's native recombination machinery. The Frozen EZ Yeast Transformation II™ kit (Zymo Research, Orange, Calif., USA) was used for yeast transformations. Transformants were plated on SD-U plates to select for complementation of uridine auxotrophy. Individual colonies from the transformation plates were selected to extract plasmid DNA using the Zymoprep™ Yeast Plasmid Miniprep II kit (Zymo Research, Orange, Calif., USA).

From each miniprep 1 µL was directly transformed into One Shot® TOP10 chemically competent *E. coli* cells (Life Technologies, Grand Island, N.Y., USA), and plated on LB plates with carbenicillin. Individual colonies from the transformation plates were selected to extract plasmid DNA using the QIAprep Spin Miniprep kit (Qiagen Inc., Valencia, Calif., USA). DNA obtained this way was sequenced at Sequetech Corporation (Mountain View, Calif., USA), and a plasmid with the correct sequence selected for DNA amplification. The gene replacement cassette was amplified using primers RRa156 (SEQ ID NO:12) and RRab157 (SEQ ID NO:13), and the PCR product was purified and concentrated using a QIAquick PCR purification kit (Qiagen Inc., Valencia, Calif., USA).

4.2 *T. reesei* Strain TR Nik1$^{M743T}$ Transformation with Nik1$^{WT}$ Allele-Containing Gene Replacement Cassette, Candidate Selection, Verification and Characterization The purified concentrated nik1$^{WT}$-containing gene replacement cassette was transformed into the *T. reesei* TR Nik1$^{M743T}$ host strain containing nik1$^{M743T}$ at the native nik1 locus, using PEG-mediated transformation (Penttila et al., Gene, 61(2):155-64 (1987)). The TR Nik1$^{M743T}$ host strain was derived from strain RLP37. Transformants were plated on Vogel's minimal medium (Vogel, Microbial Genet. Bull. 13:42-43 (1956); Vogel, Am. Nat. 98:435-446 (1964)) containing 30 μg/mL hygromycin B using overlays, and incubated at 28° C. Genomic DNA from stable transformants resistant to 100 μg/mL hygromycin B was extracted using a NucleoSpin® PlantII kit (Machery-Nagel, Bethlehem, Pa., USA). This genomic DNA was then used as template for diagnostic PCRs to confirm homologous recombination of the gene replacement at the native nik1 locus. The primer pairs RRab117 (SEQ ID NO:14) and RRab167 (SEQ ID NO:15) were used for diagnostic PCR.

A strain with verified homologous integration of the nik1$^{WT}$-containing gene replacement cassette at the native nik1 locus was selected, labeled TR Nik1$^{WT}$, and spore-purified. Spore-purification was performed by harvesting mature aerial conidiospores produced on a PDA plate culture in water, making 10× serial dilutions of the conidiospore suspension, plating the serial dilutions of the suspension on PDA plates and incubating them overnight at 28° C. The selected spore-purified strain was used for determining the effect of the gene replacement on protein production and remaining experiments. The phenotype of the TR Nik1$^{WT}$ strain on Vogel's minimal medium plates consisted of faster growth and a higher yield of conidiospores when compared to the TR Nik1$^{M743T}$ strain (FIGS. 8I and 8J).

Figure 8:
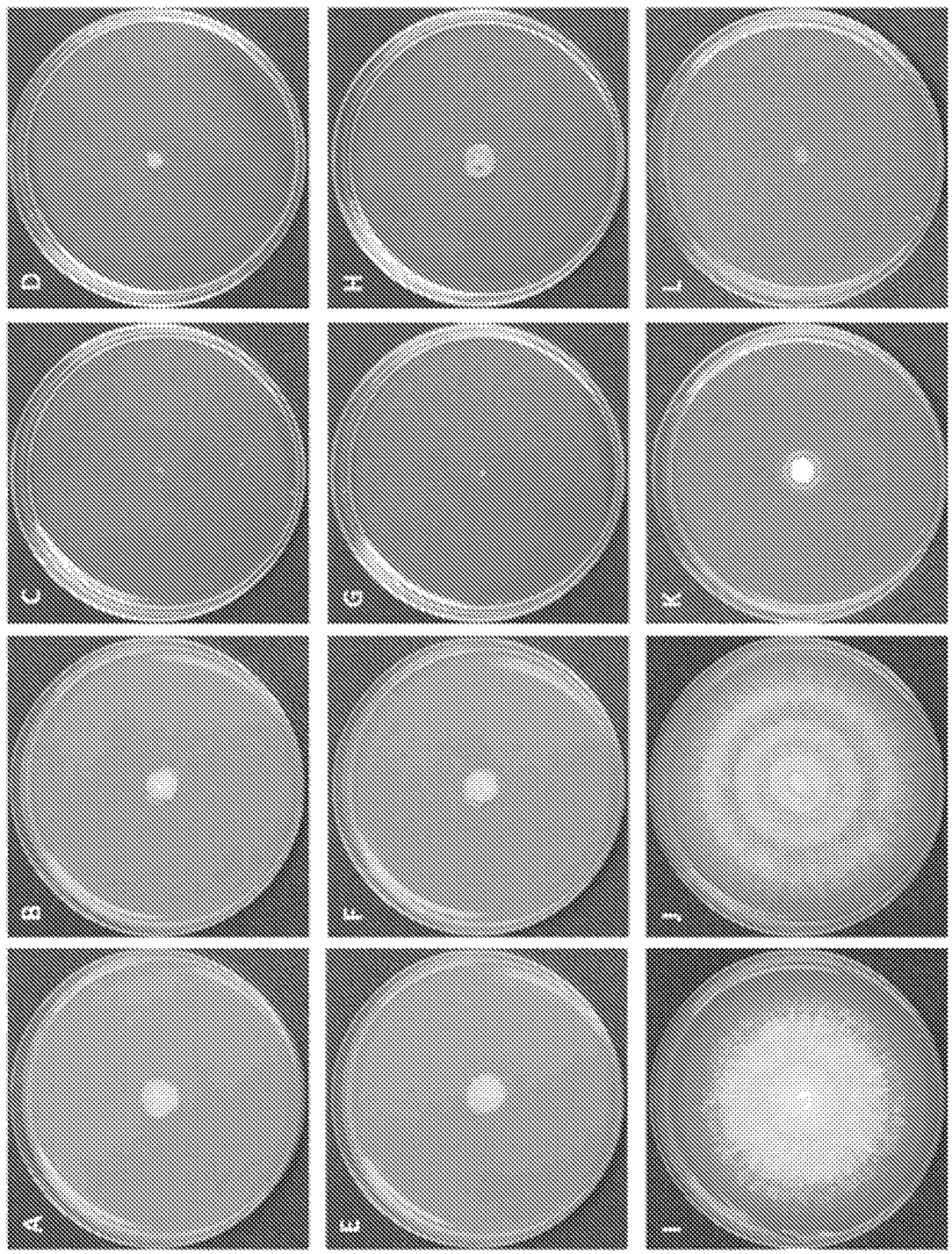
FIGS. 8A-8L. Compares colony phenotypes of various strains on various media.

When sorbitol was added to Vogel's minimal medium colony growth of the strain was not restricted compared to TR Nik1$^{M743T}$, indicating that the sensitivity to sorbitol possibly due to an inability to regulate a response to osmotic stress was reverted (FIGS. 8K and 8L).

4.3 Fermentation of *T. reesei* Nik1$^{WT}$ to Evaluate Total Protein Production

*Trichoderma reesei* strains TR Nik1$^{WT}$, and TR Nik1$^{M743T}$ were grown under identical conditions in submerged (liquid) culture, and their specific total protein production rates and yields on fed sugar were compared in 2 L (DASGIP) fermentors.

To create a seed culture, the spores of each strain were added separately to 50 mL of citrate minimal medium in a 250 mL flask. The cultures were grown for 48 h at 30° C. and 170 rpm in a shaking incubator. After 48 h, 145.6 mL of 50% glucose, and 0.6 g/kg of CaCl2, adjusted to pH 3.5 was inoculated with the seed culture. Thereafter, the temperature was maintained at 30° C., and pH at 3.5. A glucose-sophorose feed was thereafter introduced, and the temperature was dropped to 25° C., pH increased to 4.8.

Dry cell weight, total protein concentrations and other parameters were measured, and specific total protein production rates and yield on fed sugars calculated. The TR Nik1$^{WT}$ strain containing the nik1$^{WT}$ allele at the native nik1 locus showed a 36% reduction in the specific total protein production rate and a 29% reduction in yield on fed sugars compared to the TR Nik1$^{M743T}$ strain containing the nik1$^{M743T}$ allele at the nik1 locus (FIG. 12). This showed that replacing the nik1$^{M743T}$ allele with the native nik1$^{WT}$ allele returns the gain-of-function phenotype to the wild type phenotype, confirming that the nik1$^{M743T}$ allele alone is responsible for the improved total protein production rate and yield on fed sugars.

Example 5

Screening for Osmotic Sensitivity or Resistance, and Improved Secreted Protein Productivity Any method may be employed to create a population of *Trichoderma reesei* mutated cells. For example, conidiospores may be obtained from a strain of *T. reesei* and subjected to treatment with UV irradiation, X-ray irradiation, gamma-ray irradiation or chemical mutagenesis with a mutagenic agent such as NTG (N-methyl-N'-nitro-N-nitrosoguanidine) or EMS (ethylmethanesulfonate) (Davis, R. H. and De Serres, F. J. (1970) Genetic and microbiological research techniques for *Neurospora crassa*. In, Methods in Enzymology Vol17A. Eds. Tabor, H. and Tabor, C. W. pp 79-143). Alternatively, spontaneous mutation may be relied upon. Additionally, molecular biology methods of mutagenesis such as insertional mutagenesis via *Agrobacterium* transformation may be employed (Sugui, J. A., Chang, Y. C. and Kwon-Chung, K. J. (2005) Appl. Environ. Microbiol. 71:1798-17802).

The population of mutated cells is subjected to a screen to identify those with altered sensitivity to high osmotic pressure. The altered sensitivity may manifest itself as an ability to grow faster than the parent non-mutated cell under conditions of high osmotic pressure (i.e., resistance to high osmotic pressure) or as a reduced growth rate compared to the parent, non-mutated cell under conditions of high osmotic pressure (i.e., sensitivity to high osmotic pressure).

To screen for altered sensitivity to high osmotic pressure, *T. reesei* cells are inoculated onto the surface of nutrient agar plates with various levels of added sugars, sugar alcohols or salts such that individual colonies arise and can be distinguished upon culture. The nutrient agar is Vogel's minimal medium with glucose (Vogel, Microbial Genet. Bull. 13:42-43 (1956); Vogel, Am. Nat. 98:435-446 (1964)). This medium is supplemented with 1M-1.2M sorbitol, or 0.7M-1.4M sodium chloride, or 0.5M-1.4M potassium chloride. Individual colonies that grow faster or slower than the parental type are picked for further evaluation by growth under identical conditions in submerged (liquid culture) and their specific total secreted protein production rates and yields on fed sugar compared. In this way, mutant strains of *T. reesei* are identified that have altered sensitivity to osmotic pressure and increased secreted protein production rates compared to a parental strain.

Example 6

Screening or Selecting for Resistance to Fungicide and Improved Secreted Protein Productivity Any method may be employed to create a population of *Trichoderma reesei* mutated cells. For example, conidiospores may be obtained from a strain of *T. reesei* and subjected to treatment with UV irradiation, X-ray irradiation, gamma-ray irradiation or chemical mutagenesis with a mutagenic agent such as NTG (N-methyl-N'-nitro-N-nitrosoguanidine) or EMS (ethylmethanesulfonate) (Davis, R. H. and De Serres, F. J. (1970) Genetic and microbiological research techniques for *Neurospora crassa*. In, Methods in Enzymology Vol17A. Eds. Tabor, H. and Tabor, C. W. pp 79-143). Alternatively, spontaneous mutation may be relied upon. Additionally, molecular biology methods of mutagenesis such as insertional mutagenesis via *Agrobacterium* transformation may be employed (Sugui, J. A., Chang, Y. C. and Kwon-Chung, K. J. (2005) Appl. Environ. Microbiol. 71:1798-17802).

The population of mutated cells can also be subjected to a screen to identify those with altered sensitivity to a dicarboximide and phenylpyrrole fungicides such as iprodione or fludioxonil in the medium. The altered sensitivity may manifest itself as an ability to grow faster than the parent non-mutated cell in the presence of the fungicide (i.e. resistance to fungicide), or as a reduced growth rate compared to the parent non-mutated cell in the presence of the fungicide (i.e. sensitivity to fungicide).

To select for resistance to iprodione or fludioxonil, *T. reesei* cells are inoculated onto the surface of nutrient agar plates with various levels of these fungicides such that individual colonies arise and can be distinguished upon culture. The nutrient agar is Vogel's minimal medium with glucose (Vogel, Microbial Genet. Bull. 13:42-43 (1956); Vogel, Am. Nat. 98:435-446 (1964)). Individual colonies that grow faster than the parental type are picked for further evaluation by growth under identical conditions in submerged (liquid culture) and their specific total secreted protein production rates and yields on fed sugar compared. In this way, mutant strains of *T. reesei* are identified that are resistant to iprodione or fludioxonil and have increased secreted protein production rates compared to a parental strain.

For use in liquid medium fungicide screens, conidiospores from *T. reesei* strains RLP37 and RLP37 NikM743T were harvested and diluted to a concentration of 10,000/ml. Equal numbers of spores were inoculated into liquid YEG medium (5 g/L yeast extract, 22 g/1 glucose. H2O) containing 0, 11.25, 22.5, 45 or 90 µM iprodione or fludioxonil and allowed to germinate overnight at 28° C. RLP37 conidiospores germinated and produced elongated hyphae in medium with no iprodione or fludioxonil. At 11.25 µM iprodione or fludioxonil germination of this strain was apparent but there was clear inhibition of hyphal growth. At concentrations of iprodione or fludioxonil above 11.25 µM there was complete inhibition of germination and growth with strain RLP37. In contrast, RLP37 NikM743T conidiospores germinated and produced elongated hyphae at all concentrations of iprodione or fludioxonil tested. This clearly demonstrated that the NikM743T mutation confers resistance to the fungicides iprodione and fludioxonil. Furthermore, sensitivity of RLP37 and resistance of RLP37 NikM743T persisted when inoculation culture was scaled up to 107 spores/ml.

Figure 13:
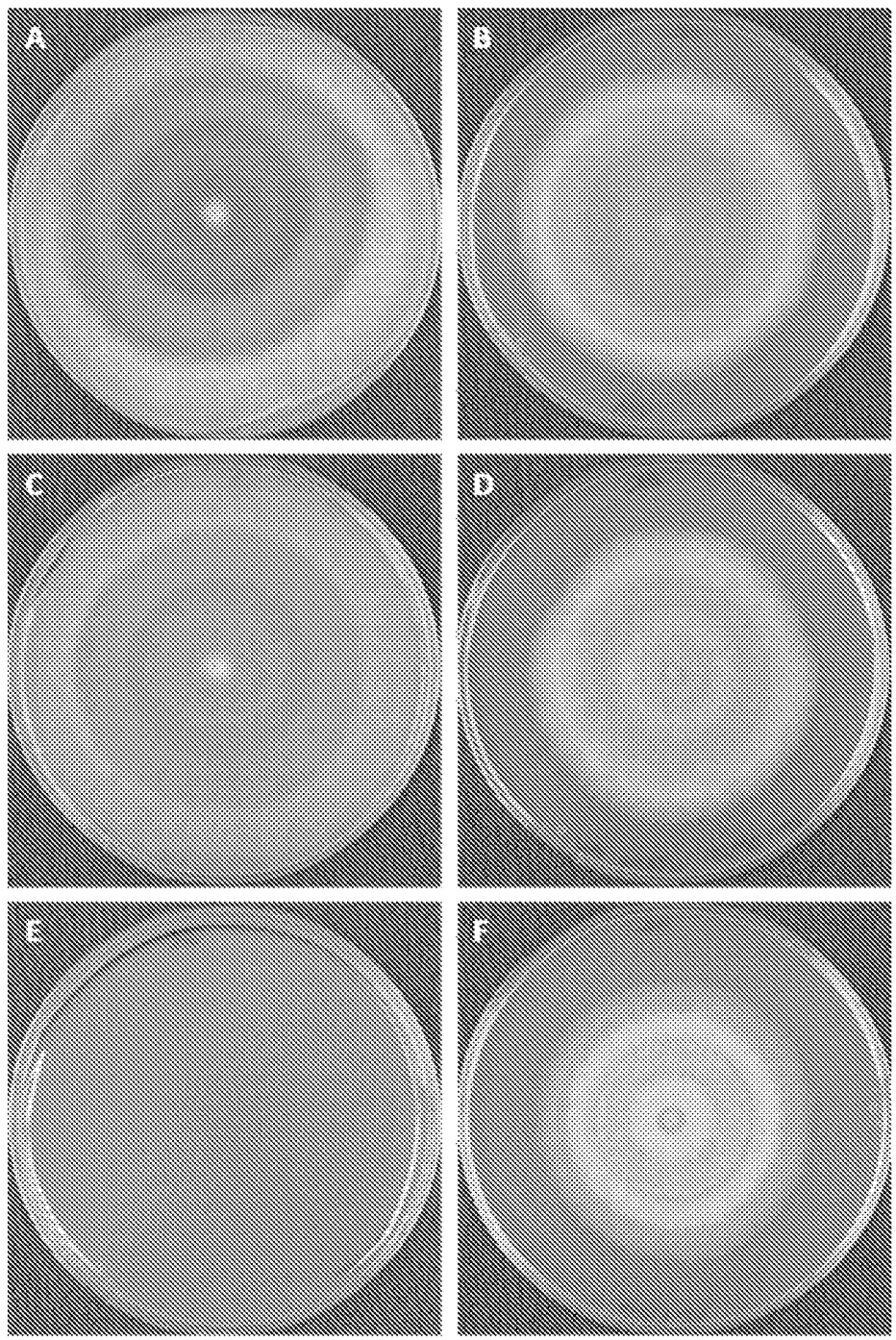
FIG. 13. Compares phenotypes of *T. reesei* strains RLP37 and RLP37 Nik1$^{M743T}$ on media with or without fungicide.

For use in agar (solid) medium fungicide screens or selections, conidiospores from *T. reesei* strains RLP37 and RLP37 Nik$^{M743T}$ were harvested and diluted to a concentration such that a known number of spores were plated per 10 cm plate containing nutrient agar Vogel's minimal medium with glucose (Vogel, Microbial Genet. Bull. 13:42-43 (1956); Vogel, Am. Nat. 98:435-446 (1964)). Equal numbers of spores for each strain were spread onto the surface of nutrient agar plates containing 0, 11.25, 22.5, 45 or 90 µM iprodione and allowed to grow for 3 days at 32° C. At 11.25 and 22.5 µM, RLP37 colonies failed to grow to any larger than the size of the tip of a pin. At 45 µM and above, RLP37 colonies failed to grow at all. In contrast, RLP37 Nik$^{M743T}$ colonies grew similarly to colonies growing on nutrient agar plates without iprodione. This clearly demonstrated that the nik1$^{M743T}$ mutation confers resistance to iprodione in solid agar media (FIG. 13). To establish the sensitivity of iprodione in selecting for nik1 mutants occurring infrequently in a large population of cells containing wild type nik1, a known number of RLP37 Nik$^{M743T}$ spores (down to 5 spores) were mixed into a known, much higher number of RLP37 ($10^5$-$10^8$). This mixed population of spores was spread onto Vogel's minimal medium agar containing 45 µM iprodione and allowed to grow for 3 days at 32° C. Colonies were counted and evaluated for presence of the nik1$^{M743T}$ mutation by PCR and sequencing (Sequetech, Mountain View, Calif., USA), using the following primers:

```
RRab126 (forward)
                              (SEQ ID NO: 40)
5'-CGGCATGGCCATGAACCTCA-3'

RRab161 (reverse)
                              (SEQ ID NO: 41)
5'-GCACTGAAGCCGGTTAGTTC-3'

RRab128 (forward)
                              (SEQ ID NO: 42)
5'-CTGTCCAGCTTCTGCTACGA-3'
```

Selective plating on 45 µM iprodione is sensitive enough to detect as few as 5 mutants in $10^6$ wild type spores. High false positive rates occur when plating more than $10^6$ spores per 10 cm plate.

Since the nik1$^{M743T}$ mutation confers sorbitol sensitivity as well as iprodione resistance, a depletion of non-sorbitol sensitive spores may enrich for nik1 mutants with desired features. RLP37 and RLP37 Nik$^{M743T}$ were grown up in YEG containing 1.2 M sorbitol overnight at 28° C. and then filtered through 4 layers of Miracloth (VWR, Radnor, Pa., USA) prior to plating known numbers of spores on Vogel's minimal medium agar containing 45 µM iprodione. The Miracloth filtration resulted in a 98% reduction in number of RLP37 colonies compared to unfiltered RLP37. In contrast, only a 2-8% reduction was observed for RLP37 Nik$^{M743T}$ post-filtration. However, although >90% of RLP37 Nik$^{M743T}$ spores passed through the Miracloth filter, only 1-2% of RLP37 Nik$^{M743T}$ spores that came through filtration were able to be recovered on plates. Depending on the frequency of spontaneous mutation in nik1, this depletion method may offer an advantage prior to selection on agar plates containing iprodione. If enough mutants were accumulated, although the sorbitol depletion may eliminate the majority of mutants, there is also a reduction in false positives from filtering wild-type spores that germinate under sorbitol, therefore increasing the potential throughput. Sorbitol sensitivity and dicarboximide fungicide resistance are both features associated with desired outcome in protein productivity, so by combining the sorbitol depletion method with selection on fungicide plates, the potential increase in throughput may improve the chances of identifying spontaneous mutants with desired specific productivity.

To select for cells spontaneously mutated to have fungicide resistance, conidiospores from *T. reesei* strain RLP37 were harvested and diluted such that $10^6$ spores were spread onto the surface of each nutrient agar plates containing 45 µM iprodione. The nutrient agar is Vogel's minimal medium with glucose (Vogel, Microbial Genet. Bull. 13:42-43 (1956); Vogel, Am. Nat. 98:435-446 (1964)). Individual colonies that grew were picked for further evaluation by sequencing of the nik1 locus. Colonies resistant to fungicide contained at least one mutation in the coding region of nik1.

By this method, iprodione resistant mutant strains of *T. reesei* containing mutations in nik1 were obtained.

Example 7

Figure 14:
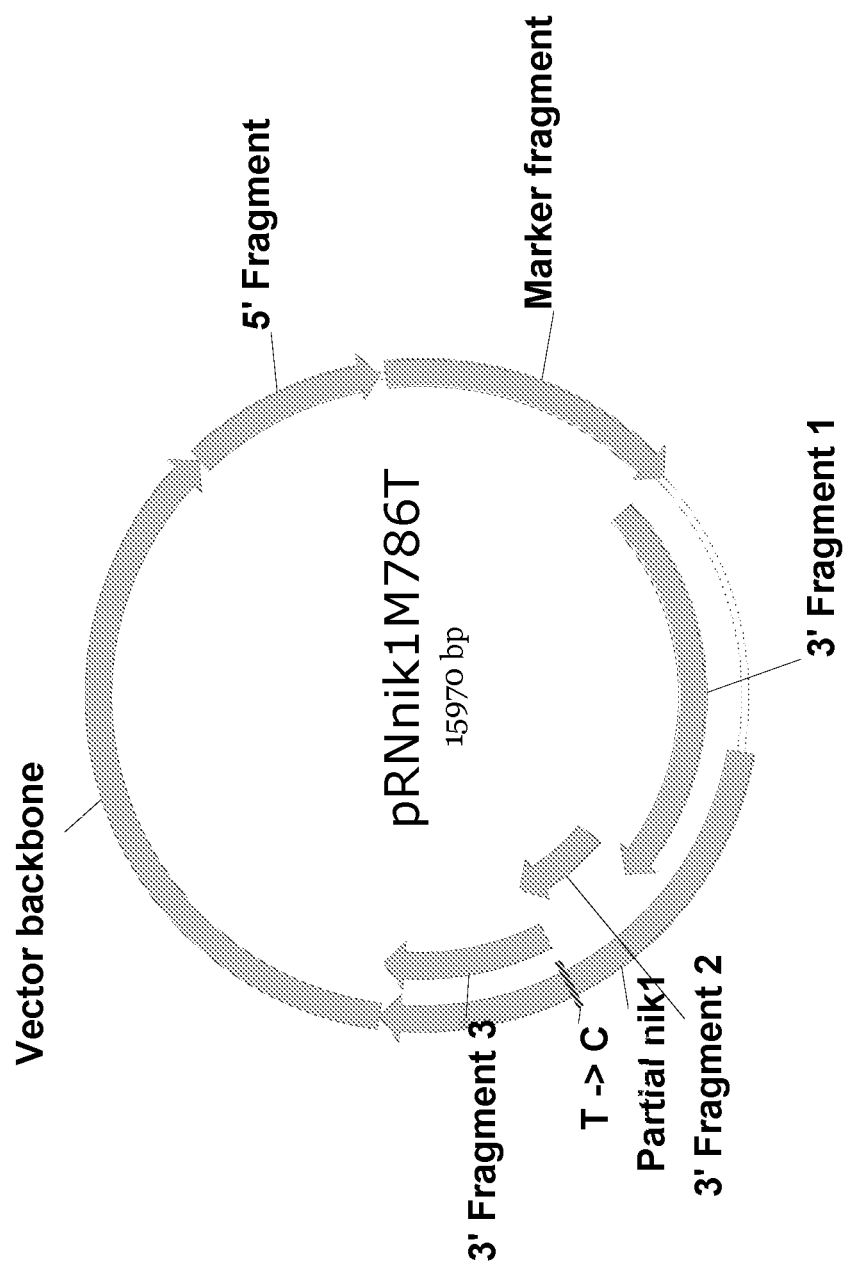
FIG. 14. Depicts a map of pRNnik1$^{M786T}$ with the gene replacement cassette containing the *Aspergillus niger* nik1$^{M786T}$ allele.

Creating an Engineered *Aspergillus niger* Strain with One Mutation in Nik1 Gene 7.1 Generation of Nik1$^{M786T}$ Gene Replacement Cassette A gene replacement construct was made (FIG. 14) by fusing a DNA fragment containing the 5' region upstream of the nik1 locus, a pyrG marker cassette, and three DNA fragments containing the promoter and nik1 gene (including the T to C substitution that changes the amino acid at position 786 from methionine to threonine), with the 2μ backbone-containing yeast vector pRS426 (from pRS426 phagemid in *E. coli*, ATCC® 77107™).

The following primers were prepared by Integrated DNA Technologies, Inc. (Coralville, Iowa, USA):

RN0286 (Forward)—5'-CGATAAGCTTGATATCGAAT-TCCTGGTTCCTGAATAGACTTGGGGTTG-3' (SEQ ID NO:26), which was used to amplify the DNA sequence upstream of nik1 (5' Fragment) for plasmid pRNnik1M786T, and contains a vector backbone tail overhang.

RN0508 (Reverse)—5'-CCGGGTACCGAGCTCGAAT-TCGTAATCATGGGCCCAGTACTAGATAGATACCTG-3' (SEQ ID NO:27), which was used to amplify the DNA sequence upstream of nik1 (5' Fragment) for plasmid pRNnik1M786T, and contains a pyrG marker cassette tail overhang.

RN0428 (Forward)—5'-GCCAGTGCCAAGCTTAT-CACC-3' (SEQ ID NO:28), which was used to amplify the pyrG marker cassette for plasmid pRNnik1M786T.

RN0172 (Reverse)—5'-CCATGATTACGAAT-TCGAGCT-3' (SEQ ID NO:29), which was used to amplify the pyrG marker cassette for plasmid pRNnik1M786T.

RN0509 (Forward)—5'-GATAAGGGACGGTGA-TAAGCTTGGCACTGGCGGATTTGCTGCCAGCTT-TAC-3' (SEQ ID NO:30), which was used to amplify the DNA sequence upstream of nik1 and the 5' end of nik1 (3' Fragment 1) for plasmid pRNnik1M786T, and contains a pyrG cassette tail overhang.

RN489 (Reverse)—5'-CTTCAACTCTGCGATCTC-TCC-3' (SEQ ID NO:31), which was used to amplify the DNA sequence upstream of nik1 and the 5' end of nik1 (3' Fragment 1) for plasmid pRNnik1M786T.

RN0495 (Forward)—5'-CACGGTTACCAAGGCTG-TGG-3' (SEQ ID NO:32), which was used to amplify nik1 (3' Fragment 2) for plasmid pRNnik1M786T.

RN0498 (Reverse)—5'-CCAATGATACCGTTCGTG-GGCGTCCGGATCTCG-3' (SEQ ID NO:33), which was used to amplify nik1 (3' Fragment 2) for plasmid pRNnik1M786T, and incorporate the M786T mutation.

RN0161 (Forward)—5'-CCGGACGCCCACGAACG-GTATCATTGGTATGACGCAGTTGAC-3' (SEQ ID NO:34), which was used to amplify nik1 (3' Fragment 3) for plasmid pRNnik1M786T, and incorporate the M786T mutation.

RN0182 (Reverse)—5'-CGGTGGCGGCCGCTCTAGA-ACTAGTGGATCGGGTGCATTTCACCACTACTTGAG-3' (SEQ ID NO:35), which was used to amplify nik1 (3' Fragment 3) for plasmid pRNnik1M786T, and contains a vector backbone overhang.

PCR amplifications were performed using the PfuUltraII Fusion HS DNA polymerase (Agilent Technologies, Santa Clara, Calif., USA) and a Tetrad 2 thermal cycler (Bio-Rad, Hercules, Calif., USA). PCR products were separated on E-gels (Life Technologies, Grand Island, N.Y., USA), and fragments of the correct length were purified using the QIAquick Gel Extraction kit or QIAquick PCR Purification kit (Qiagen Inc., Valencia, Calif., USA). The vector backbone was linearized by digestion with BamHI (Thermo Scientific, Grand Island, N.Y., USA), followed by de-phosphorylation by Alkaline Phosphatase (Roche, Indianapolis, Ind., USA), and purification using the QIAquick PCR Purification kit.

Each of the five DNA fragments contain sequences on both ends that overlap sequence of adjacent DNA fragments to provide a sufficient length of homologous sequence for recombination, and all were recombined into the final construct in the *Saccharomyces cerevisiae* strain YPH499 (ATCC 76625) using the yeast's native recombination machinery. The Frozen EZ Yeast Transformation II™ kit (Zymo Research, Orange, Calif., USA) was used for yeast transformations. Transformants were plated on SD-U plates to select for complementation of uridine auxotrophy. Individual colonies from the transformation plates were selected to extract plasmid DNA using the Zymoprep™ Yeast Plasmid Miniprep II kit (Zymo Research, Orange, Calif., USA). From each miniprep 1 μL was directly transformed into One Shot® TOP10 chemically competent *E. coli* cells (Life Technologies, Grand Island, N.Y., USA), and plated on LB plates with carbenicillin. Individual colonies from the transformation plates were selected to extract plasmid DNA using the QIAprep Spin Miniprep kit (Qiagen Inc., Valencia, Calif., USA). DNA obtained this way was sequenced at Sequetech Corporation (Mountain View, Calif., USA), and a plasmid with the correct sequence was linearized by restriction digest with SnaBI (Thermo Scientific, Grand Island, N.Y., USA), followed by de-phosphorylation by Alkaline Phosphatase (Roche, Indianapolis, Ind., USA). The resulting gene replacement cassette was purified using the QIAquick PCR Purification kit (Qiagen Inc., Valencia, Calif., USA) or ethanol precipitation.

7.2. GICC2071 Host Strain Transformation with Nik1$^{M786T}$ Allele-Containing Gene Replacement Cassette, Candidate Selection, Verification and Characterization The purified concentrated gene replacement cassette was transformed into the *Aspergillus niger* host strain GICC2071 (a non-recombinant strain derived from a glucoamylase over-producing mutant, UVK143f, itself derived from *Aspergillus niger* var. *awamori* NRRL3112, and having an inactive pyrG gene) using PEG-mediated transformation (Campbell et al., "Improved transformation efficiency of *Aspergillus niger* using the homologous niaD gene for nitrate reductase", Current Genetics, 16:53-56, 1989). Transformants were plated on minimal medium without uridine using overlays, and incubated at 32° C. Genomic DNA from transformants was extracted using CelLytic™ Y Cell Lysis Reagent (Sigma-Aldrich Co., St. Louis, Mo., USA). This genomic DNA was then used as template for diagnostic PCRs to confirm homologous recombination of the gene replacement at the native nik1 locus. The primer pairs used for diagnostic PCR are specified below.

RN0591

(SEQ ID NO: 36)

(5'-GACGTGAATACGATGGCCGA-3');

and

-continued

```
RN0592
                                         (SEQ ID NO: 37)
(5'-AACGTTTGGGCTTGCGAGG-3').

RN0577
                                         (SEQ ID NO: 38)
(5'-AGGTCGACTATCCGGTTAGAC-3');
and RN0583
                                         (SEQ ID NO: 39)
(5'-GCGACTCCCAAGCAGAAGC-3').
```

Integration of the nik1$^{M786T}$ mutation was confirmed by sequencing (Sequetech, Mountain View, Calif., USA).

Three strains with verified homologous integration of the nik1$^{M786T}$-containing gene replacement cassette labeled GICC2071 Nik1$^{M786T}$ mutants #99, 117 and 121 were selected. The selected strains were used for determining the effect of the gene replacement on protein production.

7.3 Fermentation of A. niger GICC2071 Nik1$^{M786T}$ to Evaluate Total Protein Production Aspergillus niger control strain GICC2071 and GICC2071 Nik$^{M786T}$ mutants #99, 117, and 121 were grown under identical conditions in 50-ml submerged (liquid) culture, and their total protein production was compared in shake flasks.

To create a seed culture, the spores of each strain were added separately to 50 mL of YEG (5 g/L yeast extract, 22 g/l glucose, H$_2$O) in a 250 mL flask. The cultures were grown for 24 hours at 37° C. and 200 rpm in a shaking incubator. After 24 hours, 5 ml of seed culture were added to 45 ml of Promosoy Special media (Ward, M. et al. (2004) Appl. Environ. Microbiol. 70:2567-2576) in 250-ml 4-baffled shake flasks, in triplicate, for protein production. Flasks were incubated at 37° C. with shaking at 200 rpm for 4 days. Secreted protein was harvested by spinning down cultures at 4000 rpm for 25 minutes in an Eppendorf 5804 R (Fisher Scientific, Pittsburgh, Pa., USA) and collecting the supernatant.

Total protein production was evaluated by SDS-PAGE (Life Technologies, Grand Island, N.Y., USA), and by precipitating the proteins with trichloroacetic acid (TCA) followed by a BCA protein assay (ThermoFisher Scientific, Grand Island, N.Y., USA). The activity of proteins that use p-nitrophenyl-α-D-glucopyranoside (Sigma-Aldrich Co., St. Louis, Mo., USA) as substrate, such as glucoamylase, was evaluated as well.

A supernatant volume of 4 μl from each of the control strain GICC2071 containing the wild type nik1 allele, as well as GICC2071 Nik1$^{M786T}$ mutants #99, 117, and 121, was run on 4-12% NuPAGE gels (Life Technologies, Life Technologies, Grand Island, N.Y., USA) based on the manufacturer-provided protocol. SDS-PAGE revealed that GICC Nik1$^{M786T}$ mutant strain #99 produced protein at levels lower than GICC2071 control, whereas GICC Nik1$^{M786T}$ mutants #117 and 121 showed an improvement in total protein over the GICC2071 control containing the native nik1 allele (FIG. 15).

For the BCA protein assay, supernatant from control strain GICC2071, GICC2071 Nik1$^{M786T}$ mutants #99, 117, and 121, were precipitated in trichloroacetic acid and re-suspended in 0.1 N sodium hydroxide prior to BCA protein assay. The BCA protein assay was performed according to manufacturer protocol. GICC Nik1$^{M786T}$ mutants #99 and #121 showed reduced total protein compared to GICC control containing the native nik1 allele, and mutant #117 had equivalent total protein compared to the GICC2071 control.

Activity of supernatant enzymes on p-nitrophenyl-α-D-glucopyranoside—PNPG substrate (Sigma-Aldrich Co., St. Louis, Mo., USA) was evaluated. Supernatant from control strain GICC2071, and GICC2071 Nik1$^{M786T}$ mutants #99, 117, and 121 was aliquoted into wells of a 96-well plate (Corning, Corning, N.Y., USA), followed by incubation with PNPG for 8 minutes and 45 seconds. The enzymatic reaction was stopped by addition of 0.1 M borate solution, pH 9.2, and absorbance was read at 400 nm. GICC Nik1$^{M786T}$ mutant #99 showed decreased supernatant enzyme activity on PNPG substrate compared to GICC2071 containing the wild type nik1 allele, whereas GICC Nik1$^{M786T}$ mutants #117 and 121 showed higher supernatant enzyme activity on PNPG substrate compared to the GICC2071 control (FIG. 16).

GICC2071 Nik1$^{M786T}$ mutant #117 showed protein production higher than the GICC2071 control, as seen on SDS gels (FIG. 15), as well as higher PNPG activity (FIG. 16), suggesting that introducing the mutated nik1$^{M786T}$ histidine kinase gene allele into Aspergillus niger can cause an increase in protein production.

What is claimed is:

1. An engineered *Trichoderma* spp. fungal strain capable of producing an increased level of a protein of interest as compared to a parental strain, wherein the engineered fungal strain comprises a variant histidine kinase gene encoding a polypeptide comprising an amino acid sequence comprising a mutation at position 743 of SEQ ID NO:1.

2. The engineered fungal strain of claim 1, wherein the mutation at position 743 is a mutation replacing the methionine residue at that position with a threonine residue (M743T).

3. The engineered fungal strain of claim 1, which is capable of producing at least about 5% more of a protein of interest as compared to its parental strain.

* * * * *

SEQUENCE LISTING

```
<160> NUMBER OF SEQ ID NOS: 43

<210> SEQ ID NO 1
<211> LENGTH: 1343
<212> TYPE: PRT
<213> ORGANISM: Trichoderma reesei

<400> SEQUENCE: 1

Met Ile Glu Asp Thr Ala Ala Leu Ala Ala Ala Glu Leu Ile Ala
1               5                   10                  15

Ser Leu Ala Cys Asp Pro Ala Ser Ala Ser Ala Ser Ser Leu Val
                20                  25                  30

Ser Val Gly Pro Gly Ser Ser Ile Lys Leu Pro Gly Arg Glu Asn Pro
            35                  40                  45

Ala Lys Arg Thr Leu Glu Ile Glu Leu Glu Lys Leu Val Leu Arg Ile
        50                  55                  60
```

```
Ser Gln Leu Glu Ser Arg Ala Ser Ala Ser Asn Ala Ser Val Phe
 65                  70                  75                  80

Pro Glu Thr Pro Asn Glu Val Asn Asp Thr Leu Phe Asn Asp Val
                 85                  90                  95

Asp Pro Ser Val Asn Gly Arg Pro Val Ala Pro Gln Pro Arg Leu
                100                 105                 110

Ser Gln Ala Gln Gln Gly Ser Leu Asp Ser Pro Ile Phe Val Ser Arg
                115                 120                 125

Gln Leu Thr Lys Glu Ala Leu Gln Gly Leu Arg Asp His Val Asp Asp
                130                 135                 140

Gln Ser Lys Leu Leu Asp Ser Gln Arg Gln Glu Leu Ala Gly Val Asn
145                 150                 155                 160

Ala Gln Leu Leu Glu Gln Lys Gln Leu Gln Glu Arg Ala Leu Ala Met
                165                 170                 175

Leu Glu Gln Glu Arg Val Ala Thr Leu Glu Arg Glu Leu Trp Lys His
                180                 185                 190

Gln Lys Ala Asn Glu Ala Phe Gln Lys Ala Leu Arg Glu Ile Gly Glu
                195                 200                 205

Ile Val Thr Ala Val Ala Arg Gly Asp Leu Thr Met Lys Val Arg Met
210                 215                 220

Asn Ser Val Glu Met Asp Pro Glu Ile Thr Thr Phe Lys Arg Thr Ile
225                 230                 235                 240

Asn Ala Met Met Asp Gln Leu Gln Thr Phe Ala Ser Glu Val Ser Arg
                245                 250                 255

Val Ala Arg Glu Val Gly Thr Glu Gly Leu Leu Gly Gly Gln Ala Arg
                260                 265                 270

Ile Gly Gly Val Asp Gly Val Trp Lys Glu Leu Thr Asp Asn Val Asn
                275                 280                 285

Ile Met Ala Gln Asn Leu Thr Asp Gln Val Arg Glu Ile Ala Ser Val
                290                 295                 300

Thr Thr Ala Val Ala His Gly Asp Leu Thr Lys Lys Ile Glu Arg Pro
305                 310                 315                 320

Ala Lys Gly Glu Ile Leu Gln Leu Gln Gln Thr Ile Asn Thr Met Val
                325                 330                 335

Asp Gln Leu Arg Thr Phe Ala Ser Glu Val Thr Arg Val Ala Arg Asp
                340                 345                 350

Val Gly Thr Glu Gly Ile Leu Gly Gly Gln Ala Asp Val Gly Gly Val
                355                 360                 365

Lys Gly Met Trp Asn Asp Leu Thr Val Asn Val Asn Ala Met Ala Asn
                370                 375                 380

Asn Leu Thr Thr Gln Val Arg Asp Ile Ile Lys Val Thr Thr Ala Val
385                 390                 395                 400

Ala Lys Gly Asp Leu Thr Gln Lys Val Gln Ala Glu Cys Arg Gly Glu
                405                 410                 415

Met Phe Lys Leu Lys Ser Thr Ile Asn Ser Met Val Asp Gln Leu Gln
                420                 425                 430

Gln Phe Ala Arg Glu Val Thr Lys Ile Ala Arg Glu Val Gly Thr Glu
                435                 440                 445

Gly Arg Leu Gly Gly Gln Ala Thr Val His Asp Val Glu Gly Thr Trp
                450                 455                 460

Arg Asp Leu Thr Glu Asn Val Asn Gly Met Ala Met Asn Leu Thr Thr
465                 470                 475                 480

Gln Val Arg Glu Ile Ala Lys Val Thr Thr Ala Val Ala Arg Gly Asp
```

```
                485                 490                 495
Leu Thr Lys Lys Ile Gly Val Glu Val Lys Gly Glu Ile Leu Glu Leu
            500                 505                 510
Lys Asn Thr Ile Asn Gln Met Val Asp Arg Leu Gly Thr Phe Ala Val
            515                 520                 525
Glu Val Ser Lys Val Ala Arg Glu Val Gly Thr Asp Gly Thr Leu Gly
            530                 535                 540
Gly Gln Ala Gln Val Ala Asn Val Glu Gly Lys Trp Lys Asp Leu Thr
545                 550                 555                 560
Glu Asn Val Asn Thr Met Ala Ser Asn Leu Thr Val Gln Val Arg Ser
                565                 570                 575
Ile Ser Ala Val Thr Gln Ala Ile Ala Asn Gly Asp Met Ser Gln Thr
            580                 585                 590
Ile Asp Val Glu Ala Asn Gly Glu Ile Gln Val Leu Lys Glu Thr Ile
            595                 600                 605
Asn Asn Met Val Ser Arg Leu Ser Ser Phe Cys Tyr Glu Val Gln Arg
            610                 615                 620
Val Ala Lys Asp Val Gly Val Asp Gly Lys Met Gly Ala Gln Ala Asp
625                 630                 635                 640
Val Ala Gly Leu Asn Gly Arg Trp Lys Glu Ile Thr Thr Asp Val Asn
                645                 650                 655
Thr Met Ala Ser Asn Leu Thr Thr Gln Val Arg Ala Phe Ser Asp Ile
            660                 665                 670
Thr Asn Leu Ala Thr Asp Gly Asp Phe Thr Lys Leu Val Asp Val Glu
            675                 680                 685
Ala Ser Gly Glu Met Asp Glu Leu Lys Lys Lys Ile Asn Gln Met Ile
            690                 695                 700
Ser Asn Leu Arg Asp Ser Ile Gln Arg Asn Thr Gln Ala Arg Glu Ala
705                 710                 715                 720
Ala Glu Leu Ala Asn Lys Thr Lys Ser Glu Phe Leu Ala Asn Met Ser
                725                 730                 735
His Glu Ile Arg Thr Pro Met Asn Gly Ile Ile Gly Met Thr Gln Leu
            740                 745                 750
Thr Leu Asp Thr Asp Leu Thr Gln Tyr Gln Arg Glu Met Leu Asn Ile
            755                 760                 765
Val Asn Asp Leu Ala Asn Ser Leu Leu Thr Ile Asp Asp Ile Leu
            770                 775                 780
Asp Leu Ser Lys Ile Glu Ala Arg Arg Met Val Ile Glu Glu Ile Pro
785                 790                 795                 800
Tyr Thr Leu Arg Gly Thr Val Phe Asn Ala Leu Lys Thr Leu Ala Val
                805                 810                 815
Lys Ala Asn Glu Lys Phe Leu Asp Leu Thr Tyr Lys Val Asp Ser Ser
            820                 825                 830
Val Pro Asp Tyr Val Ile Gly Asp Ser Phe Arg Leu Arg Gln Ile Ile
            835                 840                 845
Leu Asn Leu Val Gly Asn Ala Ile Lys Phe Thr Glu His Gly Glu Val
            850                 855                 860
Ser Leu Thr Ile Gln Glu Gln Glu Asp Lys Arg His Val Gly Pro Gly
865                 870                 875                 880
Glu Tyr Ala Ile Glu Phe Ile Val Glu Asp Thr Gly Ile Gly Ile Ala
                885                 890                 895
Lys Asp Lys Leu Asn Leu Ile Phe Asp Thr Phe Gln Gln Ala Asp Gly
            900                 905                 910
```

```
Ser Met Thr Arg Lys Phe Gly Gly Thr Gly Leu Gly Leu Ser Ile Ser
    915                 920                 925
Lys Arg Phe Val Asn Leu Met Gly Gly Asp Leu Trp Val Asn Ser Glu
    930                 935                 940
Val Gly Lys Gly Ser Glu Phe His Phe Thr Cys Arg Val Lys Leu Ala
945                 950                 955                 960
Asp Val His Ala Glu Ser Val Gln Gln Gln Leu Lys Pro Tyr Arg Gly
                    965                 970                 975
His Gln Val Leu Phe Val Asp Lys Ser Gln Ser Asn Ala Ala Thr His
                    980                 985                 990
Ile Gly Glu Met Leu Glu Glu Ile Gly Leu His Pro Val Val Val Asn
                    995                 1000                1005
Ser Glu Lys Ser Ser Ala Leu Thr Arg Leu Lys Glu Gly Gly Ala
    1010                1015                1020
Leu Pro Tyr Asp Ala Ile Ile Val Asp Ser Ile Asp Thr Ala Arg
    1025                1030                1035
Arg Leu Arg Ala Val Asp Asp Phe Lys Tyr Leu Pro Ile Val Leu
    1040                1045                1050
Leu Ala Pro Val Val His Val Ser Leu Lys Ser Cys Leu Asp Leu
    1055                1060                1065
Gly Ile Thr Ser Tyr Met Thr Met Pro Cys Lys Leu Ile Asp Leu
    1070                1075                1080
Ser Asn Gly Met Ile Pro Ala Leu Glu Asn Arg Ala Thr Pro Ser
    1085                1090                1095
Leu Ala Asp Val Thr Lys Ser Phe Glu Ile Leu Leu Ala Glu Asp
    1100                1105                1110
Asn Thr Val Asn Gln Lys Leu Ala Val Lys Ile Leu Glu Lys Tyr
    1115                1120                1125
His His Val Val Thr Val Val Gly Asn Gly Trp Glu Ala Val Glu
    1130                1135                1140
Ala Val Lys Gln Lys Lys Phe Asp Val Ile Leu Met Asp Val Gln
    1145                1150                1155
Met Pro Ile Met Gly Gly Phe Glu Ala Thr Gly Lys Ile Arg Glu
    1160                1165                1170
Tyr Glu Arg Gly Met Gly Thr His Arg Thr Pro Ile Ile Ala Leu
    1175                1180                1185
Thr Ala His Ala Met Met Gly Asp Arg Glu Lys Cys Ile Gln Ala
    1190                1195                1200
Gln Met Asp Glu Tyr Leu Ser Lys Pro Leu Gln Gln Asn Gln Leu
    1205                1210                1215
Ile Gln Thr Ile Leu Lys Cys Ala Thr Leu Gly Gly Ala Leu Leu
    1220                1225                1230
Glu Lys Asn Arg Glu Arg Glu Leu Ala Leu Gln Ala Glu Ala Lys
    1235                1240                1245
Ala Ser Gly Arg Leu Asp Gly Glu Arg Gly Met Leu Arg Pro Gly
    1250                1255                1260
Leu Glu Gly Arg Ser Phe Thr Thr Arg Glu Pro Met Thr Lys Ser
    1265                1270                1275
Arg Pro Ser Leu Thr Lys Ala Thr Ser Lys Ala Leu Glu Glu Ala
    1280                1285                1290
Arg Asn Ala Ala Ala Ala Asn Ala Gly Leu Arg Phe Ser Glu Leu
    1295                1300                1305
```

Thr Gly Phe Ser Ala Asp Leu Met Glu Glu Leu Asp Asn Met Glu
    1310                1315                1320

Asp Glu Asp Ser Phe Thr Lys Ala Arg Glu Asp Leu Ala Asp Arg
    1325                1330                1335

Arg Ser Leu Ser Ser
    1340

<210> SEQ ID NO 2
<211> LENGTH: 55
<212> TYPE: DNA
<213> ORGANISM: Artificial Sequence
<220> FEATURE:
<223> OTHER INFORMATION: primer

<400> SEQUENCE: 2
cgattaagtt gggtaacgcc agggcctagg tggctttgag cggtgttgat gtgta        55

<210> SEQ ID NO 3
<211> LENGTH: 55
<212> TYPE: DNA
<213> ORGANISM: Artificial Sequence
<220> FEATURE:
<223> OTHER INFORMATION: primer

<400> SEQUENCE: 3
tacacatcaa caccgctcaa agccacctag gccctggcgt tacccaactt aatcg        55

<210> SEQ ID NO 4
<211> LENGTH: 55
<212> TYPE: DNA
<213> ORGANISM: Artificial Sequence
<220> FEATURE:
<223> OTHER INFORMATION: primer

<400> SEQUENCE: 4
ctgctcgaga agaaccgtga gcgagcctag ggtgagggtt aattgcgcgc ttggc        55

<210> SEQ ID NO 5
<211> LENGTH: 55
<212> TYPE: DNA
<213> ORGANISM: Artificial Sequence
<220> FEATURE:
<223> OTHER INFORMATION: primer

<400> SEQUENCE: 5
gccaagcgcg caattaaccc tcaccctagg ctcgctcacg gttcttctcg agcag        55

<210> SEQ ID NO 6
<211> LENGTH: 90
<212> TYPE: DNA
<213> ORGANISM: Artificial Sequence
<220> FEATURE:
<223> OTHER INFORMATION: primer

<400> SEQUENCE: 6
gaatccacgt gccgcgaggc tcagcattta aatataactt cgtatagcat acattatacg    60
aagttatcct gggcttgtga ctggtcgcga                                     90

<210> SEQ ID NO 7
<211> LENGTH: 90
<212> TYPE: DNA
<213> ORGANISM: Artificial Sequence
<220> FEATURE:
<223> OTHER INFORMATION: primer

```
<400> SEQUENCE: 7
tcgcgaccag tcacaagccc aggataactt cgtataatgt atgctatacg aagttatatt    60
taaatgctga gcctcgcggc acgtggattc                                     90

<210> SEQ ID NO 8
<211> LENGTH: 90
<212> TYPE: DNA
<213> ORGANISM: Artificial Sequence
<220> FEATURE:
<223> OTHER INFORMATION: primer

<400> SEQUENCE: 8
cgtaacaccc aatacgccgg ccgataactt cgtatagcat acattatacg aagttatgcg    60
gccgcgccca ggatcacaaa cccaccgcag                                     90

<210> SEQ ID NO 9
<211> LENGTH: 90
<212> TYPE: DNA
<213> ORGANISM: Artificial Sequence
<220> FEATURE:
<223> OTHER INFORMATION: primer

<400> SEQUENCE: 9
ctgcggtggg tttgtgatcc tgggcgcggc cgcataactt cgtataatgt atgctatacg    60
aagttatcgg ccggcgtatt gggtgttacg                                     90

<210> SEQ ID NO 10
<211> LENGTH: 50
<212> TYPE: DNA
<213> ORGANISM: Artificial Sequence
<220> FEATURE:
<223> OTHER INFORMATION: primer

<400> SEQUENCE: 10
gaaattgcct ccgtcacaac agccgtcgct cacggcgatc tgacaaagaa                50

<210> SEQ ID NO 11
<211> LENGTH: 50
<212> TYPE: DNA
<213> ORGANISM: Artificial Sequence
<220> FEATURE:
<223> OTHER INFORMATION: primer

<400> SEQUENCE: 11
ttctttgtca gatcgccgtg agcgacggct gttgtgacgg aggcaatttc                50

<210> SEQ ID NO 12
<211> LENGTH: 25
<212> TYPE: DNA
<213> ORGANISM: Artificial Sequence
<220> FEATURE:
<223> OTHER INFORMATION: primer

<400> SEQUENCE: 12
tggctttgag cggtgttgat gtgta                                          25

<210> SEQ ID NO 13
<211> LENGTH: 25
<212> TYPE: DNA
<213> ORGANISM: Artificial Sequence
<220> FEATURE:
<223> OTHER INFORMATION: primer

<400> SEQUENCE: 13
```
ctcgctcacg gttcttctcg agcag                                        25

<210> SEQ ID NO 14
<211> LENGTH: 20
<212> TYPE: DNA
<213> ORGANISM: Artificial Sequence
<220> FEATURE:
<223> OTHER INFORMATION: primer

<400> SEQUENCE: 14
cgaactgtga cctttcaagt                                              20

<210> SEQ ID NO 15
<211> LENGTH: 20
<212> TYPE: DNA
<213> ORGANISM: Artificial Sequence
<220> FEATURE:
<223> OTHER INFORMATION: primer

<400> SEQUENCE: 15
gcacacacat ctcggcctta                                              20

<210> SEQ ID NO 16
<211> LENGTH: 90
<212> TYPE: DNA
<213> ORGANISM: Artificial Sequence
<220> FEATURE:
<223> OTHER INFORMATION: primer

<400> SEQUENCE: 16
cctggggaac cccccagcgc ccggcgagct cataacttcg tatagcatac attatacgaa   60
gttatcctgg gcttgtgact ggtcgcgagc                                   90

<210> SEQ ID NO 17
<211> LENGTH: 90
<212> TYPE: DNA
<213> ORGANISM: Artificial Sequence
<220> FEATURE:
<223> OTHER INFORMATION: primer

<400> SEQUENCE: 17
ctttcgccgt ccaggcgtcc agacacctgg tataacttcg tataatgtat gctatacgaa   60
gttatcggcc ggcgtattgg gtgttacgga                                   90

<210> SEQ ID NO 18
<211> LENGTH: 91
<212> TYPE: DNA
<213> ORGANISM: Artificial Sequence
<220> FEATURE:
<223> OTHER INFORMATION: primer

<400> SEQUENCE: 18
tccgtaacac ccaatacgcc ggccgataac ttcgtatagc atacattata cgaagttata   60
ccaggtgtct ggacgcctgg acggcgaaag a                                 91

<210> SEQ ID NO 19
<211> LENGTH: 63
<212> TYPE: DNA
<213> ORGANISM: Artificial Sequence
<220> FEATURE:
<223> OTHER INFORMATION: primer

<400> SEQUENCE: 19

```
cgccaagcgc gcaattaacc ctcacggcca taatggccgc tgggttctga acctgtaaag    60
tac                                                                  63

<210> SEQ ID NO 20
<211> LENGTH: 63
<212> TYPE: DNA
<213> ORGANISM: Artificial Sequence
<220> FEATURE:
<223> OTHER INFORMATION: primer

<400> SEQUENCE: 20
gtactttaca ggttcagaac ccagcggcca ttatggccgt gagggttaat tgcgcgcttg    60
gcg                                                                  63

<210> SEQ ID NO 21
<211> LENGTH: 56
<212> TYPE: DNA
<213> ORGANISM: Artificial Sequence
<220> FEATURE:
<223> OTHER INFORMATION: primer

<400> SEQUENCE: 21
tgtaggtaag gtagatcgaa ctgtgaagct tccctggcgt tacccaactt aatcgc        56

<210> SEQ ID NO 22
<211> LENGTH: 56
<212> TYPE: DNA
<213> ORGANISM: Artificial Sequence
<220> FEATURE:
<223> OTHER INFORMATION: primer

<400> SEQUENCE: 22
gcgattaagt tgggtaacgc cagggaagct tcacagttcg atctacctta cctaca        56

<210> SEQ ID NO 23
<211> LENGTH: 90
<212> TYPE: DNA
<213> ORGANISM: Artificial Sequence
<220> FEATURE:
<223> OTHER INFORMATION: primer

<400> SEQUENCE: 23
gctcgcgacc agtcacaagc ccaggataac ttcgtataat gtatgctata cgaagttatg    60
agctcgccgg gcgctggggg gttccccagg                                     90

<210> SEQ ID NO 24
<211> LENGTH: 25
<212> TYPE: DNA
<213> ORGANISM: Artificial Sequence
<220> FEATURE:
<223> OTHER INFORMATION: primer

<400> SEQUENCE: 24
cacagttcga tctaccttac ctaca                                          25

<210> SEQ ID NO 25
<211> LENGTH: 25
<212> TYPE: DNA
<213> ORGANISM: Artificial Sequence
<220> FEATURE:
<223> OTHER INFORMATION: primer

<400> SEQUENCE: 25
gctgggttct gaacctgtaa agtac                                          25
```

<210> SEQ ID NO 26
<211> LENGTH: 48
<212> TYPE: DNA
<213> ORGANISM: Artificial Sequence
<220> FEATURE:
<223> OTHER INFORMATION: primer

<400> SEQUENCE: 26
cgataagctt gatatcgaat tcctggttcc tgaatagact tggggttg                48

<210> SEQ ID NO 27
<211> LENGTH: 54
<212> TYPE: DNA
<213> ORGANISM: Artificial Sequence
<220> FEATURE:
<223> OTHER INFORMATION: primer

<400> SEQUENCE: 27
ccgggtaccg agctcgaatt cgtaatcatg ggcccagtac tagatagata cctg          54

<210> SEQ ID NO 28
<211> LENGTH: 21
<212> TYPE: DNA
<213> ORGANISM: Artificial Sequence
<220> FEATURE:
<223> OTHER INFORMATION: primer

<400> SEQUENCE: 28
gccagtgcca agcttatcac c                                              21

<210> SEQ ID NO 29
<211> LENGTH: 21
<212> TYPE: DNA
<213> ORGANISM: Artificial Sequence
<220> FEATURE:
<223> OTHER INFORMATION: primer

<400> SEQUENCE: 29
ccatgattac gaattcgagc t                                              21

<210> SEQ ID NO 30
<211> LENGTH: 51
<212> TYPE: DNA
<213> ORGANISM: Artificial Sequence
<220> FEATURE:
<223> OTHER INFORMATION: primer

<400> SEQUENCE: 30
gataagggac ggtgataagc ttggcactgg cggatttgct gccagcttta c             51

<210> SEQ ID NO 31
<211> LENGTH: 21
<212> TYPE: DNA
<213> ORGANISM: Artificial Sequence
<220> FEATURE:
<223> OTHER INFORMATION: primer

<400> SEQUENCE: 31
cttcaactct gcgatctctc c                                              21

<210> SEQ ID NO 32
<211> LENGTH: 20
<212> TYPE: DNA
<213> ORGANISM: Artificial Sequence
<220> FEATURE:

<223> OTHER INFORMATION: primer

<400> SEQUENCE: 32
cacggttacc aaggctgtgg                                              20

<210> SEQ ID NO 33
<211> LENGTH: 33
<212> TYPE: DNA
<213> ORGANISM: Artificial Sequence
<220> FEATURE:
<223> OTHER INFORMATION: primer

<400> SEQUENCE: 33
ccaatgatac cgttcgtggg cgtccggatc tcg                               33

<210> SEQ ID NO 34
<211> LENGTH: 42
<212> TYPE: DNA
<213> ORGANISM: Artificial Sequence
<220> FEATURE:
<223> OTHER INFORMATION: primer

<400> SEQUENCE: 34
ccggacgccc acgaacggta tcattggtat gacgcagttg ac                     42

<210> SEQ ID NO 35
<211> LENGTH: 54
<212> TYPE: DNA
<213> ORGANISM: Artificial Sequence
<220> FEATURE:
<223> OTHER INFORMATION: primer

<400> SEQUENCE: 35
cggtggcggc cgctctagaa ctagtggatc gggtgcattt caccactact tgag         54

<210> SEQ ID NO 36
<211> LENGTH: 20
<212> TYPE: DNA
<213> ORGANISM: Artificial Sequence
<220> FEATURE:
<223> OTHER INFORMATION: primer

<400> SEQUENCE: 36
gacgtgaata cgatggccga                                              20

<210> SEQ ID NO 37
<211> LENGTH: 19
<212> TYPE: DNA
<213> ORGANISM: Artificial Sequence
<220> FEATURE:
<223> OTHER INFORMATION: primer

<400> SEQUENCE: 37
aacgtttggg cttgcgagg                                               19

<210> SEQ ID NO 38
<211> LENGTH: 21
<212> TYPE: DNA
<213> ORGANISM: Artificial Sequence
<220> FEATURE:
<223> OTHER INFORMATION: primer

<400> SEQUENCE: 38
aggtcgacta tccggttaga c                                            21

<210> SEQ ID NO 39
<211> LENGTH: 19
<212> TYPE: DNA
<213> ORGANISM: Artificial Sequence
<220> FEATURE:
<223> OTHER INFORMATION: primer

<400> SEQUENCE: 39
gcgactccca agcagaagc                                              19

<210> SEQ ID NO 40
<211> LENGTH: 20
<212> TYPE: DNA
<213> ORGANISM: Artificial Sequence
<220> FEATURE:
<223> OTHER INFORMATION: primer

<400> SEQUENCE: 40
cggcatggcc atgaacctca                                             20

<210> SEQ ID NO 41
<211> LENGTH: 20
<212> TYPE: DNA
<213> ORGANISM: Artificial Sequence
<220> FEATURE:
<223> OTHER INFORMATION: primer

<400> SEQUENCE: 41
gcactgaagc cggttagttc                                             20

<210> SEQ ID NO 42
<211> LENGTH: 20
<212> TYPE: DNA
<213> ORGANISM: Artificial Sequence
<220> FEATURE:
<223> OTHER INFORMATION: primer

<400> SEQUENCE: 42
ctgtccagct tctgctacga                                             20

<210> SEQ ID NO 43
<211> LENGTH: 1353
<212> TYPE: PRT
<213> ORGANISM: Aspergillus niger

<400> SEQUENCE: 43

Met Ala Gly Ala Asp Glu Thr Leu Ala Ala Ala Ala Ile Leu Arg
1               5                   10                  15

Gly Leu Ala Lys Glu Thr Pro Ser Ser Ser Ala Pro Pro Phe Asp Phe
            20                  25                  30

Glu Phe Ser His Pro Pro Ala Asn Gly Tyr Asp Thr Lys Leu Ala Lys
        35                  40                  45

Leu Pro Gly Glu Thr Ser Ser Ala Lys Ala Ala Phe Glu Gln Glu Leu
    50                  55                  60

Glu Ala Leu Val Arg Arg Val Arg His Leu Glu Phe Gln Asn Val Ser
65                  70                  75                  80

His His Gln Ser Thr Pro Lys Ser Ser Gln Ser Ser Leu Thr Pro Gly
                85                  90                  95

Glu Lys Asp Ala Asp Phe Leu Trp Ser Phe Gly Leu Ser Arg Val Ser
            100                 105                 110

Ser Arg Asp Gly Ser Asp Ser Cys Leu Ser Gln His Gln Lys Thr Thr
        115                 120                 125

-continued

Gln Gln Gln Gln Gln Gln Gln Pro His Gly Ser Arg Arg Ser Ala Ile
130                 135                 140

Glu Pro Glu Asp His Glu Val Glu Glu Asp Ile Asp Asp Glu Glu Ser
145                 150                 155                 160

Asp Glu Asp Glu Glu Leu Asn Ser Arg Thr Arg Leu Val Arg Glu Glu
                165                 170                 175

Asp Ile Ser Tyr Leu Arg Asn His Val Gln Lys Gln Ala Glu Glu Ile
            180                 185                 190

Ser Phe Gln Lys Asp Ile Ile Ala Gln Val Arg Asp Glu Leu Gln Gln
        195                 200                 205

Gln Glu Glu Gln Thr Arg Arg Ala Leu Thr Lys Val Glu Asn Glu Asp
210                 215                 220

Val Val Leu Leu Glu Arg Glu Leu Arg Lys His Gln Gln Ala Asn Glu
225                 230                 235                 240

Ala Phe Gln Lys Ala Leu Arg Glu Ile Gly Gly Ile Ile Thr Gln Val
                245                 250                 255

Ala Asn Gly Asp Leu Ser Met Lys Val Gln Ile His Pro Leu Glu Met
            260                 265                 270

Asp Pro Glu Ile Ala Thr Phe Lys Arg Thr Ile Asn Thr Met Met Asp
        275                 280                 285

Gln Leu Gln Val Phe Gly Ser Glu Val Ser Arg Val Ala Arg Glu Val
290                 295                 300

Gly Thr Glu Gly Ile Leu Gly Gly Gln Ala Gln Ile Thr Gly Val His
305                 310                 315                 320

Gly Ile Trp Lys Glu Leu Thr Glu Asn Val Asn Ile Met Ala Lys Asn
                325                 330                 335

Leu Thr Asp Gln Val Arg Glu Ile Ala Ala Val Thr Thr Ala Val Ala
            340                 345                 350

His Gly Asp Leu Ser Gln Lys Ile Glu Ser Arg Ala Gln Gly Glu Ile
        355                 360                 365

Leu Glu Leu Gln Gln Thr Ile Asn Thr Met Val Asp Gln Leu Arg Thr
370                 375                 380

Phe Ala Thr Glu Val Thr Arg Val Ala Arg Asp Val Gly Thr Glu Gly
385                 390                 395                 400

Val Leu Gly Gly Gln Ala Gln Ile Glu Gly Val Gln Gly Met Trp Asn
                405                 410                 415

Glu Leu Thr Val Asn Val Asn Ala Met Ala Asn Asn Leu Thr Thr Gln
            420                 425                 430

Val Arg Asp Ile Ala Thr Val Thr Lys Ala Val Ala Lys Gly Asp Leu
        435                 440                 445

Thr Gln Lys Val Gln Ala Asn Cys Lys Gly Glu Ile Ala Glu Leu Lys
450                 455                 460

Asn Ile Ile Asn Ser Met Val Asp Gln Leu Arg Gln Phe Ala Gln Glu
465                 470                 475                 480

Val Thr Lys Ile Ala Lys Glu Val Gly Thr Asp Gly Val Leu Gly Gly
                485                 490                 495

Gln Ala Thr Val Asn Asp Val Glu Gly Thr Trp Lys Asp Leu Thr Glu
            500                 505                 510

Asn Val Asn Arg Met Ala Asn Asn Leu Thr Thr Gln Val Arg Glu Ile
        515                 520                 525

Ala Asp Val Thr Thr Ala Val Ala Lys Gly Asp Leu Thr Lys Lys Val
530                 535                 540

Thr Ala Asn Val Gln Gly Glu Ile Leu Asp Leu Lys Ser Thr Ile Asn

```
                545                 550                 555                 560
Gly Met Val Asp Arg Leu Asn Thr Phe Ala Phe Glu Val Ser Lys Val
                565                 570                 575
Ala Arg Glu Val Gly Thr Asp Gly Thr Leu Gly Gly Gln Ala Lys Val
                580                 585                 590
Asp Asn Val Glu Gly Lys Trp Lys Asp Leu Thr Asp Asn Val Asn Thr
                595                 600                 605
Met Ala Gln Asn Leu Thr Ser Gln Val Arg Ser Ile Ser Asp Val Thr
                610                 615                 620
Gln Ala Ile Ala Lys Gly Asp Leu Ser Lys Lys Ile Glu Val His Ala
625                 630                 635                 640
Gln Gly Glu Ile Leu Thr Leu Lys Val Thr Ile Asn His Met Val Asp
                645                 650                 655
Arg Leu Ala Lys Phe Ala Thr Glu Leu Lys Lys Val Ala Arg Asp Val
                660                 665                 670
Gly Val Asp Gly Lys Met Gly Gly Gln Ala Asn Val Glu Gly Ile Ala
                675                 680                 685
Gly Thr Trp Lys Glu Ile Thr Glu Asp Val Asn Thr Met Ala Glu Asn
                690                 695                 700
Leu Thr Ser Gln Val Arg Ala Phe Gly Glu Ile Thr Asp Ala Ala Thr
705                 710                 715                 720
Asp Gly Asp Phe Thr Lys Leu Ile Thr Val Asn Ala Ser Gly Glu Met
                725                 730                 735
Asp Glu Leu Lys Arg Lys Ile Asn Lys Met Val Ser Asn Leu Arg Asp
                740                 745                 750
Ser Ile Gln Arg Asn Thr Ala Ala Arg Glu Ala Ala Glu Leu Ala Asn
                755                 760                 765
Arg Thr Lys Ser Glu Phe Leu Ala Asn Met Ser His Glu Ile Arg Thr
                770                 775                 780
Pro Met Asn Gly Ile Ile Gly Met Thr Gln Leu Thr Leu Asp Thr Asp
785                 790                 795                 800
Asp Leu Lys Pro Tyr Thr Arg Glu Met Leu Asn Val Val His Asn Leu
                805                 810                 815
Ala Asn Ser Leu Leu Thr Ile Ile Asp Asp Ile Leu Asp Ile Ser Lys
                820                 825                 830
Ile Glu Ala Asn Arg Met Val Ile Glu Ser Ile Pro Phe Thr Val Arg
                835                 840                 845
Gly Thr Val Phe Asn Ala Leu Lys Thr Leu Ala Val Lys Ala Asn Glu
                850                 855                 860
Lys Phe Leu Ser Leu Thr Tyr Gln Val Asp Asn Thr Val Pro Asp Tyr
865                 870                 875                 880
Val Ile Gly Asp Pro Phe Arg Leu Arg Gln Ile Leu Asn Leu Val
                885                 890                 895
Gly Asn Ala Ile Lys Phe Thr Glu His Gly Glu Val Lys Leu Thr Ile
                900                 905                 910
Cys Lys Ser Asp Arg Glu Gln Cys Ala Ala Asp Glu Tyr Ala Phe Glu
                915                 920                 925
Phe Ser Val Ser Asp Thr Gly Ile Gly Ile Glu Asp Lys Leu Asp
                930                 935                 940
Leu Ile Phe Asp Thr Phe Gln Gln Ala Asp Gly Ser Thr Arg Arg
945                 950                 955                 960
Phe Gly Gly Thr Gly Leu Gly Leu Ser Ile Ser Lys Arg Leu Val Asn
                965                 970                 975
```

```
Leu Met Gly Gly Asp Val Trp Val Thr Ser Glu Tyr Gly His Gly Ser
            980                 985                 990

Thr Phe His Phe Thr Cys Val Val Lys Leu Ala Asp Gln Ser Leu Ser
        995                 1000                1005

Val Ile Ala Ser Gln Leu Leu Pro Tyr Lys Asn His Arg Val Leu
    1010                1015                1020

Phe Ile Asp Lys Gly Glu Asn Gly Gly Gln Ala Glu Asn Val Met
    1025                1030                1035

Lys Met Leu Lys Gln Ile Asp Leu Glu Pro Leu Val Val Arg Asn
    1040                1045                1050

Glu Asp His Val Pro Pro Glu Ile Gln Asp Pro Ser Gly Lys
    1055                1060                1065

Glu Ser Gly His Ala Tyr Asp Val Ile Val Asp Ser Val Ala
    1070                1075                1080

Thr Ala Arg Leu Leu Arg Thr Phe Asp Asp Phe Lys Tyr Val Pro
    1085                1090                1095

Ile Val Leu Val Cys Pro Leu Val Cys Val Ser Leu Lys Ser Ala
    1100                1105                1110

Leu Asp Leu Gly Ile Ser Ser Tyr Met Thr Thr Pro Cys Gln Pro
    1115                1120                1125

Ile Asp Leu Gly Asn Gly Met Leu Pro Ala Leu Glu Gly Arg Ser
    1130                1135                1140

Thr Pro Ile Thr Thr Asp His Ser Arg Ser Phe Asp Ile Leu Leu
    1145                1150                1155

Ala Glu Asp Asn Asp Val Asn Gln Lys Leu Ala Val Lys Ile Leu
    1160                1165                1170

Glu Lys His Asn His Asn Val Ser Val Val Ser Asn Gly Leu Glu
    1175                1180                1185

Ala Val Glu Ala Val Lys Gln Arg Arg Tyr Asp Val Ile Leu Met
    1190                1195                1200

Asp Val Gln Met Pro Val Met Gly Gly Phe Glu Ala Thr Gly Lys
    1205                1210                1215

Ile Arg Glu Tyr Glu Arg Glu Ser Gly Leu Ser Arg Thr Pro Ile
    1220                1225                1230

Ile Ala Leu Thr Ala His Ala Met Leu Gly Asp Arg Glu Lys Cys
    1235                1240                1245

Ile Gln Ala Gln Met Asp Glu Tyr Leu Ser Lys Pro Leu Lys Gln
    1250                1255                1260

Asn Gln Met Met Gln Thr Ile Leu Lys Cys Ala Thr Leu Gly Gly
    1265                1270                1275

Ser Leu Leu Glu Lys Ser Lys Glu Ser Arg Ile Ser Ser Ser Gly
    1280                1285                1290

Glu Met His Pro Val His His Ser Gly Pro Asp Gly Lys Ser Gln
    1295                1300                1305

Gln Arg Pro Gly Leu Glu Pro Arg Ser Val Thr Ala Thr Ser Thr
    1310                1315                1320

Ile Asn Arg Gly Gly Gly Leu Ala Ser Pro Asn Val Asp Arg Ala
    1325                1330                1335

Asp Glu Leu Ala Val Glu Arg Ala Leu Leu Arg Ser Asn Ser Ser
    1340                1345                1350
```